US009370550B2

(12) United States Patent
Evans et al.

(10) Patent No.: US 9,370,550 B2
(45) Date of Patent: Jun. 21, 2016

(54) ONCOLYTIC VIRUSES AND METHODS FOR TREATING NEOPLASTIC DISORDERS

(71) Applicant: The Governors of the University of Alberta, Edmonton (CA)

(72) Inventors: David H. Evans, Edmonton (CA); Don B. Gammon, Worcester, MA (US)

(73) Assignee: The Governors of the University of Alberta, Alberta (CA)

( * ) Notice: Subject to any disclaimer, the term of this patent is extended or adjusted under 35 U.S.C. 154(b) by 34 days.

(21) Appl. No.: 14/166,606

(22) Filed: Jan. 28, 2014

(65) Prior Publication Data

US 2014/0234257 A1    Aug. 21, 2014

Related U.S. Application Data

(63) Continuation of application No. 13/383,396, filed as application No. PCT/CA2010/001065 on Jul. 9, 2010, now Pat. No. 8,679,509.

(60) Provisional application No. 61/224,694, filed on Jul. 10, 2009.

(30) Foreign Application Priority Data

Jul. 8, 2010    (CA) ..................... 2709292

(51) Int. Cl.
| | |
|---|---|
| A01N 63/00 | (2006.01) |
| C12N 7/00 | (2006.01) |
| C12N 15/00 | (2006.01) |
| C12N 15/74 | (2006.01) |
| A61K 38/16 | (2006.01) |
| A61K 45/06 | (2006.01) |
| A61K 31/17 | (2006.01) |
| A61K 31/7068 | (2006.01) |
| A61K 31/7076 | (2006.01) |
| A61K 35/768 | (2015.01) |
| C12N 15/79 | (2006.01) |

(52) U.S. Cl.
CPC .............. *A61K 38/162* (2013.01); *A61K 31/17* (2013.01); *A61K 31/7068* (2013.01); *A61K 31/7076* (2013.01); *A61K 35/768* (2013.01); *A61K 45/06* (2013.01); *C12N 7/00* (2013.01); *C12N 15/79* (2013.01); *C12N 2710/24121* (2013.01); *C12N 2710/24132* (2013.01); *C12N 2710/24162* (2013.01)

(58) Field of Classification Search
CPC ..................... C12N 7/00; C12N 15/79; C12N 2710/24121; C12N 2710/24132; C12N 2710/24162; A61K 35/768
USPC ..................... 424/93.2; 435/235.1, 320.1, 471
See application file for complete search history.

(56) References Cited

U.S. PATENT DOCUMENTS

| 6,139,834 A | 10/2000 | Martuza et al. |
| 2011/0059049 A1 | 3/2011 | Erbs et al. |

FOREIGN PATENT DOCUMENTS

| WO | WO 03/085090 | 10/2003 |
| WO | WO 2009/065546 | 5/2009 |

OTHER PUBLICATIONS

Pandey, Prativa, 2007, Abstracts, 59th Southeast regional Meeting of the American Chemical Society, Greenville, SC, United States, GEN-671, Publisher: American Chemical Society, Washington D.C.*
Bryan et al., 2013, http://www.elsevierblogs.com/currentcomments/?p=962, Implications of protein fold switching, p. 1-4.*
Advani et al. "ReVOLT: radiation-enhanced viral oncolytic therapy." International Journal of Radiation: Oncology Biology Physics, Pergamon Press, 2006, vol. 66, No. 3, pp. 637-646.
Andrei et al. "Cidofovir resistance in vaccinia virus is linked to diminished virulence in mice." J Virol, 2006, vol. 80, pp. 9391-401.
Angelova et al. "Improvement of gemcitabine-based therapy of pancreatic carcinoma by means of oncolytic parvovirus H-1PV." Clin Cancer Res, 2009, vol. 15, pp. 511-519.
Bazan-Peregrino et al. "Comparison of Molecular Strategies for Breast Cancer Virotherapy using Oncolytic Adenovirus." Hum Gene Ther, vol. 19, No. 9, 2008, pp. 873-886.
Chabes et al. "Mouse ribonucleotide reductase R2 protein: a new target for anaphase-promoting complex-Cdh1-mediated proteolysis." Proc Natl Acad Sci U S A, 2003, vol. 100, pp. 3925-3929.
Chakrabarti et al. "Compact, synthetic, vaccinia virus early/late promoter for protein expression." Biotechniques, 1997, vol. 23, pp. 1094-1097.
Chattopadhyay et al. "Effect of single amino acid mutations in the conserved GDNQ motif of L protein of Rinderpest virus on RNA synthesis in vitro and in vivo." Virus Research, 2004, vol. 99, p. 139-145.
Chen et al. "Haemonchus contortus: molecular cloning, sequencing, and expression analysis of the gene coding for the small subunit of ribonucleotide reductase." Exp Parasitol, 2005, vol. 111, pp. 250-254.
Child et al. "Insertional inactivation of the large subunit of ribonucleotide reductase encoded by vaccinia virus is associated with reduced virulence in vivo." Virology, 1990, vol. 174, pp. 625-629.
Chimploy et al. "Mouse ribonucleotide reductase control: influence of substrate binding upon interactions with allosteric effectors." J Biol Chem, 2001, vol. 276, pp. 7093-100.

(Continued)

*Primary Examiner* — Shin Lin Chen
(74) *Attorney, Agent, or Firm* — Shweta Chandra; Carol L. Francis; Bozicevic, Field & Francis, LLP

(57) ABSTRACT

The disclosure provides mutant ribonucleotide reductase strains of poxviruses including for example vaccinia viruses. The disclosure also provides methods and for the use of these mutant ribonucleotide reductase strains of vaccinia viruses in oncolytic virotherapy. Also provided in the disclosure are vector constructs for generating mutant ribonucleotide reductase strains of poxviruses including for example vaccinia viruses. The disclosure also provides poxviruses comprising a functionally inactivated R2 gene.

20 Claims, 19 Drawing Sheets

(56) References Cited

OTHER PUBLICATIONS

Figure 1:
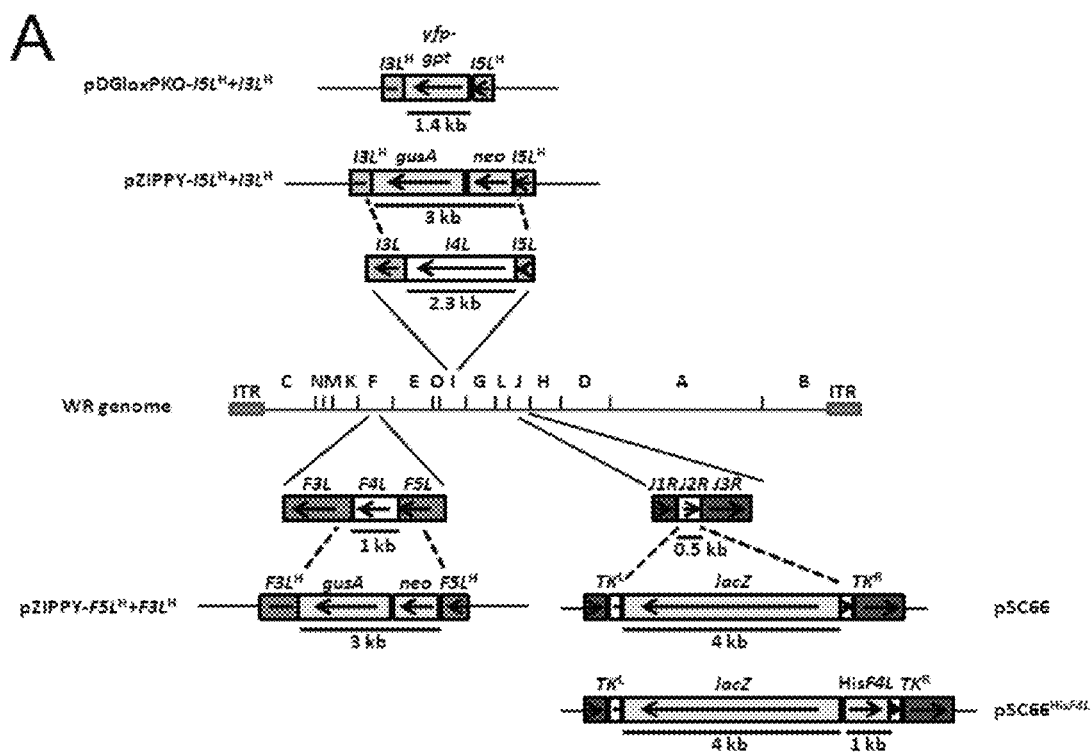
Figure 1:
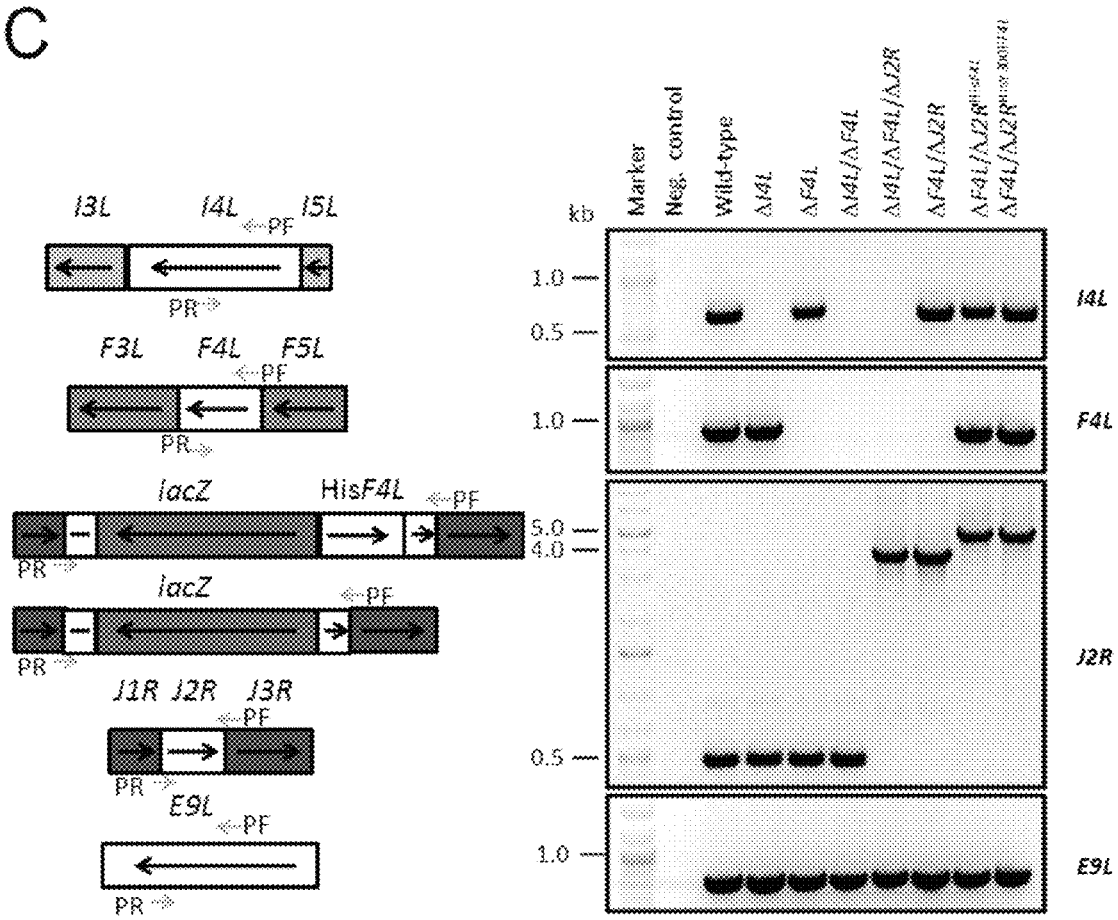
Figure 1:
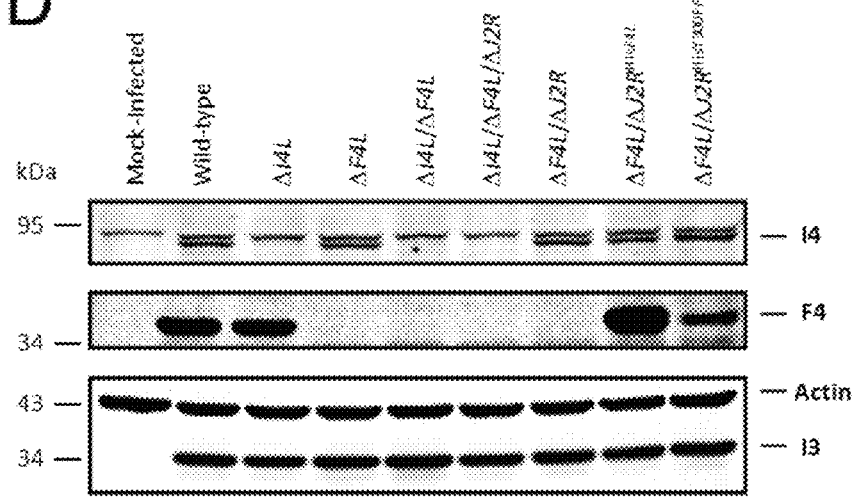

Cihlar et al. "Identification of enzymes catalyzing two-step phosphorylation of cidofovir and the effect of cytomegalovirus infection on their activities in host cells." Mol Pharmacol, 1996, vol. 50, pp. 1502-1510.
Cresawn et al. "Mapping and phenotypic analysis of spontaneous isatin-betathiosemicarbazone resistant mutants of vaccinia virus." Virology, 2007, vol. 363, pp. 319-332.
Davidson et al. "An increase in the expression of ribonucleotide reductase large subunit 1 is associated with gemcitabine resistance in non-small cell lung cancer cell lines." Cancer Res., 2004, vol. 61, No. 11, pp. 3761-3766.
Duxbury et al. "Retrovirally mediated RNA interference targeting the M2 subunit of ribonucleotide reductase: A novel therapeutic strategy in pancreatic cancer." Surgery, 2004, vol. 136, pp. 261-269.
Duxbury et al. "RNA interference targeting the M2 subunit of ribonucleotide reductase enhances pancreatic adenocarcinoma chemosensitivity to gemcitabine." Oncogene, 2004, vol. 23, pp. 1539-1548.
Dvoracek et al. "Construction of a novel set of transfer vectors to study vaccinia virus replication and foreign gene expression." Plasmid, 2003, vol. 49, No. 1, pp. 9-17.
Engstrom et al. "Cell cycle dependent expression of mammalian ribonucleotide reductase." J. Biol. Chem., 1985, vol. 260, pp. 9114-9116.
Engstrom et al. "Immunocytochemical evidence for the cytoplasmic localization and differential expression during the cell cycle of the M1 and M2 subunits of mammalian ribonucleotide reductase." EMBO. J., 1988, vol. 7, pp. 1615-1620.
Engstrom et al. "Localization of ribonucleotide reducase in mammalian cells." EMBO. J. 1984. vol. 3, pp. 863-867.
Fang et al. "Host range, growth property, and virulence of the smallpox vaccine: vaccinia virus Tian Tan strain." Virology, 2005, vol. 335, pp. 242-251.
Furuta et al. "Metabolic genes in cancer: their roles in tumor progression and clinical implications." Biochim. Biophys. Acta., 2010, vol. 1805, No. 2, pp. 141-152.
Gammon et al. "Vaccinia virus-encoded ribonucleotide reductase subunits are differentially required for replication and pathogenesis." PLoS Pathog, 2010, vol. 6, No. 7, pp. 1-20.
Horig et al. "Phase I clinical trial of a recombinant canarypoxvirus (ALVAC) vaccine expressing human carcinoembryonic antigen and the B7.1 co-stimulatory molecule." Cancer Immunol Immunother, 2000, vol. 49, pp. 504-514.
Howell et al. "Vaccinia virus ribonucleotide reductase: correlation between deoxyribonucleotide supply and demand." J. Biol. Chem., 1993, vol. 268, No. 10, pp. 7155-7162.
Hu et al. "Yaba-like disease virus: an alternative replicating poxvirus vector for cancer gene therapy." J Virol, 2001, vol. 75, pp. 10300-10308.
Huse et al. "Generation of Large Combinatorian Library of the Immonuglobulin Repertoire in Phage Lambda." Science, 1989, vol. 246, p. 1275.
Iwaki et al. "A small interfering RNA targeting proteinase-activated receptor-2 is effective in suppression of tumor growth in a Panc1 xenograft model." Int J Cancer, 2008, vol. 122, pp. 658-663.
Jin et al. "Characterization of the complete genomic sequence of the vaccinia virus Tian Tian strain." Sci. China, 1997, vol. 27, pp. 562-567.
Kaufman et al. "Combination chemotherapy and ALVAC-CEA/B7.1 vaccine in patients with metastatic colorectal cancer." Clin Cancer Res, 2008, vol. 14, pp. 4843-4849.
Kern et al. "Activities of certain 5-substituted 4'-thiopyrimidine nucleosides against orthopoxvirus infections." Antimicrob Agents Chemother, 2009, vol. 53, pp. 572-579.
Kholer et al. "Continuous Cultures of Fused Cells Secreting Antibody of Predefined Specificity." Nature, 1975, vol. 256, pp. 495-497.
Kitamoto et al. "Preparation of monoclonal antibodies cross-reactive with orthopox viruses and their application for direct immunofluorescence test." Microbio. Immunol., 2005, vol. 49, No. 3, pp. 219-225.
Kolesar et al. "Evaluation of mRNA by Q-RTPCR and proein expression by AQUA of the M2 subunit of ribonucleotide reductase (RRM2) in human tumors." Cancer Chemotherapy and Pharmacology, 2008, vol. 64, No. 1, pp. 79-86.
Lee et al. "GTI-2040, an Antisense Agent Targeting the Small Subunit Component (R2) of Human Ribonucleotide Reductase, Shows Potent Antitumor Activity against a Variety of Tumors." Cancer Research, 2003, vol. 63, pp. 2802-2811.
Lee et al. "Molecular attenuation of vaccinia virus: mutant generation and animal characterization." J Virol, 1992, vol. 66, pp. 2617-2630.
Lin et al. "Vaccinia virus DNA ligase recruits cellular topoisomerase II to sites of viral replication and assembly." J Virol, 2008, vol. 82, pp. 5922-5932.
Magee et al. "Cidofovir and (S)-9-[3-hydroxy-(2-phosphonomethoxy)propyl]adenine are highly effective inhibitors of vaccinia virus DNA polymerase when incorporated into the template strand." Antimicrob Agents Chemother, 2008, vol. 52, pp. 586-597.
Magee et al. "Mechanism of inhibition of vaccinia virus DNA polymerase by cidofovir diphosphate." Antimicrob Agents Chemother, 2005, vol. 49, pp. 3153-3162.
Manual, B. C. A. C. D. 2006. Hydroxyurea Information Sheet, retrieved from (http://www.bccancer.bc.ca/NR/rdonlyres/D83AB234-30D8-4489-B4DE-41FAA5B81743/19225/Hydroxyureamonograph-1Dec06.pdf).
McLeod et al. "Multicellular tumor spheroids grown from pancreatic carcinoma cell lines: use as an orthotopic xenograft in athymic nude mice." Pancreas, 1997, vol. 14, pp. 237-248.
Nordlund et al. "Ribonucleotide Reductases." Annu. Rev. Biochem., 2006, vol. 75, pp. 681-706.
Pontarin et al. "Ribonucleotide reduction is a cytosolic process in mammalian cells independently of DNA damage." Proc Natl Acad Sci U S A, 2008, vol. 105, pp. 17801-17806.
Prichard et al. "Selective phosphorylation of antiviral drugs by vaccinia virus thymidine kinase." Antimicrob Agents Chemother, 2007, vol. 51, pp. 1795-1803.
Roder et al. "The EBV-Hybridoma Technique." Methods in Enzymology, 1986, vol. 121, pp. 140-167.
Rosell et al. "Gene expression as a predictive marker of outcome in stage IIB-IIIA-IIIB non-small cell lung cancer after induction gemcitabine-based chemotherapy followed by resectional surgery." Clin Cancer Res, 2004, vol. 10, pp. 4215s-4219s.
Roseman et al. "The vaccinia virus HindIII F fragment: nucleotide sequence of the left 6.2 kb." Virology, 1990, vol. 178, pp. 410-418.
Rove et al. "Evidence by multigenesis that Tyr370 of the mouse ribonucleotide reducase R2 protein is he connecting link in the intersubunit radical transfer pathway." J. Biol. Chem., 1999, vol. 274, No. 34, pp. 23746-23751.
Saban et al. "Hydroxyurea and hydroxamic acid derivatives as antitumor drugs." Cancer Chemother Pharmacol, 2009, vol. 64, pp. 213-221.
Skolnick & Fetrow "From genes to protein structure and function: novel applications of computational approaches in the genomic era." Trends in Biotech, 2000, vol. 18, p. 34-39.
Slabaugh et al. "Hydroxyurea-resistant vaccinia virus: overproduction of ribonucleotide reductase." J Virol, 1988, vol. 60, pp. 506-514.
Smallwood et al. "Different Substitutions at Conserved Amino Acids in Domains II and III in the Sendai L RNA Polymerase Protein Inactive Viral RNA Synthesis." Virology, 2002, vol. 304, p. 135-145.
Souglakos et al. "Ribonucleotide reductase subunits M1 and M2 mRNA expression levels and clinical outcome of lung adenocarcinoma patients treated with docetaxel/gemcitabine." Br J Cancer, 2008, vol. 98, pp. 1710-1715.
Stanford et al. "Myxoma virus and oncolytic virotherapy: a new biologic weapon in the war against cancer." Expert Opin Biol Ther, 2007, vol. 7, pp. 1415-1425.
Sunaga et al. "Gene expression of 5-fluorouracil metabolic enzymes in hepatocellular carcinoma and non-tumor tissue." J. Chemother. 2007, vol. 19, pp. 709-715.
Taddie et al. "Genetic characterization of the vaccinia virus DNA polymerase: cytosine arabinoside resistance requires a variable lesion conferring phosphonoacetate resistance in conjunction with an invariant mutation localized to the 3'-5' exonuclease domain." J Virol, 1993, vol. 67, pp. 4323-4336.

(56) References Cited

OTHER PUBLICATIONS

Tomasinsig & Zanetti "The Cathelicidins—Structure, Function and Evolution" Current Protein and Peptide Science, 2005, vol. 6, p. 23-34.

Tulman et al. "Genome of horsepoxvirus." J Virol, 2006, vol. 80, pp. 9244-9258.

Wang et al. "Regulation of p53R2 and its role as potential target for cancer therapy." Cancer Lett, 2009, vol. 276, pp. 1-7.

Wasilenko et al. "Vaccinia virus encodes a previously uncharacterized mitochondrial-associated inhibitor of apoptosis." Proc Natl Acad Sci U S A, 2003, vol. 100, pp. 14345-14350.

Watanabe et al. "Effects of tumor selective replication-competent herpes viruses in combination with gemcitabine on pancreatic cancer." Cancer Chemother Pharmacol, 2008, vol. 61, pp. 875-882.

Woo et al. "Myxoma virus is oncolytic for human pancreatic adenocarcinoma cells." Ann Surg Oncol, 2008, vol. 15, pp. 2329-2335.

Wright et al. "Altered expression of ribonucleotide reductase and role of M2 gene amplification in hydroxyurea-resistant hamster, mouse, rat, and human cell lines." Somat Cell Mol Genet, 1987, vol. 13, pp. 155-165.

Xiong et al. "Kinetic analysis of the interaction of cidofovir diphosphate with human cytomegalovirus DNA polymerase." Biochem Pharmacol, 1996, vol. 51, pp. 1563-1567.

Xu et al. "Broad overexpression of ribonucleotide reductase genes in mice specifically induces lung neoplasms." Cancer Res. 2008, vol. 68, No. 8, pp. 2652-2660.

Xue et al. "Structurally dependent redox property or ribonucleotide reductase subunit p53R2." Cancer Res., 2006, vol. 66, No. 4, pp. 1900-1905.

Yun et al. "Transcriptional targeting of gene expression in breast cancer by the promoters of protein regulator of cytokinesis 1 and ribonuclease reductase 2." Experimental and Molecular Medicine, 2008, vol. 40, No. 3, pp. 345-353.

\* cited by examiner

Figure 1 (continued)

A

B

A

B

A

B

A

A

B

C

A

B

A

B

SEQUENCE LISTING

<160> NUMBER OF SEQ ID NOS: 28

<210> SEQ ID NO 1
<211> LENGTH: 319
<212> TYPE: PRT
<213> ORGANISM: Vaccinia virus

<400> SEQUENCE: 1

```
Met Glu Pro Ile Leu Ala Pro Asn Pro Asn Arg Phe Val Ile Phe Pro
1               5                   10                  15

Ile Gln Tyr Tyr Asp Ile Trp Asn Met Tyr Lys Lys Ala Glu Ala Ser
            20                  25                  30

Phe Trp Thr Val Glu Glu Val Asp Ile Ser Lys Asp Ile Asn Asp Trp
        35                  40                  45

Asn Lys Leu Thr Pro Asp Glu Lys Tyr Phe Ile Lys His Val Leu Ala
    50                  55                  60

Phe Phe Ala Ala Ser Asp Gly Ile Val Asn Glu Asn Leu Ala Glu Arg
65                  70                  75                  80

Phe Cys Thr Glu Val Gln Ile Thr Glu Ala Arg Cys Phe Tyr Gly Phe
                85                  90                  95

Gln Met Ala Ile Glu Asn Ile His Ser Glu Met Tyr Ser Leu Leu Ile
            100                 105                 110

Asp Thr Tyr Val Lys Asp Ser Asn Glu Lys Asn Tyr Leu Phe Asn Ala
        115                 120                 125

Ile Glu Thr Met Pro Cys Val Lys Lys Lys Ala Asp Trp Ala Gln Lys
    130                 135                 140

Trp Ile His Asp Ser Ala Gly Tyr Gly Glu Arg Leu Ile Ala Phe Ala
145                 150                 155                 160

Ala Val Glu Gly Ile Phe Phe Ser Gly Ser Phe Ala Ser Ile Phe Trp
                165                 170                 175

Leu Lys Lys Arg Gly Leu Met Pro Gly Leu Thr Phe Ser Asn Glu Leu
            180                 185                 190

Ile Ser Arg Asp Glu Gly Leu His Cys Asp Phe Ala Cys Leu Met Phe
        195                 200                 205

Lys His Leu Leu His Pro Pro Ser Glu Glu Thr Val Arg Ser Ile Ile
    210                 215                 220

Thr Asp Ala Val Ser Ile Glu Gln Glu Phe Leu Thr Ala Ala Leu Pro
225                 230                 235                 240
```

```
Val Lys Leu Ile Gly Met Asn Cys Glu Met Met Lys Thr Tyr Ile Glu
            245                 250                 255

Phe Val Ala Asp Arg Leu Ile Ser Glu Leu Gly Phe Lys Lys Ile Tyr
        260                 265                 270

Asn Val Thr Asn Pro Phe Asp Phe Met Glu Asn Ile Ser Leu Glu Gly
        275                 280                 285

Lys Thr Asn Phe Phe Glu Lys Arg Val Gly Glu Tyr Gln Lys Met Gly
    290                 295                 300

Val Met Ser Gln Glu Asp Asn His Phe Ser Leu Asp Val Asp Phe
305                 310                 315

<210> SEQ ID NO 2
<211> LENGTH: 26
<212> TYPE: DNA
<213> ORGANISM: Artificial Sequence
<220> FEATURE:
<223> OTHER INFORMATION: Synthetic construct

<400> SEQUENCE: 2
actagttaga taaatggaaa tatctt                                          26

<210> SEQ ID NO 3
<211> LENGTH: 26
<212> TYPE: DNA
<213> ORGANISM: Artificial Sequence
<220> FEATURE:
<223> OTHER INFORMATION: Synthetic construct

<400> SEQUENCE: 3
aagctttcag ttatctatat gcctgt                                          26

<210> SEQ ID NO 4
<211> LENGTH: 26
<212> TYPE: DNA
<213> ORGANISM: Artificial Sequence
<220> FEATURE:
<223> OTHER INFORMATION: Synthetic construct

<400> SEQUENCE: 4
ccgcggaatc attttctttt agatgt                                          26

<210> SEQ ID NO 5
<211> LENGTH: 26
<212> TYPE: DNA
<213> ORGANISM: Artificial Sequence
<220> FEATURE:
<223> OTHER INFORMATION: Synthetic construct

<400> SEQUENCE: 5
agatcttatg atgtcatctt ccagtt                                          26

<210> SEQ ID NO 6
<211> LENGTH: 35
<212> TYPE: DNA
<213> ORGANISM: Artificial Sequence
<220> FEATURE:
<223> OTHER INFORMATION: Synthetic construct

<400> SEQUENCE: 6
actagtggaa gggtatctat acttatagaa taatc                                35

<210> SEQ ID NO 7
<211> LENGTH: 37
<212> TYPE: DNA
```

```
<213> ORGANISM: Artificial Sequence
<220> FEATURE:
<223> OTHER INFORMATION: Synthetic construct

<400> SEQUENCE: 7
gtcgactttt gttggtgtaa taaaaaaatt atttaac                                  37

<210> SEQ ID NO 8
<211> LENGTH: 32
<212> TYPE: DNA
<213> ORGANISM: Artificial Sequence
<220> FEATURE:
<223> OTHER INFORMATION: Synthetic construct

<400> SEQUENCE: 8
ccgcggggtt aaacaaaaac atttttattc tc                                       32

<210> SEQ ID NO 9
<211> LENGTH: 26
<212> TYPE: DNA
<213> ORGANISM: Artificial Sequence
<220> FEATURE:
<223> OTHER INFORMATION: Synthetic construct

<400> SEQUENCE: 9
agatctgttt agtctctcct tccaac                                              26

<210> SEQ ID NO 10
<211> LENGTH: 47
<212> TYPE: DNA
<213> ORGANISM: Artificial Sequence
<220> FEATURE:
<223> OTHER INFORMATION: Synthetic construct

<400> SEQUENCE: 10
aagcttatgc atcaccatca ccatcacatg gaacccatcc ttgcacc                       47

<210> SEQ ID NO 11
<211> LENGTH: 28
<212> TYPE: DNA
<213> ORGANISM: Artificial Sequence
<220> FEATURE:
<223> OTHER INFORMATION: Synthetic construct

<400> SEQUENCE: 11
gcggccgctt aaaagtcaac atctaaag                                            28

<210> SEQ ID NO 12
<211> LENGTH: 42
<212> TYPE: DNA
<213> ORGANISM: Artificial Sequence
<220> FEATURE:
<223> OTHER INFORMATION: Synthetic construct

<400> SEQUENCE: 12
cgaaaaacgt gtgggtgaat tccaaaaaat gggagttatg tc                            42

<210> SEQ ID NO 13
<211> LENGTH: 42
<212> TYPE: DNA
<213> ORGANISM: Artificial Sequence
<220> FEATURE:
<223> OTHER INFORMATION: Synthetic construct

<400> SEQUENCE: 13
gacataactc ccatttttg gaattcaccc acacgttttt cg                             42
```

<210> SEQ ID NO 14
<211> LENGTH: 33
<212> TYPE: DNA
<213> ORGANISM: Artificial Sequence
<220> FEATURE:
<223> OTHER INFORMATION: Synthetic construct

<400> SEQUENCE: 14
gtcgacatgg actacaagga cgacgatgac aag    33

<210> SEQ ID NO 15
<211> LENGTH: 37
<212> TYPE: DNA
<213> ORGANISM: Artificial Sequence
<220> FEATURE:
<223> OTHER INFORMATION: Synthetic construct

<400> SEQUENCE: 15
gcggccgctt aaccactgca tgatgtacag atttcgg    37

<210> SEQ ID NO 16
<211> LENGTH: 55
<212> TYPE: DNA
<213> ORGANISM: Artificial Sequence
<220> FEATURE:
<223> OTHER INFORMATION: Synthetic construct

<400> SEQUENCE: 16
aagcttatgg actacaagga cgacgatgac aagatgtttg tcattaaacg aaatg    55

<210> SEQ ID NO 17
<211> LENGTH: 37
<212> TYPE: DNA
<213> ORGANISM: Artificial Sequence
<220> FEATURE:
<223> OTHER INFORMATION: Synthetic construct

<400> SEQUENCE: 17
gcggccgctt aaccactgca tgatgtacag atttcgg    37

<210> SEQ ID NO 18
<211> LENGTH: 33
<212> TYPE: DNA
<213> ORGANISM: Artificial Sequence
<220> FEATURE:
<223> OTHER INFORMATION: Synthetic construct

<400> SEQUENCE: 18
gtcgacatgg actacaagga cgacgatgac aag    33

<210> SEQ ID NO 19
<211> LENGTH: 32
<212> TYPE: DNA
<213> ORGANISM: Artificial Sequence
<220> FEATURE:
<223> OTHER INFORMATION: Synthetic construct

<400> SEQUENCE: 19
gcggccgctc aggatccaca catcagacat tc    32

<210> SEQ ID NO 20
<211> LENGTH: 61
<212> TYPE: DNA
<213> ORGANISM: Artificial Sequence
<220> FEATURE:

<223> OTHER INFORMATION: Synthetic construct

<400> SEQUENCE: 20
ccagtgtggt ggatggacta caaggacgac gatgacaaga tgcatgtgat caagcgagat    60
g    61

<210> SEQ ID NO 21
<211> LENGTH: 32
<212> TYPE: DNA
<213> ORGANISM: Artificial Sequence
<220> FEATURE:
<223> OTHER INFORMATION: Synthetic construct

<400> SEQUENCE: 21
gcggccgctc aggatccaca catcagacat tc    32

<210> SEQ ID NO 22
<211> LENGTH: 48
<212> TYPE: DNA
<213> ORGANISM: Artificial Sequence
<220> FEATURE:
<223> OTHER INFORMATION: Synthetic construct

<400> SEQUENCE: 22
ggatccatgc atcaccatca ccatcacatg ggggacccgg aaaggccg    48

<210> SEQ ID NO 23
<211> LENGTH: 28
<212> TYPE: DNA
<213> ORGANISM: Artificial Sequence
<220> FEATURE:
<223> OTHER INFORMATION: Synthetic construct

<400> SEQUENCE: 23
gcggccgctt aaaaatctgc atccaagg    28

<210> SEQ ID NO 24
<211> LENGTH: 389
<212> TYPE: PRT
<213> ORGANISM: Homo sapiens

<400> SEQUENCE: 24

Met Leu Ser Leu Arg Val Pro Leu Ala Pro Ile Thr Asp Pro Gln Gln
1               5                   10                  15

Leu Gln Leu Ser Pro Leu Lys Gly Leu Ser Leu Val Asp Lys Glu Asn
                20                  25                  30

Thr Pro Pro Ala Leu Ser Gly Thr Arg Val Leu Ala Ser Lys Thr Ala
            35                  40                  45

Arg Arg Ile Phe Gln Glu Pro Thr Glu Pro Lys Thr Lys Ala Ala Ala
        50                  55                  60

Pro Gly Val Glu Asp Glu Pro Leu Leu Arg Glu Asn Pro Arg Arg Phe
65                  70                  75                  80

Val Ile Phe Pro Ile Glu Tyr His Asp Ile Trp Gln Met Tyr Lys Lys
                85                  90                  95

Ala Glu Ala Ser Phe Trp Thr Ala Glu Glu Val Asp Leu Ser Lys Asp
                100                 105                 110

Ile Gln His Trp Glu Ser Leu Lys Pro Glu Glu Arg Tyr Phe Ile Ser
        115                 120                 125

His Val Leu Ala Phe Phe Ala Ala Ser Asp Gly Ile Val Asn Glu Asn
    130                 135                 140

```
Leu Val Glu Arg Phe Ser Gln Glu Val Gln Ile Thr Glu Ala Arg Cys
145                 150                 155                 160

Phe Tyr Gly Phe Gln Ile Ala Met Glu Asn Ile His Ser Glu Met Tyr
            165                 170                 175

Ser Leu Leu Ile Asp Thr Tyr Ile Lys Asp Pro Lys Glu Arg Glu Phe
            180                 185                 190

Leu Phe Asn Ala Ile Glu Thr Met Pro Cys Val Lys Lys Lys Ala Asp
            195                 200                 205

Trp Ala Leu Arg Trp Ile Gly Asp Lys Glu Ala Thr Tyr Gly Glu Arg
            210                 215                 220

Val Val Ala Phe Ala Ala Val Glu Gly Ile Phe Phe Ser Gly Ser Phe
225                 230                 235                 240

Ala Ser Ile Phe Trp Leu Lys Lys Arg Gly Leu Met Pro Gly Leu Thr
            245                 250                 255

Phe Ser Asn Glu Leu Ile Ser Arg Asp Glu Gly Leu His Cys Asp Phe
            260                 265                 270

Ala Cys Leu Met Phe Lys His Leu Val His Lys Pro Ser Glu Glu Arg
            275                 280                 285

Val Arg Glu Ile Ile Ile Asn Ala Val Arg Ile Glu Gln Glu Phe Leu
            290                 295                 300

Thr Glu Ala Leu Pro Val Lys Leu Ile Gly Met Asn Cys Thr Leu Met
305                 310                 315                 320

Lys Gln Tyr Ile Glu Phe Val Ala Asp Arg Leu Met Leu Glu Leu Gly
            325                 330                 335

Phe Ser Lys Val Phe Arg Val Glu Asn Pro Phe Asp Phe Met Glu Asn
            340                 345                 350

Ile Ser Leu Glu Gly Lys Thr Asn Phe Phe Glu Lys Arg Val Gly Glu
            355                 360                 365

Tyr Gln Arg Met Gly Val Met Ser Ser Pro Thr Glu Asn Ser Phe Thr
            370                 375                 380

Leu Asp Ala Asp Phe
385

<210> SEQ ID NO 25
<211> LENGTH: 390
<212> TYPE: PRT
<213> ORGANISM: Mus musculus

<400> SEQUENCE: 25

Met Leu Ser Val Arg Thr Pro Leu Ala Thr Ile Ala Asp Gln Gln Gln
1               5                   10                  15

Leu Gln Leu Ser Pro Leu Lys Arg Leu Thr Leu Ala Asp Lys Glu Asn
            20                  25                  30

Thr Pro Pro Thr Leu Ser Ser Thr Arg Val Leu Ala Ser Lys Ala Ala
            35                  40                  45

Arg Arg Ile Phe Gln Asp Ser Ala Glu Leu Glu Ser Lys Ala Pro Thr
        50                  55                  60

Asn Pro Ser Val Glu Asp Glu Pro Leu Leu Arg Glu Asn Pro Arg Arg
65                  70                  75                  80

Phe Val Val Phe Pro Ile Glu Tyr His Asp Ile Trp Gln Met Tyr Lys
                85                  90                  95

Lys Ala Glu Ala Ser Phe Trp Thr Ala Glu Glu Val Asp Leu Ser Lys
            100                 105                 110

Asp Ile Gln His Trp Glu Ala Leu Lys Pro Asp Glu Arg His Phe Ile
            115                 120                 125
```

```
Ser His Val Leu Ala Phe Phe Ala Ser Asp Gly Ile Val Asn Glu
130                 135                 140

Asn Leu Val Glu Arg Phe Ser Gln Glu Val Gln Val Thr Glu Ala Arg
145                 150                 155                 160

Cys Phe Tyr Gly Phe Gln Ile Ala Met Glu Asn Ile His Ser Glu Met
                165                 170                 175

Tyr Ser Leu Leu Ile Asp Thr Tyr Ile Lys Asp Pro Lys Glu Arg Glu
            180                 185                 190

Tyr Leu Phe Asn Ala Ile Glu Thr Met Pro Cys Val Lys Lys Lys Ala
        195                 200                 205

Asp Trp Ala Leu Arg Trp Ile Gly Asp Lys Glu Ala Thr Tyr Gly Glu
210                 215                 220

Arg Val Val Ala Phe Ala Val Glu Gly Ile Phe Phe Ser Gly Ser
225                 230                 235                 240

Phe Ala Ser Ile Phe Trp Leu Lys Lys Arg Gly Leu Met Pro Gly Leu
                245                 250                 255

Thr Phe Ser Asn Glu Leu Ile Ser Arg Asp Glu Gly Leu His Cys Asp
            260                 265                 270

Phe Ala Cys Leu Met Phe Lys His Leu Val His Lys Pro Ala Glu Gln
        275                 280                 285

Arg Val Arg Glu Ile Ile Thr Asn Ala Val Arg Ile Glu Gln Glu Phe
290                 295                 300

Leu Thr Glu Ala Leu Pro Val Lys Leu Ile Gly Met Asn Cys Thr Leu
305                 310                 315                 320

Met Lys Gln Tyr Ile Glu Phe Val Ala Asp Arg Leu Met Leu Glu Leu
                325                 330                 335

Gly Phe Asn Lys Ile Phe Arg Val Glu Asn Pro Phe Asp Phe Met Glu
            340                 345                 350

Asn Ile Ser Leu Glu Gly Lys Thr Asn Phe Phe Glu Lys Arg Val Gly
        355                 360                 365

Glu Tyr Gln Arg Met Gly Val Met Ser Asn Ser Thr Glu Asn Ser Phe
370                 375                 380

Thr Leu Asp Ala Asp Phe
385                 390

<210> SEQ ID NO 26
<211> LENGTH: 351
<212> TYPE: PRT
<213> ORGANISM: Homo sapiens

<400> SEQUENCE: 26

Met Gly Asp Pro Glu Arg Pro Glu Ala Ala Gly Leu Asp Gln Asp Glu
1               5                   10                  15

Arg Ser Ser Ser Asp Thr Asn Glu Ser Glu Ile Lys Ser Asn Glu Glu
            20                  25                  30

Pro Leu Leu Arg Lys Ser Arg Arg Phe Val Ile Phe Pro Ile Gln
        35                  40                  45

Tyr Pro Asp Ile Trp Lys Met Tyr Lys Gln Ala Gln Ala Ser Phe Trp
50                  55                  60

Thr Ala Glu Glu Val Asp Leu Ser Lys Asp Leu Pro His Trp Asn Lys
65                  70                  75                  80

Leu Lys Ala Asp Glu Lys Tyr Phe Ile Ser His Ile Leu Ala Phe Phe
                85                  90                  95

Ala Ala Ser Asp Gly Ile Val Asn Glu Asn Leu Val Glu Arg Phe Ser
```

```
            100                 105                 110
Gln Glu Val Gln Val Pro Glu Ala Arg Cys Phe Tyr Gly Phe Gln Ile
            115                 120                 125

Leu Ile Glu Asn Val His Ser Glu Met Tyr Ser Leu Leu Ile Asp Thr
        130                 135                 140

Tyr Ile Arg Asp Pro Lys Lys Arg Glu Phe Leu Phe Asn Ala Ile Glu
145                 150                 155                 160

Thr Met Pro Tyr Val Lys Lys Ala Asp Trp Ala Leu Arg Trp Ile
                    165                 170                 175

Ala Asp Arg Lys Ser Thr Phe Gly Arg Val Val Ala Phe Ala Ala
                180                 185                 190

Val Glu Gly Val Phe Phe Ser Gly Ser Phe Ala Ala Ile Phe Trp Leu
            195                 200                 205

Lys Lys Arg Gly Leu Met Pro Gly Leu Thr Phe Ser Asn Glu Leu Ile
        210                 215                 220

Ser Arg Asp Glu Gly Leu His Cys Asp Phe Ala Cys Leu Met Phe Gln
225                 230                 235                 240

Tyr Leu Val Asn Lys Pro Ser Glu Glu Arg Val Arg Glu Ile Ile Val
                    245                 250                 255

Asp Ala Val Lys Ile Glu Gln Glu Phe Leu Thr Glu Ala Leu Pro Val
                260                 265                 270

Gly Leu Ile Gly Met Asn Cys Ile Leu Met Lys Gln Tyr Ile Glu Phe
            275                 280                 285

Val Ala Asp Arg Leu Leu Val Glu Leu Gly Phe Ser Lys Val Phe Gln
        290                 295                 300

Ala Glu Asn Pro Phe Asp Phe Met Glu Asn Ile Ser Leu Glu Gly Lys
305                 310                 315                 320

Thr Asn Phe Phe Glu Lys Arg Val Ser Glu Tyr Gln Arg Phe Ala Val
                    325                 330                 335

Met Ala Glu Thr Thr Asp Asn Val Phe Thr Leu Asp Ala Asp Phe
                340                 345                 350

<210> SEQ ID NO 27
<211> LENGTH: 351
<212> TYPE: PRT
<213> ORGANISM: Mus musculus

<400> SEQUENCE: 27

Met Gly Asp Pro Glu Arg Pro Glu Ala Ala Arg Pro Glu Lys Gly Glu
1               5                   10                  15

Gln Leu Cys Ser Glu Thr Glu Glu Asn Val Val Arg Ser Asn Glu Glu
            20                  25                  30

Pro Leu Leu Arg Lys Ser Ser Arg Arg Phe Val Ile Phe Pro Ile Gln
        35                  40                  45

Tyr Pro Asp Ile Trp Arg Met Tyr Lys Gln Ala Gln Ala Ser Phe Trp
50                  55                  60

Thr Ala Glu Glu Val Asp Leu Ser Lys Asp Leu Pro His Trp Asn Lys
65                  70                  75                  80

Leu Lys Ser Asp Glu Lys Tyr Phe Ile Ser His Ile Leu Ala Phe Phe
                85                  90                  95

Ala Ala Ser Asp Gly Ile Val Asn Glu Asn Leu Val Glu Arg Phe Ser
            100                 105                 110

Gln Glu Val Gln Val Pro Glu Ala Arg Cys Phe Tyr Gly Phe Gln Ile
        115                 120                 125
```

```
Leu Ile Glu Asn Val His Ser Glu Met Tyr Ser Leu Leu Ile Asp Thr
130                 135                 140

Tyr Ile Arg Asp Pro Lys Lys Arg Glu Phe Leu Phe Asn Ala Ile Glu
145                 150                 155                 160

Thr Met Pro Tyr Val Lys Lys Lys Ala Asp Trp Ala Leu Arg Trp Ile
                165                 170                 175

Ala Asp Arg Lys Ser Thr Phe Gly Glu Arg Val Val Ala Phe Ala Ala
            180                 185                 190

Val Glu Gly Ile Phe Phe Ser Gly Ser Phe Ala Ala Ile Phe Trp Leu
        195                 200                 205

Lys Lys Arg Gly Leu Met Pro Gly Leu Thr Phe Ser Asn Glu Leu Ile
210                 215                 220

Ser Arg Asp Glu Gly Leu His Cys Asp Phe Ala Cys Leu Met Phe Gln
225                 230                 235                 240

Tyr Leu Val Asn Lys Pro Ser Glu Asp Arg Val Arg Glu Ile Ile Ala
                245                 250                 255

Asp Ala Val Gln Ile Glu Gln Glu Phe Leu Thr Glu Ala Leu Pro Val
            260                 265                 270

Gly Leu Ile Gly Met Asn Cys Val Leu Met Lys Gln Tyr Ile Glu Phe
        275                 280                 285

Val Ala Asp Arg Leu Leu Gly Glu Leu Gly Phe Ser Lys Ile Phe Gln
290                 295                 300

Ala Glu Asn Pro Phe Asp Phe Met Glu Asn Ile Ser Leu Glu Gly Lys
305                 310                 315                 320

Thr Asn Phe Phe Glu Lys Arg Val Ser Glu Tyr Gln Arg Phe Ala Val
                325                 330                 335

Met Ala Glu Thr Thr Asp Asn Val Phe Thr Leu Asp Ala Asp Phe
            340                 345                 350

<210> SEQ ID NO 28
<211> LENGTH: 319
<212> TYPE: PRT
<213> ORGANISM: Vaccinia virus

<400> SEQUENCE: 28

Met Glu Pro Ile Leu Ala Pro Asn Pro Asn Arg Phe Val Ile Phe Pro
1               5                   10                  15

Ile Gln Tyr Tyr Asp Ile Trp Asn Met Tyr Lys Lys Ala Glu Ala Ser
            20                  25                  30

Phe Trp Thr Val Glu Glu Val Asp Ile Ser Lys Asp Ile Asn Asp Trp
        35                  40                  45

Asn Lys Leu Thr Pro Asp Glu Lys Tyr Phe Ile Lys His Val Leu Ala
50                  55                  60

Phe Phe Ala Ala Ser Asp Gly Ile Val Asn Glu Asn Leu Ala Glu Arg
65                  70                  75                  80

Phe Cys Thr Glu Val Gln Ile Thr Glu Ala Arg Cys Phe Tyr Gly Phe
                85                  90                  95

Gln Met Ala Ile Glu Asn Ile His Ser Glu Met Tyr Ser Leu Leu Ile
            100                 105                 110

Asp Thr Tyr Val Lys Asp Ser Asn Glu Lys Asn Tyr Leu Phe Asn Ala
        115                 120                 125

Ile Glu Thr Met Pro Cys Val Lys Lys Ala Asp Trp Ala Gln Lys
130                 135                 140

Trp Ile His Asp Ser Ala Gly Tyr Gly Glu Arg Leu Ile Ala Phe Ala
145                 150                 155                 160
```

```
Ala Val Glu Gly Ile Phe Phe Ser Gly Ser Phe Ala Ser Ile Phe Trp
            165                 170                 175

Leu Lys Lys Arg Gly Leu Met Pro Gly Leu Thr Phe Ser Asn Glu Leu
            180                 185                 190

Ile Ser Arg Asp Glu Gly Leu His Cys Asp Phe Ala Cys Leu Met Phe
            195                 200                 205

Lys His Leu Leu His Pro Pro Ser Glu Glu Thr Val Arg Ser Ile Ile
        210                 215                 220

Thr Asp Ala Val Ser Ile Glu Gln Glu Phe Leu Thr Ala Ala Leu Pro
225                 230                 235                 240

Val Lys Leu Ile Gly Met Asn Cys Glu Met Met Lys Thr Tyr Ile Glu
                245                 250                 255

Phe Val Ala Asp Arg Leu Ile Ser Glu Leu Gly Phe Lys Lys Ile Tyr
                260                 265                 270

Asn Val Thr Asn Pro Phe Asp Phe Met Glu Asn Ile Ser Leu Glu Gly
            275                 280                 285

Lys Thr Asn Phe Phe Glu Lys Arg Val Gly Glu Tyr Gln Lys Met Gly
            290                 295                 300

Val Met Ser Gln Glu Asp Asn His Phe Ser Leu Asp Val Asp Phe
305                 310                 315
```

ONCOLYTIC VIRUSES AND METHODS FOR TREATING NEOPLASTIC DISORDERS

RELATED APPLICATIONS

This application is a continuation application of U.S. patent application Ser. No. 13/383,396 filed on Jan. 10, 2012, issued as U.S. Pat. No. 8,679,509 on Mar. 25, 2014, which application is a National Stage application of PCT application No. PCT/CA2010/001065 that claims priority of co-pending U.S. Provisional Patent Application No. 61/224,694 filed Jul. 10, 2009, and Canadian Application (serial number 2709292) filed Jul. 8, 2010, all of which are herein incorporated in their entirety by reference.

FIELD

The disclosure pertains to oncolytic viruses, vector constructs and compositions as well as methods for treating neoplastic disorders and more specifically to poxviruses comprising a functionally inactivated R2 gene and methods for treating cancers with increased levels of cellular R2.

BACKGROUND

Ribonucleotide reductases (RR) are evolutionarily conserved enzymes that catalyze the reduction of ribonucleotide diphosphates (rNDPs) to deoxyribonucleotide diphosphates (dNDPs), which is critical in the production and maintenance of dNTP pools. Orthopoxviruses encode genes for both large (~90 kDa) and small (~40 kDa) RR subunits, and homodimers of large and small subunits interact to form a functional RR complex.

Studies of vaccinia RR proteins found that insertional inactivation of I4L in strain WR did not cause observable defects in replication in culture and only mildly-attenuated these viruses in mouse models with an approximate 10-fold increase in lethal dose 50 values for this ΔI4L strain compared to wild-type virus (6). Lee et al. (23) reported a deletion mutant of 180 bp in the NYCBH and Wyeth strains of vaccinia although the specific sites of this deletion within the F4L (or R2) gene are not reported. These authors report that when the growth of this mutant was assessed in BSC-40 cells at a multiplicity of infection (MOI) of 10, this deletion mutant replicated with similar kinetics and yields to the parental (wild-type) strain although the actual quantitative data are not reported by the authors (23). These authors also report that this deletion mutant replicated to similar titers in mouse skin (23).

Vaccinia and other poxviruses have been used clinically. For example vaccinia virus has been used as a vaccine for smallpox. In addition, vaccinia virus has been investigated as an oncolytic virus for cancer therapy.

SUMMARY

As disclosed herein, a series of vaccinia virus (VACV) strains comprising functionally inactivated small RR subunit (F4, also referred to as R2), for example lacking the small RR subunit or comprising a point mutation reducing and/or ablating RR activity, alone or in combination with other functional inactivations, were generated and isolated. Mutants comprising functionally inactivated R2 replicated more poorly than wild-type virus in growth curve experiments but the degree of the replication defects observed were dependent upon the cell lines tested. R2 mutants also displayed severely reduced genome replication abilities compared to wild-type virus. It is also demonstrated herein that vaccinia viruses comprising a functionally inactivated R2 gene, alone or in combination with functionally inactivated R1 and/or J2R genes, preferentially replicate and induce death in cancer cells having increased RR levels. Such viruses are useful for treating neoplastic disorders, for example cancers, with increased RR levels.

Accordingly, in an aspect, the disclosure provides an isolated poxvirus, optionally a recombinant poxvirus, comprising a functionally inactivated R2 gene. In an embodiment, the isolated or recombinant virus replicates more efficiently in cells with increased levels of RR, such as neoplastic disorder cells. In another embodiment, the isolated or recombinant virus replicates more efficiently in neoplastic disorder cells than in wild-type cells. In another embodiment, the isolated or recombinant virus is not a NYCBH vaccinia virus or a Wyeth vaccine strain comprising a deletion of 180 base pairs of R2 gene.

In an embodiment, the functionally inactivated R2 gene comprises a dominant negative mutation, a point mutation or a deletion mutation, wherein the encoded protein of the deletion mutation lacks at least 2 amino acids, or at least 7 amino acids, for example all or part of the R1 binding domain. In a further embodiment, the encoded protein lacks at least 61 amino acids. In another embodiment, the protein encoded by the functionally inactive R2 gene is capable of interacting with cellular RR subunits. In still another embodiment, the deleted amino acids comprise deletion of at least one catalytically important residue and/or the R1 binding site, for example as provided in FIG. 1B. In another embodiment, the functionally inactivated R2 comprises a Y300 mutation, such as a Y300F mutation, and/or any mutation of one or more of the following residues which causes loss or reduction of catalytic activity: W34, E38, D70, E101, H104, Y108, F167, F171, G181, I193, D196, E197, H200, Y254, and E294. The foregoing mutations are provided in relation to the sequence of SEQ ID NO:1. A person skilled in the art using for example sequence alignment software, would readily be able to identify the corresponding positions in any other R2 polypeptide.

In an embodiment, the poxvirus is a genus or strain that natively comprises a R2 gene and is infectious for mammalian cells. In another embodiment, the poxvirus is infectious for human cells. In another embodiment, the poxvirus is infectious for human tumor cells.

In an embodiment, the poxvirus is selected from a genus in Table 3, optionally an Orthopoxvirus such as a vaccinia virus, a Leporipoxvirus, a Suipoxvirus, a Capripoxvirus, a Cervidpoxvirus, an Avipoxyiurs, a Molluscipoxvirus, a Parapoxvirus and a Yatapoxvirus. In another embodiment, the poxvirus is unclassified, for example a crocodilepox virus (CRV). In another embodiment, the poxvirus is vaccinia virus. In yet another embodiment, the vaccinia virus is a vaccinia virus strain selected from a WR (Genbank accession: NC 006998), Tian Tian (AF095689.1), NYCBH, Wyeth, Copenhagen (M35027), Lister (AY678276), MVA (U94848), Lederle, Temple of Heaven, Tashkent, USSR, Evans, Praha, LIVP, Ikeda, IHD, Dls, LC16 (AY678275), EM-63, IC, Malbrán, DUKE (DQ439815), Acambis (AY313847), 3737 (DQ377945), CVA (AM501482) and AS each of the foregoing incorporated herein by reference.

In an embodiment, the functionally inactivated R2 gene of vaccinia virus encodes a protein that is deleted for at least 2 amino acid residues, optionally deleted for 2 amino acids of SEQ ID NO:1. In another embodiment, the deletion mutant lacks at least 7 amino acids, optionally the RR1 binding domain. In a further embodiment, the deletion mutant lacks at least 310 amino acid residues, or optionally lacks amino acid residues 1 to 310. In an embodiment, the nucleotides corresponding to nucleotides 33948-32987 of WR genome are deleted. In an embodiment, the poxvirus comprises a mutation described in Tables 1 or 2.

In an embodiment, the isolated or recombinant virus further comprises a functionally inactivated R1 gene, thymidine kinase gene and/or vaccinia virus growth factor gene.

In another aspect, the disclosure provides a composition comprising the isolated optionally recombinant virus disclosed herein and a pharmaceutically acceptable diluent or carrier. In an embodiment, the composition further comprises hydroxyurea, gemcitabine and/or a nucleoside analog.

In another aspect, the disclosure provides a method of inducing death in a neoplastic disorder cell, the method comprising contacting the cell with an isolated or recombinant virus or composition of the disclosure. In an embodiment, the cell is in vivo.

In a further aspect, the disclosure provides a method of treating a neoplastic disorder comprising administering an effective amount of the isolated or recombinant virus or composition disclosed herein to a subject in need thereof. In an embodiment, the virus is an oncolytic virus. In another embodiment, the neoplastic disorder is cancer. In yet another embodiment, the cancer is selected from breast cancer, lung cancer, colorectal cancer, hepatic cancer such as hepatocellular carcinoma, pancreatic cancer, skin cancer such as melanoma, esophageal cancer, leukemia, ovarian cancer, head and neck cancer, gliomas and gastric cancer. In an embodiment, the cancer is a carcinoma. In another embodiment, the cancer is an epitheliod carcinoma. In an embodiment, the cancer is a cancer type described in Table 4.

In another embodiment, the subject has been previously treated with hydroxyurea and/or gemcitabine. In an embodiment, the cancer cell or cancer is resistant to chemotherapy. In another embodiment the cancer cell or cancer is resistant to hydroxyurea or gemcitabine.

In an embodiment, the cancer cell or cancer comprises increased levels of ribonucleotide reductase compared to a normal cell of the same tissue type. In another embodiment, the level of ribonucleotide reductase is assessed by determining the activity level of the ribonucleotide reductase, the protein level of the ribonucleotide reductase, the RNA level of the ribonucleotide reductase or the levels of dNTPs, wherein an increase in the activity, protein, or RNA level of ribonucleotide reductase or an increase in the levels of dNTPS is indicative that the cancer cell or cancer has increased levels of ribonucleotide reductase. In still another embodiment, the level of ribonucleotide reductase is at least 10% more compared to a normal cell of the same tissue type.

In an embodiment, the cancer cell or a sample of the subject's cancer is assessed for ribonucleotide reductase levels prior to administration of the isolated or recombinant virus or composition of the disclosure. In another embodiment, the subject is also administered hydroxyurea wherein the hydroxyurea is administered prior to, contemporaneously with, or following administration of the isolated or recombinant virus or composition of the disclosure.

In an embodiment, the subject is also administered a nucleoside analog, wherein the nucleoside analog is administered prior to, contemporaneously with, or following administration of the isolated or recombinant virus and/or composition disclosed herein. In an embodiment, the subject is also administered gemcitabine wherein the gemcitabine is administered prior to, contemporaneously with, or following administration of the isolated recombinant virus or composition disclosed herein. In an embodiment, the nucleoside analog is cidofovir (CDV) and/or any other acyclic nucleoside phosphonate compound and/or alkoxy ester derivative there of.

In another aspect, the disclosure provides use of an isolated and/or recombinant virus or a composition disclosed herein to induce death in a cancer cell or to treat cancer.

A further aspect includes an isolated poxvirus comprising a functionally inactivated R2 gene or a composition comprising the isolated poxvirus for use in inducing death in a neoplastic disorder cell and/or for use in treating a neoplastic disorder. In an embodiment, the neoplastic disorder comprises an increased level of an RR subunit.

Also provided, in another aspect, is a vector construct for generating a poxvirus with a functionally inactivated R2 comprising:
   a vector backbone;
   a 5' nucleic acid comprising a 5' flanking sequence of a genomic region of a gene to be replaced such as a R2 gene;
   an exchange cassette downstream of the 5' flanking sequence, operably linked to a promoter, the exchange cassette optionally comprising a NEO gene cassette (for example operably linked to a p7.5 promoter), a gusA gene cassette (for example operably linked to a modified H5 promoter) or a mutant gene of the gene to be replaced such as a mutant R2 gene cassette; and
   a 3' nucleic acid comprising 3' flanking sequence of the genomic region of the gene to be replaced such as a R2 gene, downstream of the exchange cassette nucleic acid.

In an embodiment, the gene to be replaced is the R2 gene. In another embodiment, the gene is a R1 gene. In an embodiment, where the gene to be replaced is a R2 gene, the distance between the start of the 5' nucleic acid and the end of the 3' nucleic acid is greater than or less than 180 bp.

In an embodiment, the vector backbone comprises pZIPPY-NEO/GUS (11). In an embodiment, the vector construct is generated using one or more primers from Table 5.

Another aspect includes a method of making an isolated recombinant poxvirus comprising a functionally inactivated R2 gene, comprising constructing a vector construct for generating a poxvirus with functionally inactivated R2 gene described herein; transfecting the vector construct into cells infected with a poxvirus, such as a wild-type poxvirus infected cells, under conditions suitable for recombination; and isolating a recombinant poxvirus functionally inactivated for R2.

In a further aspect, the application provides an isolated cell comprising an isolated and/or recombinant poxvirus comprising a functionally inactivated R2 gene.

In a further aspect, the disclosure provides an antibody generated using ectromelia virus R2 antigen that detects ectromelia virus R2 antigen and vaccinia virus F4. In an embodiment, the antibody is monoclonal.

Other features and advantages of the present application will become apparent from the following detailed description. It should be understood, however, that the detailed description and the specific examples while indicating preferred embodiments of the application are given by way of illustration only, since various changes and modifications within the scope of the application will become apparent to those skilled in the art from this detailed description.

BRIEF DESCRIPTION OF THE DRAWINGS

Embodiments of the disclosure will be described in relation to the drawings in which:

FIG. 1: Strategy for the construction of recombinant vaccinia viruses and characterization of mutant strains. A) Vaccinia genome schematic illustrating the relative positions and strategies used for deletion/insertion mutations in F4L, I4L, and J2R (see Materials and Methods for details). B) Alignment of human R2 (HR2; Genbank accession: NP_001025); mouse R2 (MR2 Genbank accession: NP_033130); human p53R2 (Hp53R2; Genbank accession: BAD12267); mouse p53R2 (Mp53R2; Genbank accession: Q6PEE3) and vaccinia R2 (VACVR2; Genbank accession: AAO89322) subunits each of the foregoing accession numbers incorporated herein by reference. Adapted from (5). (*) indicates catalytically-important residues and the boxed residues represent the R1 binding domain (5). The alignment was performed with ClustalW software. C) Ethidium bromide-stained agarose gels illustrating PCR analysis of mutant strains. D) Western blot analysis of ribonucleotide reductase mutant strains after infection in HeLa cells (MOI=10) for 8 h. Note that the top band in the I4 blot appears due to cross-reactivity of the anti-I4 antibody with HR1. Blotting for the constitutively-expressed cellular or viral proteins (Actin and I3, respectively) served as loading controls. Accession numbers described herein including the accession numbers listed above are herein incorporated by reference.

Figure 2:
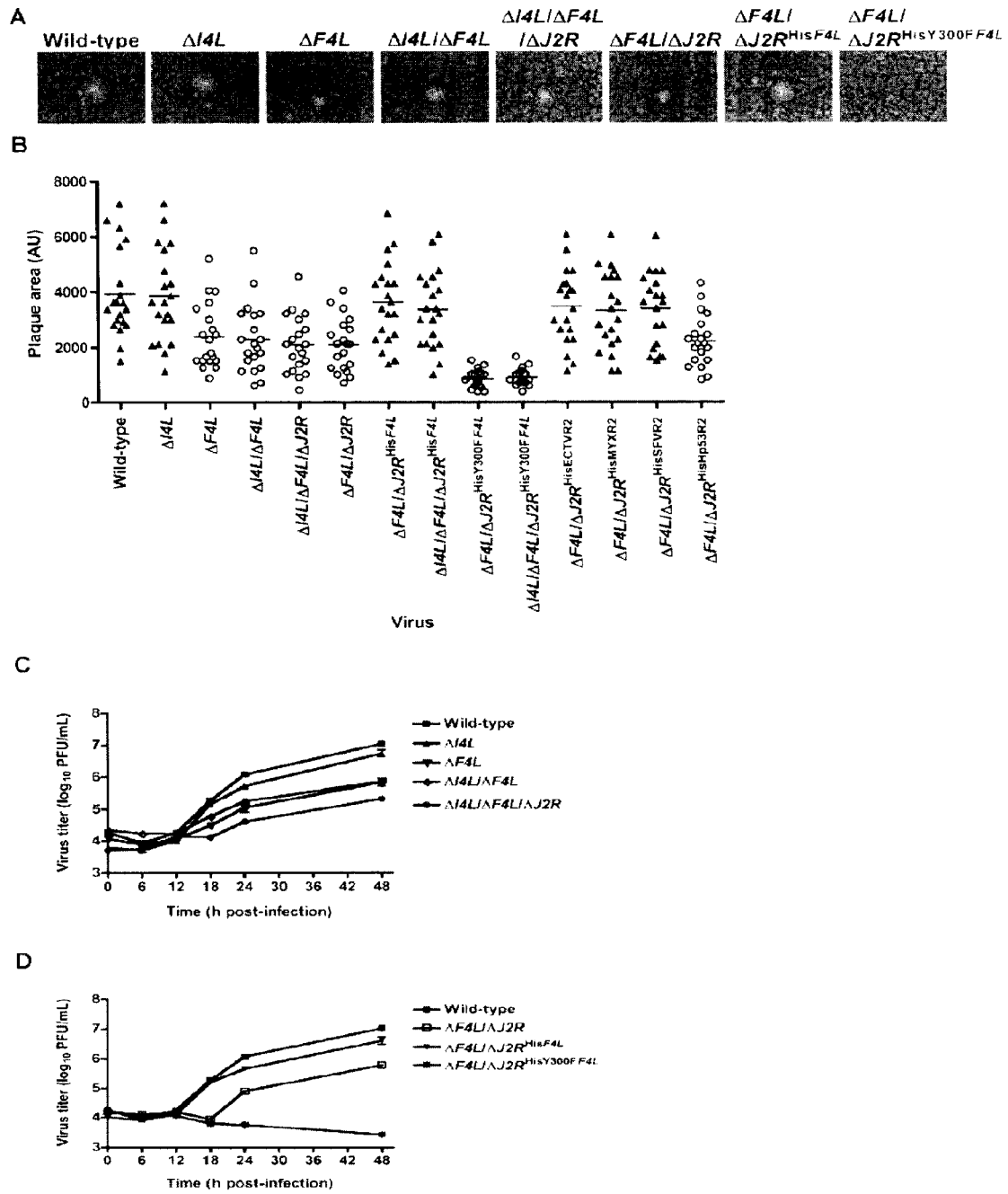

FIG. 2: ΔF4L strains exhibit a small plaque phenotype and impaired replication in vitro. A) Representative plaques formed by each of the indicated strains 48 h post-infection on BSC-40 cells. B) Scatter plots illustrating independent (n=20) as well as mean (horizontal bar) plaque area measurements in arbitrary units (AU) for each of the indicated strains. Open circles indicate that the mean plaque area was statistically different (P<0.05) from wild-type virus based on a one-way ANOVA. C) and D) virus growth in HeLa cells infected with each of the indicated strains at a MOI of 0.03. Viruses were harvested at the indicated time points and tittered on BSC-40 cells. Note that experiments presented in (C) and (D) were done in parallel but are presented in two graphs for clarity. Thus, the wild-type curve is identical in both graphs. Symbols represent mean titers from three independent experiments and error bars represent SE. Some bars are approximately the same size as the symbols.

Figure 3:
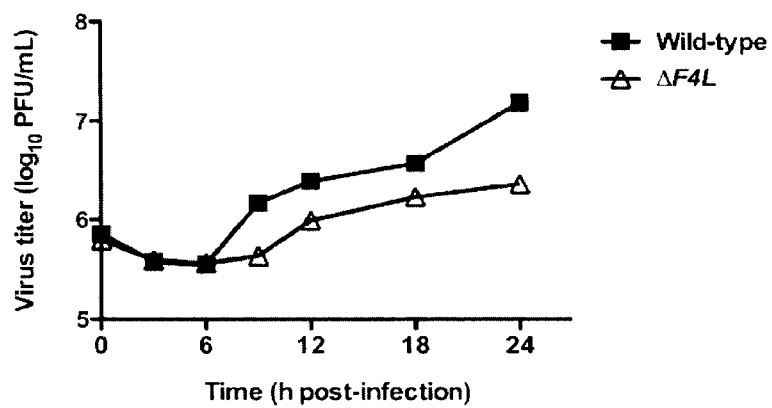
Figure 3:
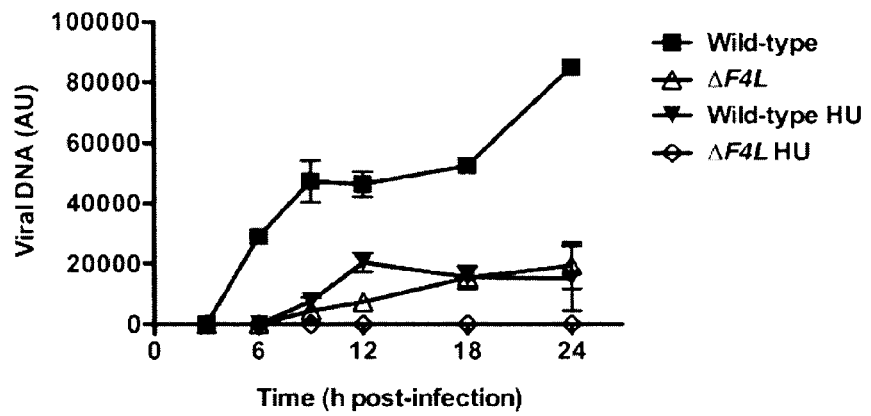

FIG. 3: Growth and genome replication capacities of ΔF4L virus in BSC-40 cells. A) Growth curve (MOI=2) of indicated viruses in BSC-40 cells showing mean (±SE) titers determined at the indicated time points. Note that in some cases the error bars are the same size as the symbols. B) Parallel samples from A) were analyzed for genome replication by radioisotope-based slot-blots of DNA extracts from cells infected with the indicated viruses in the presence or absence of 0.5 mM hydroxyurea (HU) in BSC-40 cells.

Figure 4:
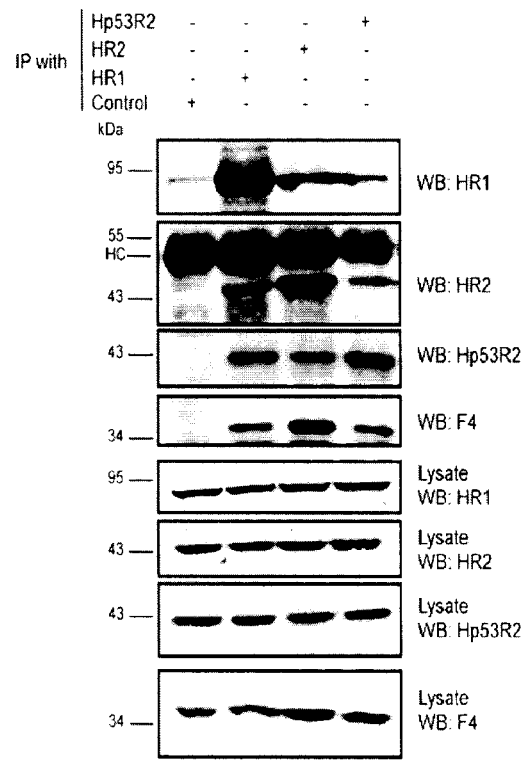
Figure 4:
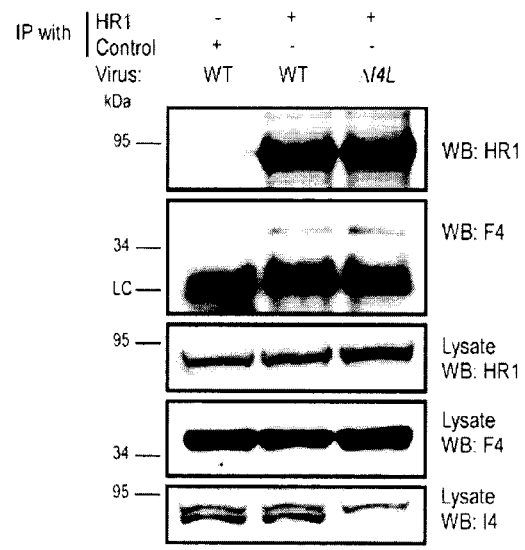

FIG. 4: Co-immunoprecipitation of vaccinia virus F4 with endogenous cellular ribonucleotide reductase (RR) proteins. A) HeLa cells were infected (MOI=10) for 6 h with wild-type vaccinia virus after which harvested cells were lysed, and resulting protein extracts were subject to immunoprecipitation using commercial antibodies recognizing the indicated cellular proteins or normal goat serum (control). B) Co-immunoprecipitation of F4 with HR1 in the presence or absence of I4. HeLa cells were infected with wild-type or ΔI4L VAVC strains as in (A) and subjected to immunoprecipitation with HR1 or control antibodies 8 h post-transfection. These immunoprecipitates and the corresponding whole cell extracts (lysate) were subjected to SDS-PAGE, transferred to a nitrocellulose membrane and western blotted (WB) with antibodies recognizing the indicated cellular or viral proteins.

Figure 5:
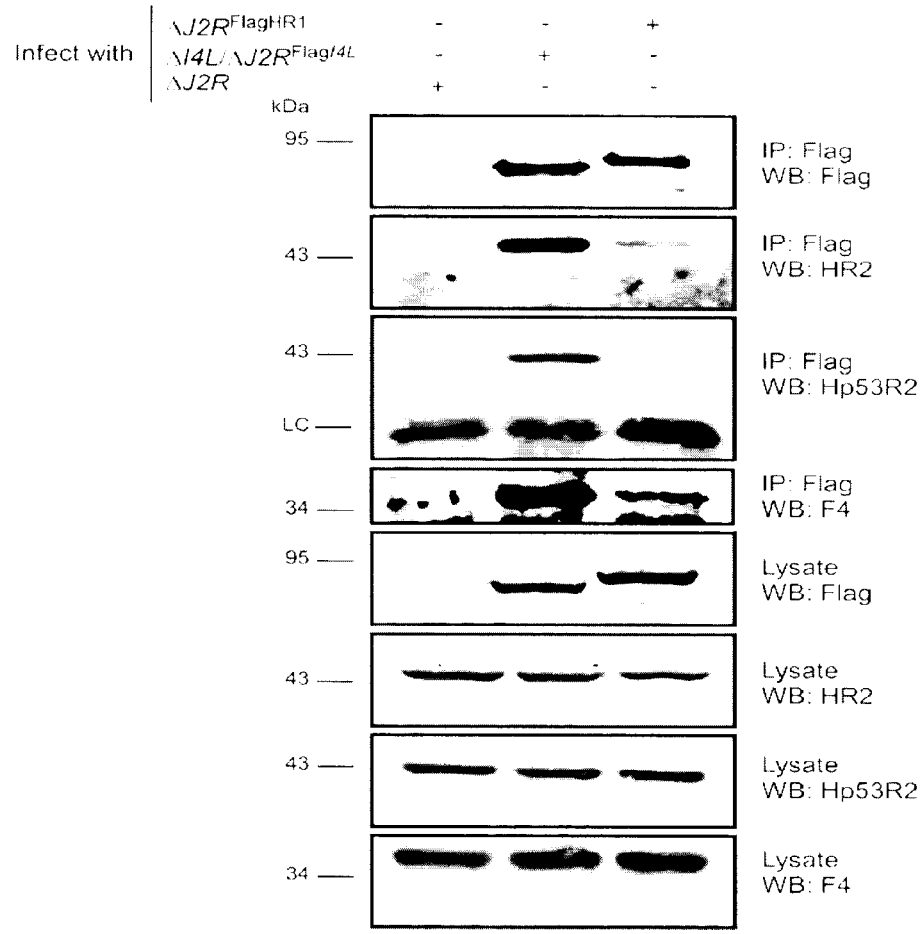
Figure 5:
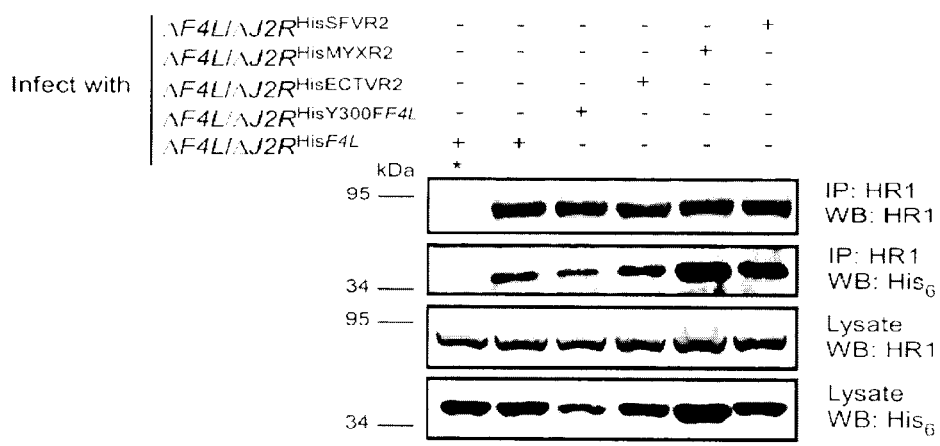

FIG. 5: Recombinant poxvirus RR proteins interact with endogenous human RR proteins. A) Co-immunoprecipitation of Flag-tagged viral/cellular large RR subunits with viral/cellular small RR subunits. HeLa cells were infected (MOI=10) for 8 h with the indicated vaccinia virus strains (see Materials and Methods for descriptions) after which lysates were subjected to immunoprecipitation with an anti-Flag antibody. B) Co-immunoprecipitation of VACV, ectromelia (ECTV), myxoma (MYX) and Shope fibroma (SFV) His$_6$-tagged R2 proteins with HR1. HeLa cells were infected with the indicated strains at a MOI of 10 for 8 h and then protein extracts were subjected to immunoprecipitation with anti-HR1 antibodies or control serum (indicated by "*"). LC, light chain. Immunoprecipitates and the corresponding whole cell extracts were then western blotted as described in the legend of FIG. 4.

Figure 6:
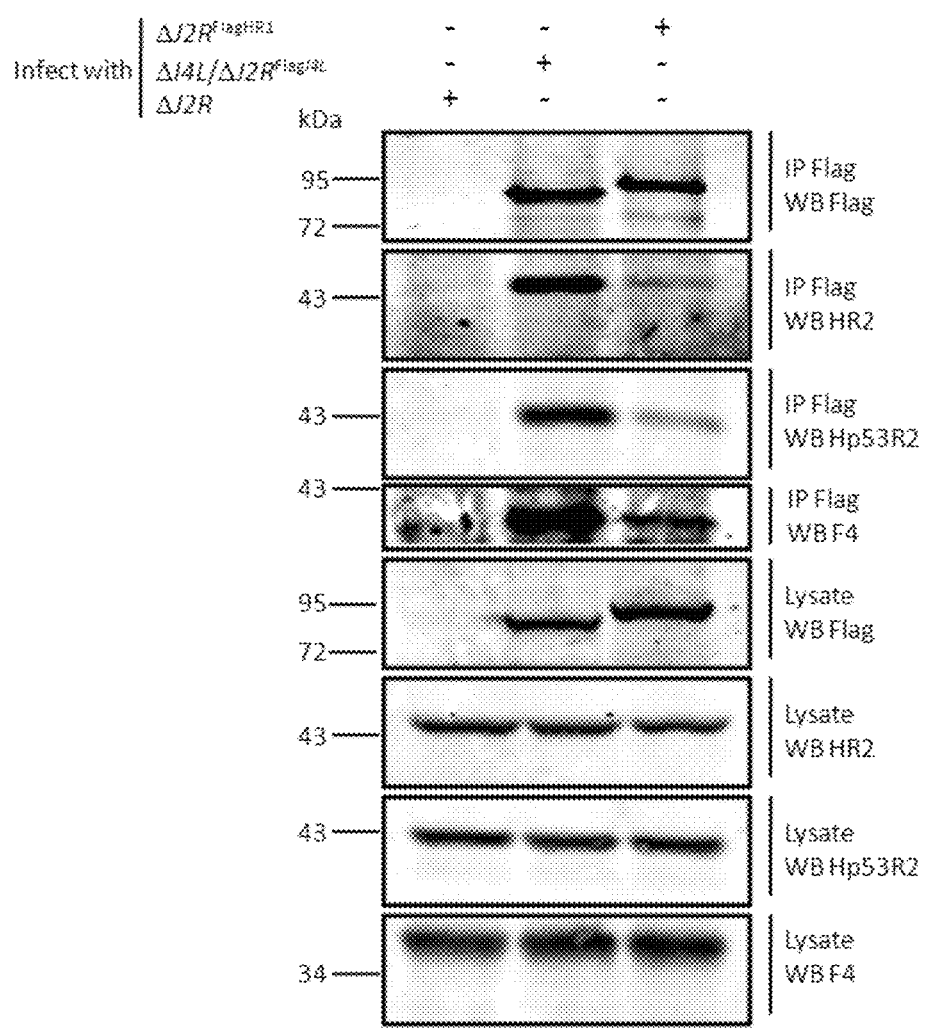
Figure 6:
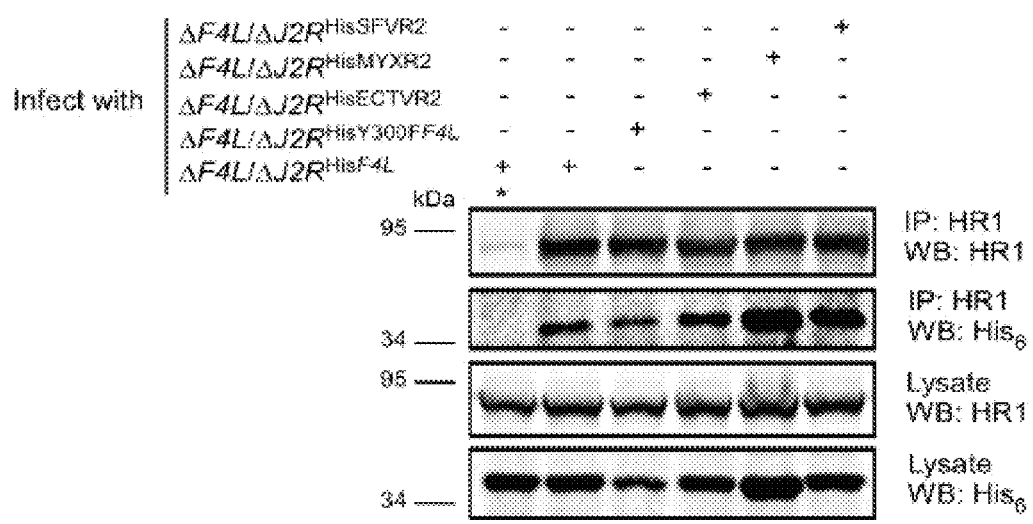

FIG. 6: Human and viral RR proteins are localized to the cytoplasm during infection with VACV. A) Localization of human RR subunits in the absence or presence of infection. HeLa cells were mock-infected (mock) or infected with wild-type VACV (VAC) at an MOI of 5 for 10 h after which coverslips were fixed and stained with antibodies against endogenous human R1 (HR1), R2 (HR2), or p53R2. B) Localization of recombinant human and VACV RR subunits during infection. HeLa cells were co-infected with the indicated strains (MOI of 5 for each virus) for 10 h after which coverslips were fixed and stained with antibodies recognizing Flag or His$_6$ epitopes. Arrows indicate positions of cytoplasmic viral DNA. DIC, differential interference contrast.

Figure 7:
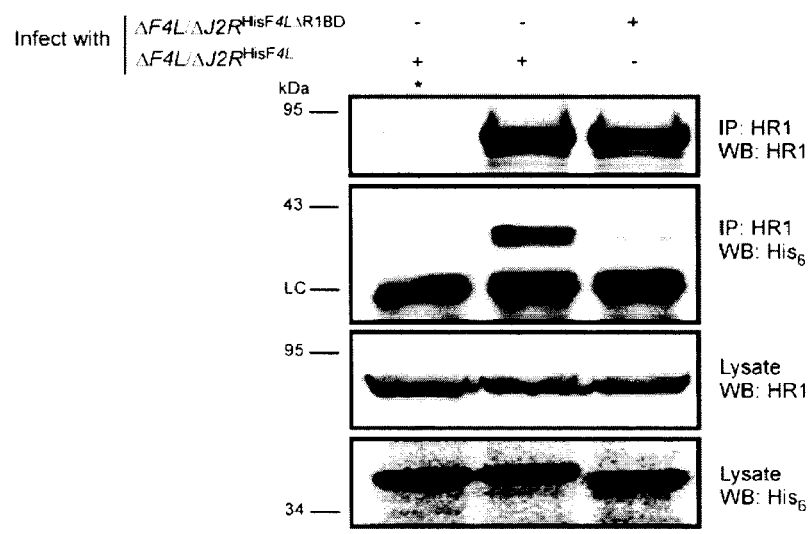
Figure 7:
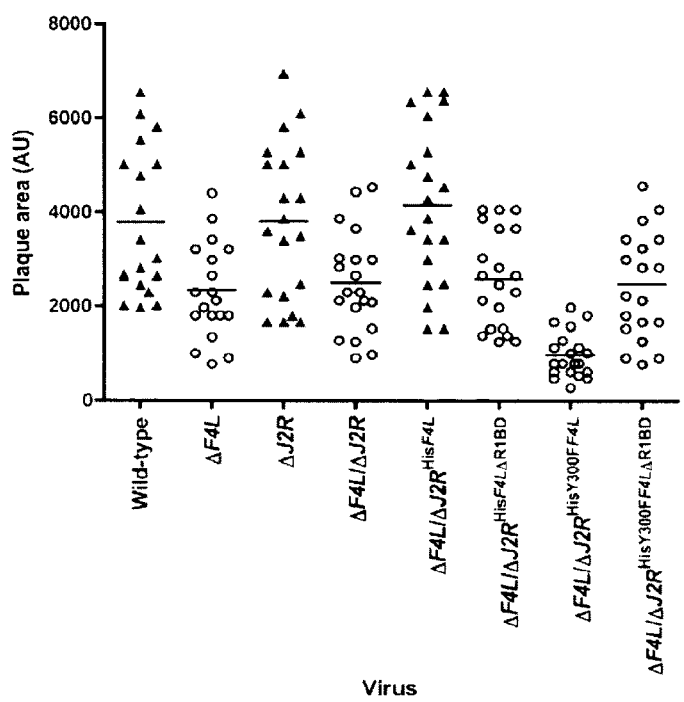

FIG. 7: Deletion of F4 C-terminus residues inhibits interaction with HR1 and impairs virus growth. A) Co-immunoprecipitation of recombinant F4 proteins with HR1. HeLa cells were infected with the indicated strains at a MOI of 10 for 8 h and then protein extracts were subjected to immunoprecipitation (IP) with anti-HR1 antibodies or control serum (indicated by "*"). Western blots (WB) of IP material and total lysates are shown. LC, light chain. B) Plaque area analysis of RR mutant strains. BSC-40 monolayers in 60-mm-diameter plates were infected with ~100 PFU of the indicated strains and stained 48 h post-infection with crystal violet. The scatter plots illustrate independent (n=20) as well as mean (horizontal bar) plaque area measurements in arbitrary units (AU) for each of the indicated strains. Open circles indicate that the mean plaque area was statistically different (P<0.05) from wild-type virus as determined by a one-way ANOVA.

Figure 8:
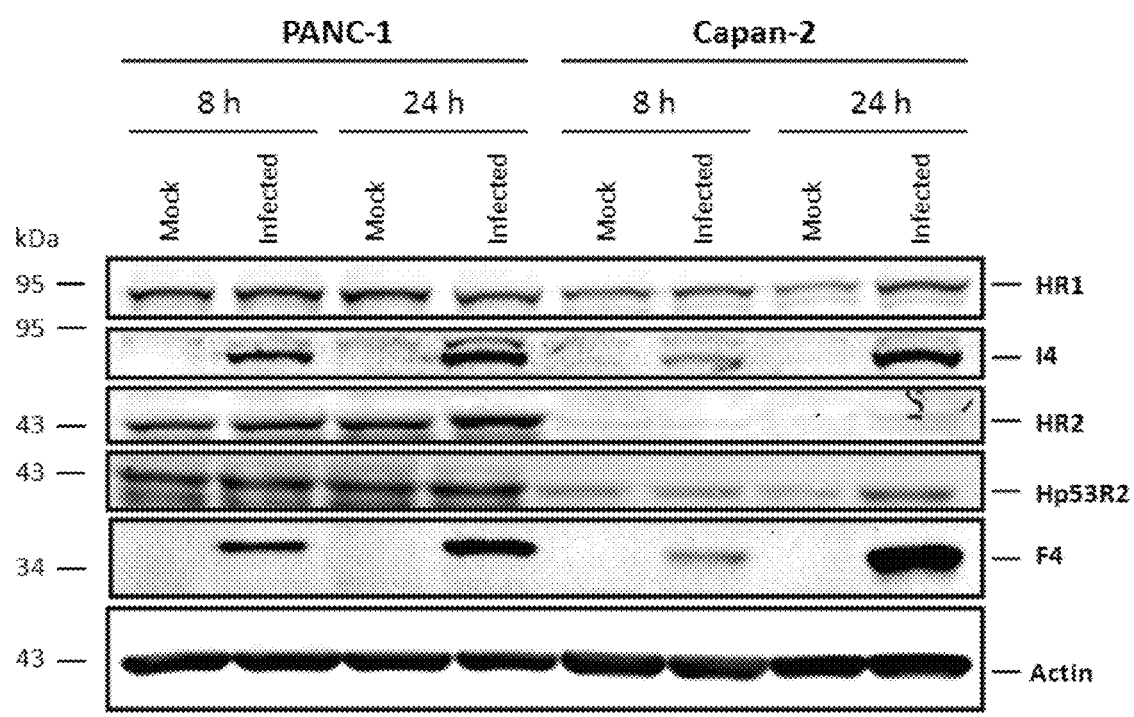
Figure 8:
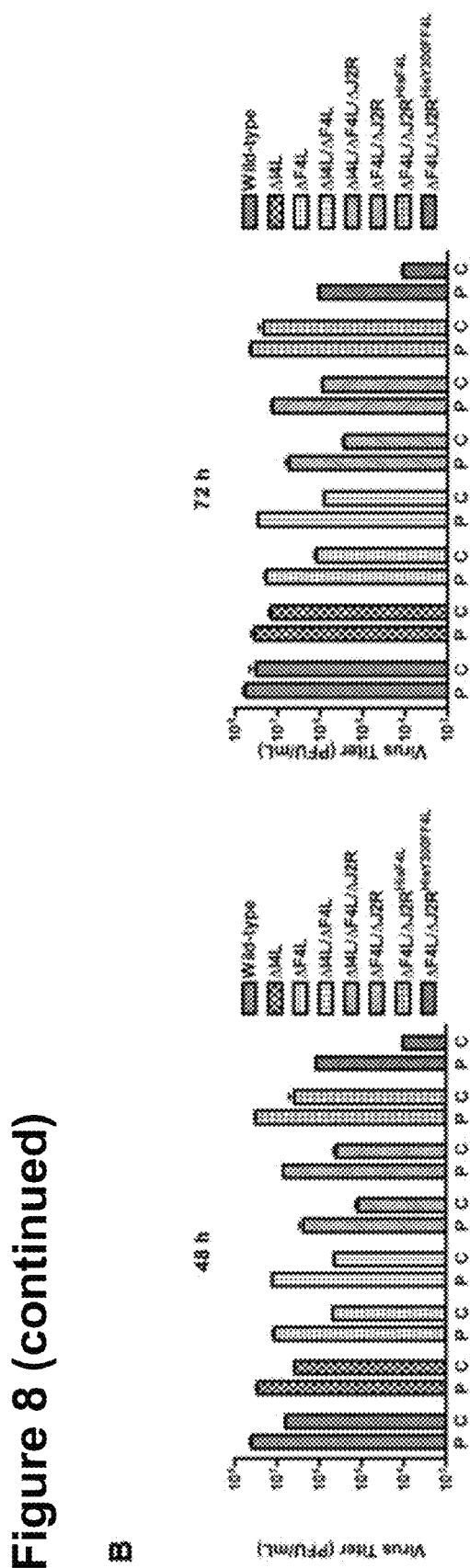
Figure 8:
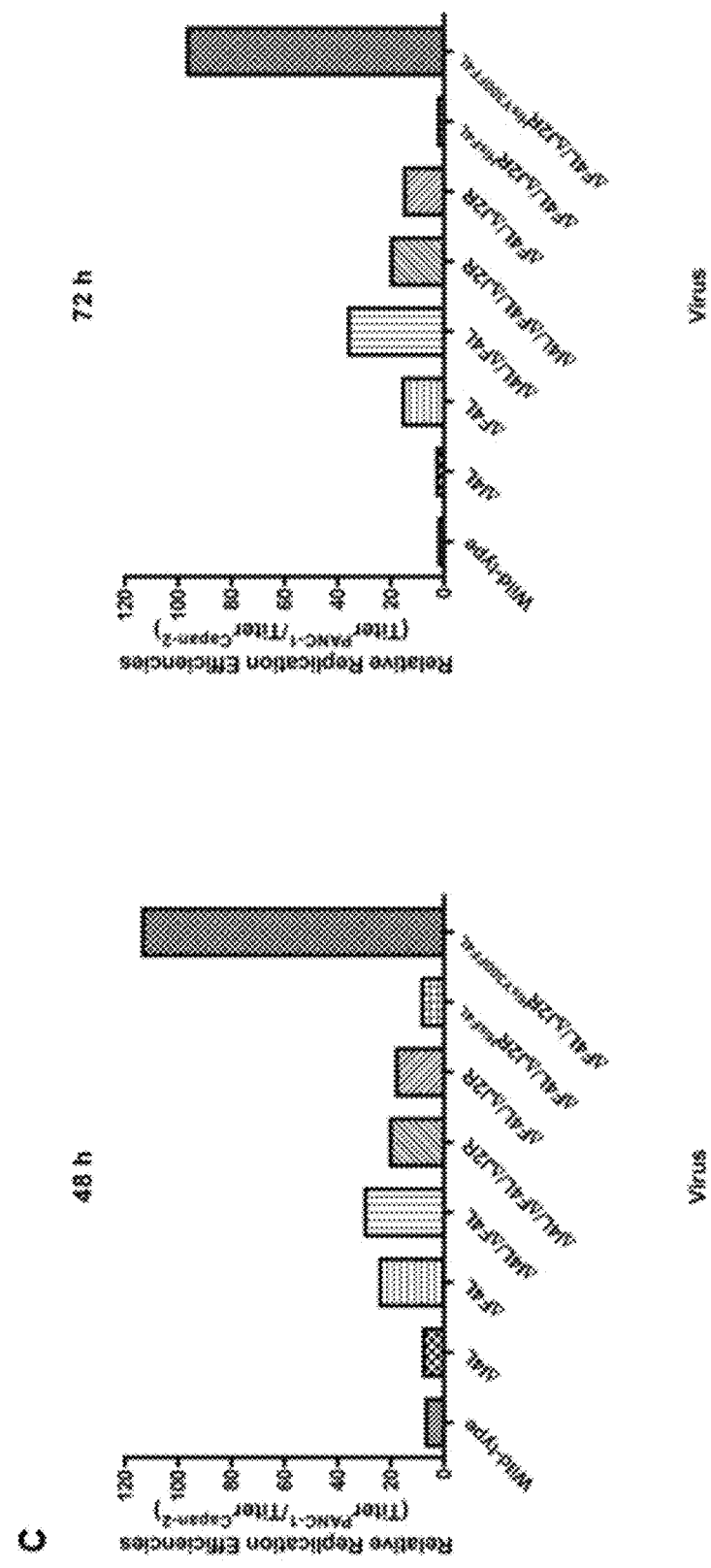

FIG. 8: Correlation of cellular RR subunit expression and mutant vaccinia virus strain replication in two human pancreatic cancer cell lines. A) Western blot analysis of viral and cellular RR subunit expression of protein extracts made from mock-infected and wild-type-infected (MOI=5) PANC-1 and Capan-2 cells at the indicated times post-infection. B) Mean virus yields (+SE) after 48 h or 72 h of infection (M01=0.03) of PANC-1 (P) or Capan-2 (C) cells with the indicated strains. C) Replotting of the data in B) to show the relative difference in mean replication efficiencies between the two cell lines for the indicated strains. Virus lacking both I4L and F4L genes replicate 30-40 times better on PANC-1 cells which overexpress cellular RR subunits compared to Capan-2 cells. Virus encoding the Y300F substitution replicate ~100-115 times better on PANC-1 cells compared to Capan-2 cells.

Figure 9:
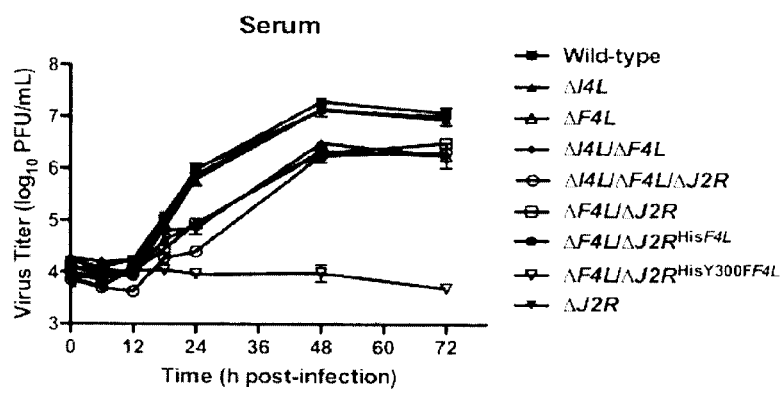
Figure 9:
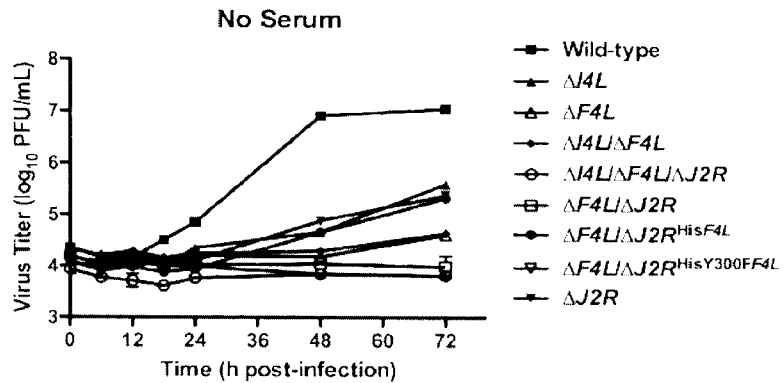
Figure 9:
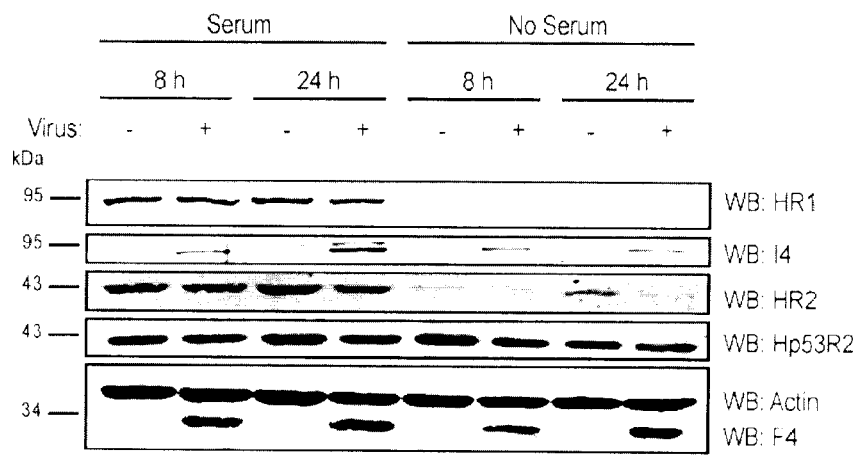

FIG. 9: Replication of VACV strains in human primary cells. Primary human embryonic lung (HEL) cells were cultured for 96 h in DMEM containing either 10% (Serum) A) or 0.5% (No Serum) B) FBS prior to infection (MOI=0.03) with the indicated VACV strains. At the indicated times cells were harvested, freeze-thawed three times and tittered on BSC-40 cells. Error bars represent SD although some error bars are approximately the size of the symbols. C) HEL cells were cultured as in (A) and (B) and then infected with wild-type VACV (MOI=5) or mock-infected. At the indicated times protein extracts were prepared from cell lysates. Equal amounts of protein were separated by SDS-PAGE followed by western blotting (WB) with antibodies directed against human R1 human R1 (HR1), human R2 (HR2), human p53R2 (Hp53R2), VACV I4 or VACV F4. Blots for cellular actin served as loading controls.

Figure 10:
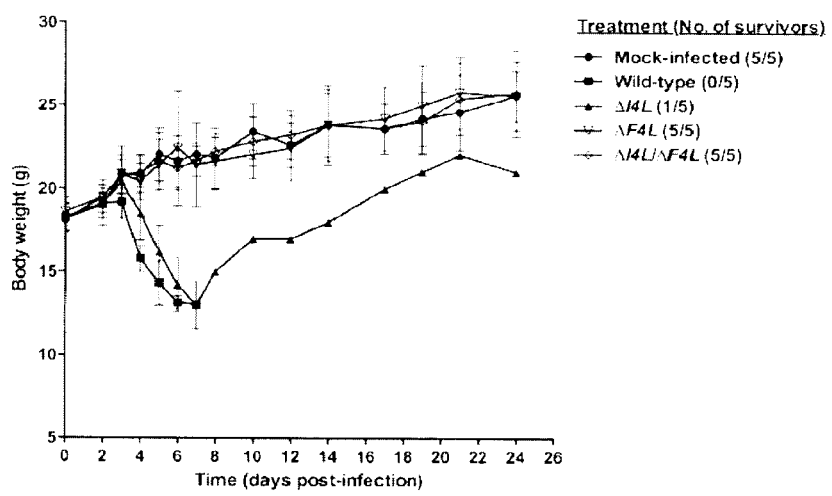
Figure 10:
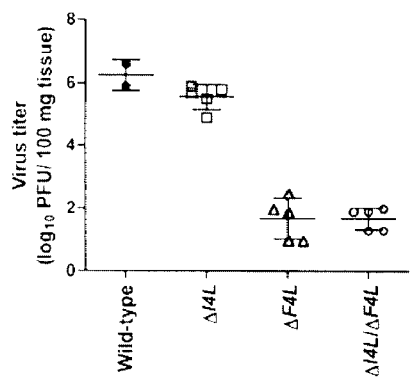

FIG. 10: Differential requirement of VACV RR subunits for pathogenesis. (A) Analysis of animal body weight after infection with RR mutant strains. Groups of 5 NMRI mice were inoculated by an intranasal route with 40,000 PFU of the indicated VACV strains or were mock-infected with sterile buffer. Symbols represent mean body weight of each group of mice (or surviving members) over the indicated times post-infection. The number of surviving mice in each treatment group is indicated in parentheses. Error bars represent SD. (B) Lung titers after infection with RR mutant strains. The scatter plot shows lung virus titers from individual mice with means (horizontal bars) for each group. Mice were infected in parallel with studies in (A) and were euthanized 5 days post-infection. Lung virus titers were determined as described in Materials and Methods.

Figure 11:
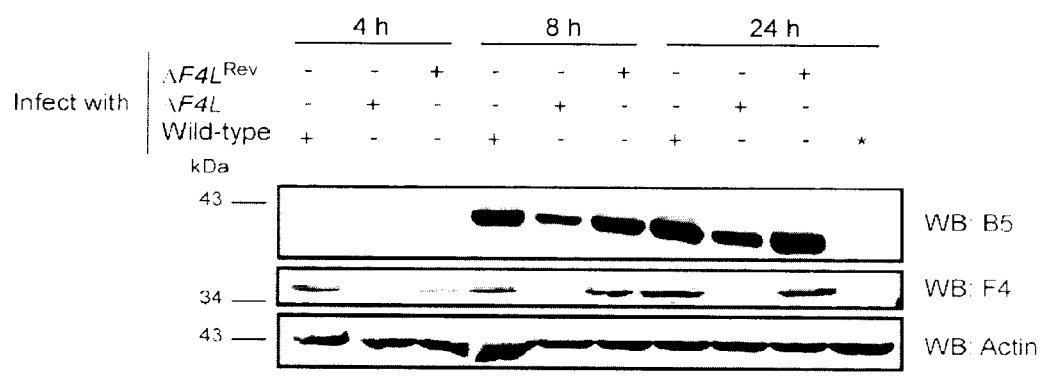
Figure 11:
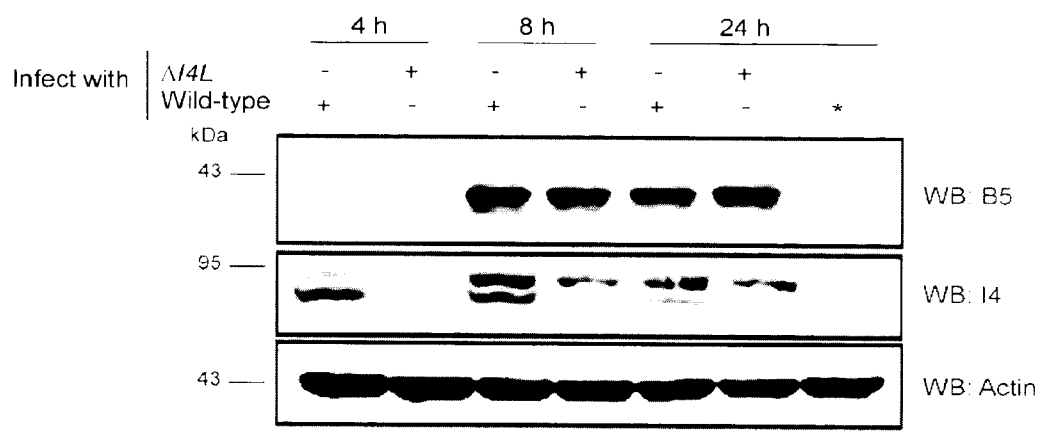

FIG. 11: The ΔF4L strain has reduced expression of the late VACV protein B5. (A) BSC-40 cells were infected (at a MOI of 5) with wild-type or VACV strains with a deletion of F4L (ΔF4L) or a ΔF4L revertant strain in which the F4L gene was reintroduced into the F4L locus in a ΔF4L background (ΔF4L$^{REV}$). (B) BSC-40 cells were infected as in (A) with wild-type virus or a VACV strain with a deletion of I4L (ΔI4L). Cells were harvested at the indicated times post-infection and protein extracts were prepared for western blotting. Antibodies against the VACV late protein B5, the early viral proteins F4 and I4 or cellular actin were used for blotting on parallel nitrocellulose membranes. Asterisks indicate mock-infected lysates collected after 24 h.

Figure 12:
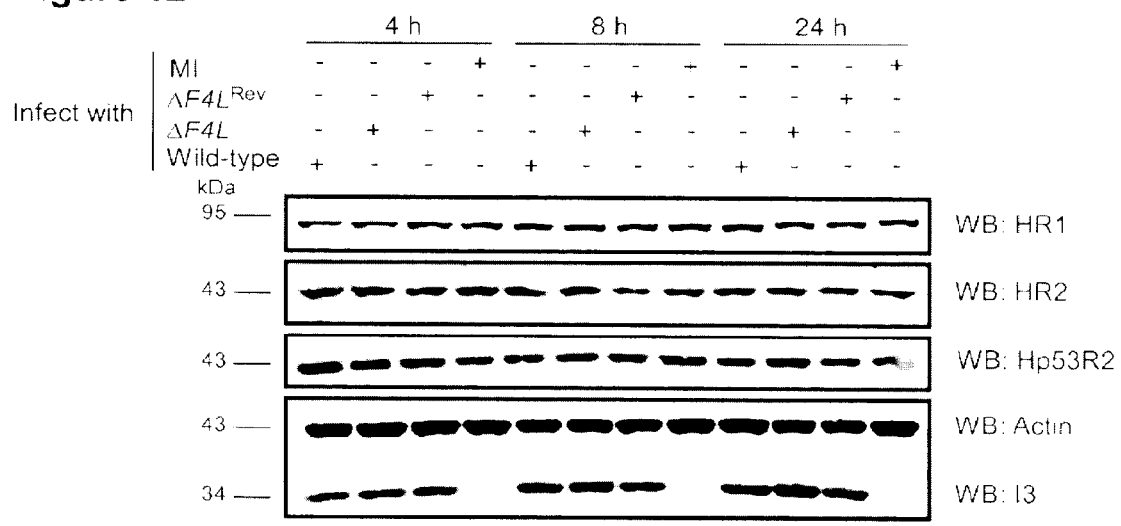

FIG. 12: Expression profile of cellular RR proteins after infection with VACV. HeLa cells were infected with wild-type, ΔF4L, or ΔF4L$^{REV}$ (revertant) strains (MOI of 5) or were mock-infected (MI). Protein extracts were prepared at the indicated times post-infection and equal amounts of protein were subjected to SDS-PAGE followed by western blotting (WB) for human R1 (HR1), human R2 (HR2), or human p53R2 (Hp53R2). Blots for cellular actin and VACV 13 protein served as loading controls.

Figure 13:
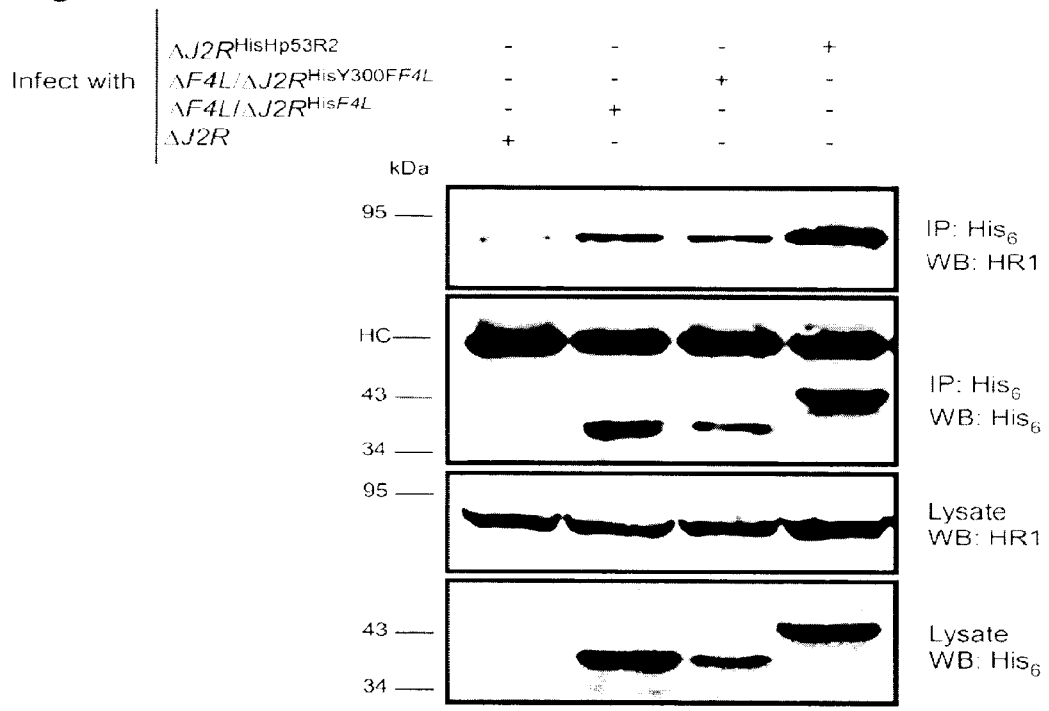

FIG. 13: Co-immunoprecipitation of His$_6$-tagged F4 with human R1 (HR1). HeLa cells were infected with the indicated strains (MOI of 10) for 8 h and then protein extracts were subjected to immunoprecipitation (IP) with anti-His$_6$ antibodies. Western blots (WB) of IP material and total lysates are shown. HC, heavy chain. Note that VACV F4 is ~37 kDa while Hp53R2 (positive control for HR1 interaction) is ~43 kDa.

Figure 14:
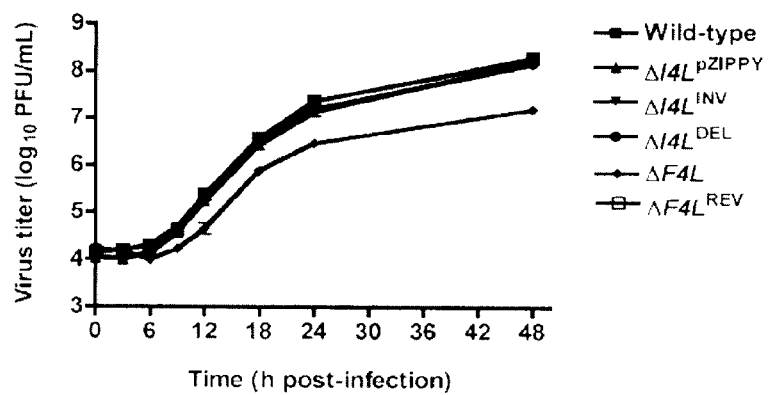
Figure 14:
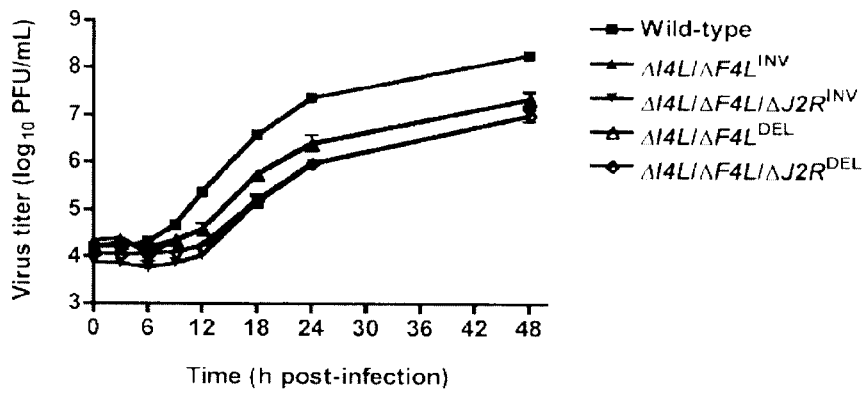

FIG. 14: Growth properties of selected recombinant strains in BSC-40 cells. Cells were infected at a MOI of 0.03, harvested at the indicated time points, freeze-thawed three times, and tittered on BSC-40 cells. Although the experiments in (A) and (B) were done in parallel, they are separated for clarity purposes and thus the wild-type curve is the same in both graphs. The superscript labels above certain virus strains refer to whether the I4L locus was inactivated using pDGIox-PKO$^{INV}$ (INV)- or pDGIoxPKO$^{DEL}$ (DEL)- or pZIPPY-NEO/GUS (pZippy)-based vectors. A superscript "REV" refers to a revertant of the ΔF4L strain. All pDGIoxPKO-based viruses went through a final, three-round plaque purification procedure in Cre recombinase-expressing U2OS cells. Symbols represent mean titers determined in triplicate and error bars represent SD. Some error bars are approximately the same size of the symbols.

Table 1: Major VACV strains used in this study.
Table 2: Susceptibility of VACV RR mutant strains to cidofovir (CDV), hydroxyurea (HU) and phosphonoacetic acid (PAA).
Table 3: Differential conservation of Chordopoxirinae RR genes.
Table 4: List of Cancer types that over-express RR proteins.
Table 5: List of sequences.

DETAILED DESCRIPTION i. Definitions

The term "functionally inactivated gene" refers to a gene comprising one or more mutations (e.g. natural or engineered), such as a point mutation, a dominant negative mutation and/or a deletion mutation e.g. producing a deletion mutant, wherein a biological function of the protein encoded by the gene, and/or a biological function of any complex in which the protein participates, is inactivated, e.g. reduced by at least 50%, at least 60%, at least 70%, at least 80%, at least 90%, at least 95%, or more and/or ablated e.g. totally inhibited compared to a wild type molecule. The biological function can be reduced by various mechanisms, e.g. the coding sequence or gene can be deleted entirely and/or partially, ablating or decreasing for example enzymatic and/or structural functions of the encoded protein, the encoded protein can act as a dominant negative (such as a catalytic mutant) and form inactive complexes, and/or the encoded protein can be structurally and/or catalytically inactive (e.g. when the gene encodes an enzyme). Also for example, the promoter of a gene such as R2 can be deleted, inactivating R2 function by inhibiting its expression. For example, "functionally inactivated R2 gene" means a R2 coding sequence that encodes a protein that has decreased biological function, such as decreased catalytic activity, or which decreases catalytic activity of an RR complex. The R2 coding sequence can be mutated for example by deleting or mutating sequence encoding one or more catalytically important residues, deleting a sequence encoding a R1 binding domain or other mutation that decreases R2 protein and/or activity levels. A person skilled in the art, based on the present disclosure would readily, by comparing to wild-type and/or a mutant described herein, be able to determine if a particular mutation or deletion functionally inactivated R2.

The term "neoplastic disorder" as used herein refers to proliferative and/or dysplastic disorders including for example cancers of any kind and origin as well as precursor stages thereof, including for example, cancers, neoplasia, precancer and/or tumor.

The term "cancer" as used herein refers to a cancer of any kind and origin including tumor-forming cells, blood cancers and/or transformed cells.

The term "neoplastic disorder cell" refers to one or more cells derived from or phenotypically similar to proliferative and/or dysplastic disorder cells such as cancer cells of any kind and origin as well as precursor stages thereof, including for example, neoplastic cells, precancer cells and/or tumor cells.

The term "cancer cell" includes cancer or tumor-forming cells, transformed cells or a cell that is susceptible to becoming a cancer or tumor-forming cell.

The term "a cell" includes a single cell as well as a plurality or population of cells. Administering a composition to a cell includes both in vitro and in vivo administrations.

The term "isolated poxvirus" as used herein includes but is not limited to naturally occurring, selected, such as chemically selected, and recombinant poxviruses that have been isolated, for example purified, for example by a method known to a person of skill in the art. An isolated poxvirus comprising a functionally inactivated R2 includes for example isolated poxviruses that have been inactivated for R2 using recombinant methods and/or naturally occurring variants and/or variants isolated under selection pressure or conditions that result in genome mutations (e.g. chemically or irradiation induced mutations) wherein the R2 gene is functionally inactivated.

The term "recombinant poxvirus" refers to an engineered poxvirus, such as a vaccinia virus engineered to comprise a deletion that inactivates the activity of a gene product, that is generated in vitro generated using recombinant DNA technology and/or a poxvirus derived from such a recombined poxvirus, (e.g. progeny virus).

The term "oncolytic" as used herein refers to a tumor selective replicating virus that induces cell death in the infected cell, and/or tissue. Although normal or non-tumor cells may be infected, tumor cells are infected and lysed selectively in comparison to the normal or non-tumor cells. For example, an isolated poxvirus is oncolytic if it induces at least 5 fold, at least 6 fold, at least 10 fold, at least 15 fold, or at least 20 fold more cell death in a population of neoplastic disorder cells compared to control cells. Optionally the poxvirus oncolytic activity is preferentially oncolytic in neoplastic disorder cells overexpressing an RR subunit, optionally R1 or R2.

The term "cell death" as used herein includes all forms of cell death including for example cell lysis and/or apoptosis. Vaccinia virus for example is known to induce cell death by cell lysis and/or apoptosis. Cell death of a poxvirus infected cell and/or neighbouring cell may also refer for example to elimination of the cell by host immune system functions.

The term "level" as used herein refers to an absolute or relative quantity of a transcription product, e.g. polypeptide or mRNA, or an activity of such a polypeptide, for example, a RR level, such as R1, refers to the level or RR that is detectable or measurable in a cell or tissue from a subject or a population of subjects, optionally from a subject or population of subjects who are known as having (e.g. test level) or not having (e.g. control level) a neoplastic disorder such as a cancer. The level can be a numerical value and/or range and can refer to polypeptide levels, nucleic acid levels, or activity levels. Where the level is for a control sample, the control level can also refer to a RR level in non-neoplastic and/or non-cancerous cell or tissue, for example as is found adjacent to tumor for example in a tumor biopsy (e.g. normal adjacent). Where the level is for a test sample, the test level refers to a RR level in a neoplastic and/or a cancerous cell or tissue. For example, when determining if a neoplastic disorder and/or cancer has increased RR levels, the level of RR determined using a test sample comprising a neoplastic disorder and/or cancer cell and/or tissue (e.g. test level) can be compared to an RR level in a control sample or a predetermined corresponding numerical value (e.g. control level). Where the control level is a numerical value or range, the numerical value or range is a value or range that corresponds to a level of the RR level or range in a control sample or control samples (e.g. can be a threshold or cutoff level or a control range) and can be predetermined.

The term "expression level" as used herein refers to the absolute or relative amount of the transcription and/or translation product of a gene described herein and includes RNA and polypeptide products. A person skilled in the art will be familiar with a number of methods that can be used to determine RNA transcription levels, such as qRT-PCR and/or polypeptide levels such as immunohistochemistry and/or western blotting.

The term "increased level" or "elevated level" as used herein in reference to RR mRNA and/or protein expression levels in a cell refers to any detectable increase in the measurable expression level of a RR expression product, as measured by the amount of messenger RNA (mRNA) transcript and/or the amount of polypeptide in a sample as compared with the measurable expression level of a RR in a control or comparator cell of the same tissue type. For example a cancer cell can have an increased level in comparison to a normal cell of the same tissue type.

The term "normal tissue" as used herein refers to non-neoplastic tissue and/or tissue derived from a subject that is free of cancer of the particular tissue (e.g. when the tissue is pancreas "normal tissue" can be derived from a subject that does not have pancreatic cancer). The term "normal cell of the same tissue type" as used herein refers to a cell or cells derived from such normal tissue.

As used herein, to "inhibit" or "reduce" a function or activity, such as RR activity and/or binding, is any reduction in the function or activity when compared to otherwise same conditions except for a condition or parameter of interest, or alternatively, as compared to another condition.

The term "interacts" or "interacting", for example with respect to protein subunits that form a complex, refers to the physical direct or indirect binding of one subunit to one or more other subunits. For example, large and small RR subunits may interact to form a complex. The binding may be indirect (e.g. for example, via a binding partner).

The term "resistant cancer" or "chemotherapeutic resistant cancer" refers to a cancer that has decreased sensitivity to one or more chemotherapeutic drugs, for example by amplifying a gene that allows it to persist in the presence of the drug, for example by increasing RR expression.

The term "sample" as used herein, for example for detecting levels of RR or dNTPS, refers to any fluid, cell or tissue sample from a subject that is assayable for the molecule of interest for example that comprises a cell or tissue for example of a neoplastic disorder that is being treated. For example, the sample can be a biopsy of the cancer, or a blood sample for blood disorders. For example, if polypeptide levels are being assayed, the sample comprises protein. If a nucleic acid molecule is being assayed, the sample comprises nucleic acid. If catalytic activity is being determined, the sample is suitably prepared to permit detection of the catalytic activity being assayed as would be familiar to one skilled in the art.

The term "control sample" as used herein in the context of determining RR levels, refers to a sample comprising a normal cell or tissue suitable for determining a RR level, the cell or tissue obtained from a subject or a population of subjects (e.g. control subjects), optionally from a subject or population of subjects who are known as not having a neoplastic disorder and/or cancer, or optionally obtained from the a subject with a neoplastic disorder and/or cancer wherein the control sample comprises non-neoplastic and/or non-cancerous tissue (e.g. normal adjacent). For example, the control sample can be compared to a sample from the subject comprising tumor cells, wherein the control sample is the same sample type as the sample comprising tumor cells (e.g. both the sample and the control are serum samples), or both the sample and control sample derive from the same tissue (e.g. T cell leukemia compared with T cell sample (control)). The control sample can also comprise normal adjacent tissue for example, comparing a tumor sample to adjacent normal control tissue.

As used herein "vector backbone" refers to a nucleic acid molecule that is used as a vehicle to deliver one or more nucleic acid molecules, such as a mutant R2 gene, into a cell, e.g. to allow recombination. The vector backbone can refer optionally to the plasmid construct that is used to generate virus or to a virus genome (e.g. the non-recombined virus genome). Optionally, the vector backbone is constructed to permit expression of one or more transgenes (e.g an expression cassette) and the construct (e.g. vector backbone and transgene) can be referred to as an expression vector. A vector backbone into which has been inserted one or more nucleic acids to be transferred to a cell, is referred to as a vector construct.

The term "isolated vector construct", as used herein refers to a nucleic acid substantially free of cellular material or culture medium when produced for example by recombinant DNA techniques.

The term "detection cassette" is used to refer to a polynucleotide that directs expression of a molecule that acts as a cell marker and that optionally provides for a mode of isolating cells expressing said marker. The molecule is optionally used to select infected or transfected cells or to determine the efficiency of cell transduction or transfection. Molecules that are useful as cell markers or detection agents comprise for example, EGFP or derivatives thereof such as YFP and RFP, HSA, GFP or derivatives thereof such as YFP and RFP, enhanced GFP, mCherry, β-glucuronidase, β-galactosidase, firefly or *renilla* luciferase ETC. One skilled in the art will recognize that other fluorescent and non-fluorescent molecules can similarly be used.

The term "antibody" as used herein is intended to include monoclonal antibodies, polyclonal antibodies, and chimeric antibodies. The antibody may be from recombinant sources and/or produced in transgenic animals. The term "antibody fragment" as used herein is intended to include Fab, Fab', F(ab')2, scFv, dsFv, ds-scFv, dimers, minibodies, diabodies, and multimers thereof and biospecific antibody fragments. Antibodies can be fragmented using conventional techniques. For example, F(ab')2 fragments can be generated by treating the antibody with pepsin. The resulting F(ab')2 fragment can be treated to reduce disulfide bridges to produce Fab' fragments. Papain digestion can lead to the formation of Fab fragments. Fab, Fab' and F(ab')2, scFv, dsFv, ds-scFv, dimers, minibodies, diabodies, biospecific antibody fragments and other fragments can also be synthesized by recombinant techniques. Methods for making antibodies are well known in the art.

The term "nucleic acid" includes DNA and RNA and can be either double stranded or single stranded.

The term "isolated nucleic acid" as used herein refers to a nucleic acid substantially free of cellular material or culture medium when produced by recombinant DNA techniques, or chemical precursors, or other chemicals when chemically synthesized. An "isolated nucleic acid" is also substantially free of sequences which naturally flank the nucleic acid (i.e. sequences located at the 5' and 3' ends of the nucleic acid) from which the nucleic acid is derived. The term "nucleic acid" is intended to include DNA and RNA and can be either double stranded or single stranded. The nucleic acid sequences contemplated by the present application include isolated nucleotide sequences which hybridize to a RNA product of a biomarker, nucleotide sequences which are complementary to a RNA product of a biomarker of the present application, nucleotide sequences which act as probes, or nucleotide sequences which are sets of specific primers The term "primer" as used herein refers to a nucleic acid sequence, whether occurring naturally as in a purified restriction digest or produced synthetically, which is capable of acting as a point of synthesis of when placed under conditions in which synthesis of a primer extension product, which is complementary to a nucleic acid strand is induced (e.g. in the presence of nucleotides and an inducing agent such as DNA polymerase and at a suitable temperature and pH). The primer must be sufficiently long to prime the synthesis of the desired extension product in the presence of the inducing agent. The exact length of the primer will depend upon factors, including temperature, sequences of the primer and the methods used. A primer typically contains 15-25 or more nucleotides, although it can contain less. The factors involved in determining the appropriate length of primer are readily known to one of ordinary skill in the art.

The terms "R1" and "R2" as used herein refer to the large and small subunits of a ribonucleotide reductase complex, respectively. "R1" and "R2" may refer to the ribonucleotide reductase subunits of, for example: mammals, including, but not limited to humans, and viruses, including, but not limited to poxviruses, such as vaccinia viruses. Homodimers of large and small subunits interact to form a functional ribonuclease reductase complex. Alternatives names for R1 include, but are not limited to, "I4L", "I4" "large RR subunit", "large subunit", "M1", and "RRM1". Alternative names for R2 include, but are not limited to, "F4L", "F4" "small RR subunit", "small subunit", "RRM2" and, "M2". Further species can be referred to specifically, for example, human R1 is denoted as HR1 and human R2 is denoted as HR2. Also for example viral R1 protein is also denoted as I4 and viral R1 gene is denoted as "I4L" or when referring to the WR strain, VACV-WR-073 Similarly, the viral R2 protein is denoted "F4" and the gene is denoted "F4L" or "VACV-WR-043" when referring to the WR strain specifically. A person skilled in the art would be familiar with the various nomenclatures used for vaccinia genes. For example, the "old", but more common, nomenclature for vaccinia genes uses letter-based designations (i.e. F4L and I4L) a newer nomenclature based on the open reading frame (ORF) number (from the left side of the genome to the right side) uses numbers to indicate the ORF number from the left side (e.g. I4L is the $73^{rd}$ ORF from the start of the genome).

The term "p53R2" as used herein refers to an alternative R2 subunit encoded for in mammalian cells (e.g. mouse p53R2; Genbank accession: □6PEE3.1). The term "Hp53R2" as used herein refers to the human form of p53R2 (Genbank accession: BAD12267.1).

The term "cellular RR" as used herein refers to the one or more subunits of a non-viral RR protein, for example a human RR subunit. It is disclosed herein for example that poxvirus R1 can interact (e.g. functionally bind) cellular (e.g. mammalian) R2 to form a functional hybrid complexes.

The term "sequence identity" as used herein refers to the percentage of sequence identity between two polypeptide sequences or two nucleic acid sequences. To determine the percent identity of two amino acid sequences or of two nucleic acid sequences, the sequences are aligned for optimal comparison purposes (e.g., gaps can be introduced in the sequence of a first amino acid or nucleic acid sequence for optimal alignment with a second amino acid or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=number of identical overlapping positions/total number of positions.times.100%). In one embodiment, the two sequences are the same length. The determination of percent identity between two sequences can also be accomplished using a mathematical algorithm. A preferred, non-limiting example of a mathematical algorithm utilized for the comparison of two sequences is the algorithm of Karlin and Altschul, 1990, Proc. Natl. Acad. Sci. U.S.A. 87:2264-2268, modified as in Karlin and Altschul, 1993, Proc. Natl. Acad. Sci. U.S.A. 90:5873-5877. Such an algorithm is incorporated into the NBLAST and XBLAST programs of Altschul et al., 1990, J. Mol. Biol. 215:403. BLAST nucleotide searches can be performed with the NBLAST nucleotide program parameters set, e.g., for score=100, wordlength=12 to obtain nucleotide sequences homologous to a nucleic acid molecules of the present application. BLAST protein searches can be performed with the XBLAST program parameters set, e.g., to score-50, wordlength=3 to obtain amino acid sequences homologous to a protein molecule of the present application. To obtain gapped alignments for comparison purposes, Gapped BLAST can be utilized as described in Altschul et al., 1997, Nucleic Acids Res. 25:3389-3402. Alternatively, PSI-BLAST can be used to perform an iterated search which detects distant relationships between molecules (Id.). When utilizing BLAST, Gapped BLAST, and PSI-Blast programs, the default parameters of the respective programs (e.g., of XBLAST and NBLAST) can be used (see, e.g., the NCBI website). The percent identity between two sequences can be determined using techniques similar to those described above, with or without allowing gaps. In calculating percent identity, typically only exact matches are counted.

A "conservative amino acid substitution" as used herein, is one in which one amino acid residue is replaced with another amino acid residue without abolishing the protein's desired properties. Conservative amino acid substitutions are known in the art. For example, conservative substitutions include substituting an amino acid in one of the following groups for another amino acid in the same group: alanine (A), serine (S), and threonine (T); aspartic acid (D) and glutamic acid (E); asparagine (N) and glutamine (Q); arginine (R) and lysine (L); isoleucine (I), leucine (L), methionine (M), valine (V); and phenylalanine (F), tyrosine (Y), and tryptophan (W).

The term "hybridize" refers to the sequence specific non-covalent binding interaction with a complementary nucleic acid.

By "at least moderately stringent hybridization conditions" it is meant that conditions are selected which promote selective hybridization between two complementary nucleic acid molecules in solution. Hybridization may occur to all or a portion of a nucleic acid sequence molecule. The hybridizing portion is typically at least 15 (e.g. 20, 25, 30, 40 or 50) nucleotides in length. Those skilled in the art will recognize that the stability of a nucleic acid duplex, or hybrids, is determined by the Tm, which in sodium containing buffers is a function of the sodium ion concentration and temperature ($T_m$=81.5° C.−16.6 (Log 10 [Na+])+0.41 (% (G+C)−600/l), or similar equation). Accordingly, the parameters in the wash conditions that determine hybrid stability are sodium ion concentration and temperature. In order to identify molecules that are similar, but not identical, to a known nucleic acid molecule a 1% mismatch may be assumed to result in about a 1° C. decrease in Tm, for example if nucleic acid molecules are sought that have a >95% identity, the final wash temperature will be reduced by about 5° C. Based on these considerations those skilled in the art will be able to readily select appropriate hybridization conditions. In preferred embodiments, stringent hybridization conditions are selected. By way of example the following conditions may be employed to achieve stringent hybridization: hybridization at 5× sodium chloride/sodium citrate (SSC)/5× Denhardt's solution/1.0% SDS at Tm−5° C. based on the above equation, followed by a wash of 0.2×SSC/0.1% SDS at 60° C. Moderately stringent hybridization conditions include a washing step in 3×SSC at 42° C. It is understood, however, that equivalent stringencies may be achieved using alternative buffers, salts and temperatures. Additional guidance regarding hybridization conditions may be found in: Current Protocols in Molecular Biology, John Wiley & Sons, N.Y., 2002, and in: Sambrook et al., Molecular Cloning: a Laboratory Manual, Cold Spring Harbor Laboratory Press, 2001.

The term "treating" or "treatment" as used herein and as is well understood in the art, means an approach for obtaining beneficial or desired results, including clinical results. Beneficial or desired clinical results can include, but are not limited to, alleviation or amelioration of one or more symptoms or conditions, diminishment of extent of disease, stabilized (i.e. not worsening) state of disease, preventing spread of disease, delay or slowing of disease progression, amelioration or palliation of the disease state, diminishment of the reoccurrence of disease, and remission (whether partial or total), whether detectable or undetectable. "Treating" and "Treatment" can also mean prolonging survival as compared to expected survival if not receiving treatment. "Treating" and "treatment" as used herein also include prophylactic treatment. For example, a subject with early stage neoplastic disorder with increased RR levels can be treated to prevent progression or alternatively a subject in remission can be treated with an isolated or recombinant poxvirus or composition described herein to prevent recurrence. Treatment methods comprise administering to a subject a therapeutically effective amount of one or mores isolated or recombinant poxvirus or compositions described in the present application and optionally consists of a single administration, or alternatively comprises a series of applications. For example, the isolated and/or recombinant viruses and compositions described herein may be administered at least once a week, from about one time per week to about once daily for a given treatment or the isolated or recombinant poxviruses and/or compositions described herein may be administered twice daily. As another example, the isolated or recombinant poxvirus is administered once only, or for example every 3 weeks for 4 cycles. The length of the treatment period depends on a variety of factors, such as the severity of the disease, the age of the patient, the concentration, the activity of the isolated or recombinant poxviruses and/or compositions described herein, and/or a combination thereof. It will also be appreciated that the effective dosage used for the treatment or prophylaxis may increase or decrease over the course of a particular treatment or prophylaxis regime. Changes in dosage may result and become apparent by standard diagnostic assays known in the art. In some instances, chronic administration may be required.

The dosage administered will vary depending on the use and known factors such as the pharmacodynamic characteristics of the particular substance, and its mode and route of administration, age, health, and weight of the individual recipient, nature and extent of symptoms, kind of concurrent treatment, frequency of treatment, and the effect desired. Dosage regime may be adjusted to provide the optimum therapeutic response.

The term "subject" as used herein includes all members of the animal kingdom including mammals, and suitably refers to humans.

As used herein, "contemporaneous administration" and "administered contemporaneously" means that two substances are administered to a subject such that they are both biologically active in the subject at the same time. The exact details of the administration will depend on the pharmacokinetics of the two substances in the presence of each other, and can include administering one substance within 24 hours of administration of the other, if the pharmacokinetics are suitable. Designs of suitable dosing regimens are routine for one skilled in the art. In particular embodiments, two substances will be administered substantially simultaneously, i.e. within minutes of each other, or in a single composition that comprises both substances.

As used herein, the phrase "effective amount" or "therapeutically effective amount" means an amount effective, at dosages and for periods of time necessary to achieve the desired result. For example in the context or treating a neoplastic disorder, an effective amount is an amount that for example induces remission, reduces tumor burden, and/or prevents tumor spread or growth compared to the response obtained without administration of the isolated or recombinant poxviruses and/or compositions described herein. Effective amounts may vary according to factors such as the disease state, age, sex, weight of the subject. The amount of a given isolated or recombinant poxvirus and/or composition described herein that will correspond to such an amount will vary depending upon various factors, such as the given isolated or recombinant poxvirus and/or composition described herein, the pharmaceutical formulation, the route of administration, the type of disease or disorder, the identity of the subject or host being treated, and the like, but can nevertheless be routinely determined by one skilled in the art.

In understanding the scope of the present disclosure, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. Finally, terms of degree such as "substantially", "about" and "approximately" as used herein mean a reasonable amount of deviation of the modified term such that the end result is not significantly changed. These terms of degree should be construed as including a deviation of at least ±5% of the modified term if this deviation would not negate the meaning of the word it modifies.

As used in this specification and the appended claims, the singular forms "a", "an" and "the" include plural references unless the content clearly dictates otherwise. Thus for example, a composition containing "a virus" includes a mixture of two or more viruses. It should also be noted that the term "or" is generally employed in its sense including "and/or" unless the content clearly dictates otherwise.

The definitions and embodiments described in particular sections are intended to be applicable to other embodiments herein described for which they are suitable as would be understood by a person skilled in the art.

ii. Viruses, Vectors, Antibodies and Compositions

The disclosure relates to poxviruses with mutations of the small RR subunit in for example vaccinia virus (VACV) strains, and methods of using these viruses. These mutant strains exhibit an impaired ability to replicate, however, replication is rescued (either fully or partially) in cells over expressing cellular RR subunits, such as cancer cells with increased RR levels.

Cellular RR subunits were found to co-immunoprecipitate with VACV F4 in the presence or absence of. Furthermore, the disclosure provides immunofluorescence studies which indicate that viral RR subunits are found throughout the cytoplasm of infected cells, well-positioning them to interact with cellular RR subunits that also have an exclusively cytoplasmic localization. Without wishing to be bound by theory, it is believed that production of these virus/host RR complexes may help rescue defects in replication in the presence or absence of I4 (large RR subunit also referred to as R1). The disclosure provides that poxviruses require at least a small RR subunit for proper replication either to provide required dNTPs or because of some other, unknown function of these proteins.

Accordingly in an aspect, the disclosure provides an isolated poxvirus comprising a functionally inactivated R2 gene. In another embodiment, the disclosure provides a recombinant poxvirus comprising a functionally inactivated R2 gene. In another embodiment, the isolated or recombinant virus replicates more efficiently in cells with increased levels of RR. In another embodiment, the isolated or recombinant virus replicates more efficiently in neoplastic disorder cells than in wild type cells. In an embodiment, the poxvirus is not a NYCBH vaccinia virus comprising a deletion of 180 bp of R2 sequence. In a further embodiment, the poxvirus is not a Wyeth vaccinia virus vaccine strain comprising a deletion of 180 bp of R2 sequence.

It is demonstrated herein that viruses with either a deletion of the R2 gene or a point mutation in R2 that acts as a dominant negative and inhibits RR enzymatic function, are oncolytic and useful for treating neoplastic disorders. It is predictable that other mutations in R2 that interfere with and/or ablate RR activity compared to wild-type, for example R2 mutants that are catalytically inactive, preferably comprising deletions of a least one catalytically important residue, such as those illustrated in FIG. 1B and optionally which complex with other RR subunits interfering with RR activity (e.g. dominant negative mutants), or R2 mutants that are deleted for all or part of the R1 binding domain, are useful in the methods disclosed herein. Accordingly in an embodiment, the functionally inactivated R2 gene comprises a dominant negative mutation, a point mutation or a deletion mutation, wherein the R2 encoded protein of the deletion mutant lacks at least 2 amino acids. In another embodiment, the protein encoded by the functionally inactive R2 gene forms complexes with cellular RR subunits when expressed in a cell. In a further embodiment the deletion mutant lacks at least 5, at least 7, at least 10, at least 20, at least 30, at least 35, at least 40, at least 50, at least 60, at least 70, at least 80, at least 90, at least 100, at least 110, at least 120, at least 130, at least 140, at least 150, at least 160, at least 170, at least 180, at least 181, at least 190, at least 200, at least 210, at least 220, at least 230, at least 240, at least 250, at least 260, at least 270, at least 280, at least 290, at least 300, at least 310, or at least 320 amino acid residues. In another embodiment, the deleted amino acids comprise deletion of at least one catalytically important residue and or the R1 binding site, for example as provided in FIG. 1B. In an embodiment, the isolated or recombinant virus wherein the functionally inactivated R2 comprises a Y300 mutation such as a Y300F mutation, and/or any mutation of one or more of the following residues that causes loss or reduction of catalytic activity: W34, E38, D70, E101, H104, Y108, F167, F171, G181, I193, D196, E197, H200, Y254, and E294. In an embodiment, the deleted amino acids comprise part or all of the R1 binding domain, reducing binding to R1 by for example at least 50%, 60%, 70%, 80%, 90% or more.

The group of poxviruses that are expected to be useful include for example poxviruses that are able to infect mammalian cells, particularly human cells and which in their wild type form express a R2 gene. Accordingly in an embodiment, the wild type poxvirus comprises a R2 gene and is infectious for mammalian cells. In an embodiment, the poxvirus is infectious for human cells. Poxvirus genus' comprising an R2 gene and which are infectious for mammalian cells include for example genera listed in Table 3, such Orthopoxviruses such as Vaccinia viruses, Leporipoxviruses and Yatapoxviruses. Accordingly in an embodiment, the poxvirus is selected from Orthopoxviruses such as Vaccinia viruses, Leporipoxviruses and Yatapoxviruses. In an embodiment, the poxvirus is selected from a genus in Table 3, optionally an Orthopoxvirus, a Leporipoxvirus, a Suipoxvirus, a Capripoxvirus, a Cervidpoxvirus, a Avipoxvirus, a Molluscipoxvirus, a Parapoxvirus and a Yatapoxvirus. In another embodiment, the poxvirus is unclassified, for example a crocodilepox virus (CRV). In an embodiment, the poxvirus species is a species listed in Table 3, such as horsepoxvirus (HSPV), taterapox virus (TATV, variaola virus (VARY), swinepox virus (SPXV) etc.

Vaccinia viruses for example are useful as oncolytic agents. Vaccinia viruses, as well as many other Orthopoxviruses (e.g. ECTV), have a quick and efficient life cycle, forming mature virions in the order of 6 h and vaccinia virus spreads efficiently cell to cell thus increasing the efficacy of an in vivo infection. Vaccinia viruses can infect a wide range of human tissues and there is a large body of knowledge about its biology and extensive experience with it clinically as part of the smallpox vaccination program. Accordingly, in a preferred embodiment, the poxvirus is a vaccinia virus.

The experiments disclosed herein have been conducted in a laboratory adapted strain of vaccinia virus. A number of laboratory adapted and clinical strains are known to a person of skill in the art. For human applications, a clinical grade virus is useful. Accordingly in one embodiment, the isolated or recombinant poxvirus is a clinical grade virus. In an embodiment, the vaccinia virus strain is WR, Tian Tian, NYCBH, Wyeth, Copenhagen, Lister, MVA, Lederle, Temple of Heaven, Tashkent, USSR, Evans, Praha, LIVP, Ikeda, 1HD, Dls, LC16, EM-63, IC, Malbrán, DUKE, Acambis, 3737, CVA and AS. In an embodiment, the strain is NYCBH with the proviso that the functionally inactivated R2 gene does not encode a R2 gene deleted for 180 bp. In another embodiment the strain is Wyeth with the proviso that the functionally inactivated R2 does not encode a R2 deleted for 180 bp. In an embodiment, the isolated or recombinant vaccinia virus comprises a functionally inactivated R2 which is deleted for at least 2, at least 5, at least 10, at least 20, at least 30, at least 35, at least 40, at least 50, at least 60, at least 61, at least 70, at least 80, at least 90, at least 100, at least 110, at least 120, at least 130, at least 140, at least 150, at least 160, at least 170, at least 180, at least 190, at least 200, at least 210, at least 220, at least 230, at least 240, at least 250, at least 260, at least 270, at least 280, at least 290, at least 300, at least 310, at least 320 amino acid residues of SEQ ID NO:1. In another embodiment, the isolated or recombinant poxvirus and/or vaccinia virus comprises a functionally inactivated R2 deleted for at least 2, at least 5, at least 10, at least 20, at least 30, at least 35, at least 40, at least 50, at least 60, at least 61, at least 70, at least 80, at least 90, at least 100, at least 110, at least 120, at least 130, at least 140, at least 150, at least 160, at least 170, at least 180, at least 190, at least 200, at least 210, at least 220, at least 230, at least 240, at least 250, at least 260, at least 270, at least 280, at least 290, at least 300, at least 310, at least 320 amino acid residues, wherein the R2 is at least 80%, at least 85%, at least 90%, at least 95, at least 98%, at least 99% or more identical to SEQ ID NO:1. In an embodiment, the deletion mutant of R2 comprises deletion of at least 310 amino acid residues. In another embodiment, the deletion mutant of R2 comprises deletion of amino acid residues 1 to 310.

The deletion can also be described in terms of nucleotide positions. For example, a deletion of at least 30 amino acid residues of R2 corresponds to a deletion of at least 90 nucleotides. The deletion can also be described referring to specific genomic positions for a particular strain, e.g. WR strain. A person skilled in the art would readily be able to determine the corresponding positions in other strains. Accordingly in an embodiment, nucleotides corresponding to nucleotides 33948-32987 of WR genome are deleted. The nucleotide sequence of WR is provided for example in Genbank Accession # NC-006998, which is herein incorporated by reference.

It is also disclosed herein that additional functional inactivations, e.g. gene deletions or mutations, of other poxvirus genes such as R1 and thymidine kinase (also referred to as TK or J2R) can be combined with the R2. Accordingly in an embodiment, the virus further comprises a functionally inactivated R1 gene, thymidine kinase gene and/or vaccinia virus growth factor gene. Mutations including point mutations, dominant negative mutations and deletions that affect activity or expression levels are useful with the present methods. In an embodiment, the functionally inactivated R1 gene comprises a deletion of nucleotides 61929-64240 in the vaccinia WR genome which deletes amino acids 1-771 of I4. In another embodiment, the functionally inactivated J2R gene comprises a disruption in the J2R ORF such that an insertion is made in between nucleotides 81001 and 81002 in the WR genome which causes disruption between amino acid 92 and 93 such that only the first 92 residues of J2 are expressed.

The isolated or recombinant virus in an embodiment, preferentially replicates in neoplastic disorder cells, for example neoplastic disorder cells with increased RR levels. Cancer cells have been demonstrated to amplify RR subunit genes and can become resistant to chemotherapeutics, particularly to drugs that target RR activity such as hydroxyurea and gemcitabine. The disclosed poxviruses would as the results herein demonstrate replicate with increased efficiency in cells with increased cellular RR levels. In another embodiment, the isolated or recombinant poxvirus is oncolytic.

In another aspect, the application provides a composition comprising the isolated or recombinant virus disclosed herein, and a pharmaceutically acceptable diluent or carrier. In an embodiment, the diluent or carrier comprises phosphate-buffered saline solution. In another embodiment, the composition comprises a chemotherapeutic useful for treating neoplastic disorders with increased RR levels. In another embodiment, the composition further comprises hydroxyurea, gemcitabine and/or a nucleoside analog.

In a further aspect, the disclosure provides a vector for generating a poxvirus with a functionally inactivated R2 comprising:
  a vector backbone;
  a 5' nucleic acid comprising a 5' flanking sequence of a genomic R2 gene;
  an exchange cassette operably linked to a promoter, such as a NEO gene cassette and or a gusA gene (H5 promoter) or a mutant R2 gene; and a 3' nucleic acid comprising 3' flanking sequence of the genomic R2 gene, wherein the 5' nucleic acid is upstream of the exchange cassette and the 3' nucleic acid is downstream of the exchange cassette. In an embodiment, the distance between the start of the 5' nucleic acid and the end of the 3' nucleic acid is greater than or less than 180 nucleotides.

In an embodiment, the vector backbone is pZIPPY-NEO/GUS. A person skilled in the art will recognize that other vector backbones useful as targeting vectors comprising for example Cre-loxP site recombination technology would also be useful.

A further aspect relates to an antibody generated using ectromelia virus R2 antigen that detects ectromelia virus R2 antigen and vaccinia virus F4. In an embodiment, the antibody is a monoclonal antibody. In another embodiment, the antibody is a polyclonal antibody. Methods for making polyclonal and monoclonal antibodies are known in the art and disclosed herein.

Compositions comprising the antibody and a diluent or carrier, such as a BSA optionally in solution to stabilize the antibody, are provided in another aspect. Also compositions comprising the vector constructs described herein with a suitable diluent or carrier are provided.

iii. Methods

Disclosed herein are poxviruses comprising functionally inactivated R2 genes. These viruses are useful as oncolytic agents for inducing cell death in a neoplastic disorder cell and/or for use in treating neoplastic disorders. Accordingly in an aspect the disclosure provides a method of inducing death in a neoplastic disorder cell, the method comprising contacting the cells with an isolated or recombinant virus or composition described herein. In an embodiment, the cell is in vivo.

In another embodiment, the disclosure provides a method of treating a neoplastic disorder comprising administering an effective amount of the isolated virus or composition described herein. In an embodiment, the isolated virus is a recombinant virus. In certain embodiments, the isolated or recombinant virus described herein is oncolytic. In an embodiment, the isolated virus is a virus described herein. In an embodiment, the isolated virus is a virus described in Table 1, 2 or 3.

The isolated or recombinant viruses are useful for treating a variety of neoplastic disorders. In an embodiment, the neoplastic disorder is cancer. A number of cancers have been shown to have increased RR levels and/or are treated with chemotherapeutics that target RR. In an embodiment, the cancer is selected from breast cancer, colorectal cancer, hepatic cancer such as hepatocellular carcinoma, pancreatic cancer, skin cancer such as melanoma, esophageal cancer, leukemia, ovarian cancer, head and neck cancer, gliomas and gastric cancer.

Hydroxyurea and gemcitabine are chemotherapeutics that target RR. Accordingly in an embodiment, the cancer cell or cancer is resistant to hydroxyurea and/or gemcitabine. Use of chemotherapeutics such as hydroxyurea and gemcitabine can induce resistance. Accordingly in an embodiment, the cancer is a resistant cancer, such as a HU- and/or gemcitabine-resistant cancer. In another embodiment, the resistant cancer is resistant to hydroxyurea and/or gemcitabine.

Neoplastic disorders for example cancers can have increased RR levels as mentioned. Accordingly in an embodiment, the cancer cell or cancer comprises increased levels of ribonucleotide reductase compared to a normal cell of the same tissue type.

Increased RR levels can be reflected in increased protein, RNA and/or activity levels. For example, increased RR expression has been directly correlated with increased RR activity (9). In an embodiment, the level of ribonucleotide reductase is assessed by determining the activity level of the ribonucleotide reductase (e.g. one or more subunits, such as R2), the protein level of the ribonucleotide reductase, the RNA level of the ribonucleotide reductase or the levels of dNTPs, wherein an increase in the activity, protein, or RNA level of ribonucleotide reductase or an increase in the levels of dNTPS is indicative the cancer cell or cancer has increased levels of ribonucleotide reductase. A person skilled in the art will recognize that a number of methods, such as methods disclosed herein can be used to assess the level of RR, including for example immunoassays for protein levels, quantitative RT-PCR for RNA levels and enzyme or binding assays for activity levels or automated quantitative analysis.

The increase in the level of ribonucleotide reductase (e.g. of a subunit such as R2, or complex catalytic level) is in an embodiment, at least 10%, at least 20%, at least 30%, at least 40%, at least 50%, at least 60%, at least 70% at least 80%, at least 90%, at least 100% or greater than 100% more compared to a normal cell of the same tissue type. In another embodiment, the increase in the level of ribonucleotide reductase (e.g. cellular RR) is at least about 2 fold, at least about 3 fold, at least about 4 fold, at least about 5 fold, at least about 6 fold, at least about 7 fold, at least about 8 fold, at least about 9 fold, at least about 10 fold, at least about 15 fold, at least about 20 fold or more. The increase can for example be an increase in levels of protein, RNA and/or activity.

In certain embodiments, the subject is first assessed for neoplastic disorder RR levels. Accordingly, in an embodiment, the method comprises determining the level of RR in the cancer cell or a sample from the subject comprising cancer cells prior to administration of the isolated or recombinant virus described herein.

In an embodiment, the subject is also treated with another indicated therapy. For example, in an embodiment, the subject is also administered a chemotherapeutic. As mentioned hydroxyurea is a chemotherapeutic used to treat a wide variety of cancers, including cancers with increased RR levels. In an embodiment, the subject is also administered hydroxyurea wherein the hydroxyurea is administered prior to, contemporaneously with, or following administration of the isolated or recombinant virus or composition of the disclosure.

In another embodiment, wherein the subject is also administered a nucleoside analog, wherein the nucleoside analog is administered prior to, contemporaneously with, or following administration of the isolated or recombinant virus or composition of the disclosure. In an embodiment, the nucleoside analog is cidofovir (CDV). CDV is an antiviral compound used to treat clinical poxvirus infections under emergency situations. CDV has been to be effective at killing cancer cells. CDV, can for example be used if the replication of the oncolytic virus was deemed to be harmful to the patient and the virus had to be eliminated. As shown herein, the mutant viruses are hypersensitive to CDV and therefore would be highly amendable to such treatment.

In another embodiment, the subject is also administered gemcitabine wherein the gemcitabine is administered prior to, contemporaneously with, or following administration of the isolated or recombinant virus or composition disclosed herein.

In an embodiment, the combination therapy is administered contemporaneously. In another embodiment, the combination therapy is administered in a two-step, or consecutive type treatment. In an embodiment, the drug e.g. chemotherapeutic is first administered, and the isolated or recombinant poxvirus disclosed herein is subsequently administered for example to destroy any residual or resistant cells, for example residual tumor or resistant cancer cells.

In another embodiment, the method further comprises detecting the presence of the administered isolated or recombinant poxvirus, for example the administered vaccinia virus in the neoplastic disorder cell and/or in a sample from a subject administered an isolated or recombinant virus or composition described herein. For example, the subject can be tested prior to administration and/or following administration of the isolated or recombinant poxvirus or composition described herein to assess for example the progression of the infection. In an embodiment, the isolated or recombinant poxvirus of the disclosure comprises a detection cassette and detecting the presence of the administered isolated or recombinant poxvirus comprises detecting the detection cassette encoded protein. For example, wherein the detection cassette encodes a fluorescent protein, the subject or sample is imaged using a method for visualizing fluorescence.

A further aspect includes use of an isolated or recombinant virus or a composition described herein to induce death in a neoplastic disorder cell such as a cancer cell or to treat a neoplastic disorder such as cancer.

A further aspect includes an isolated poxvirus comprising a functionally inactivated R2 gene or a composition comprising the isolated poxvirus for use in inducing death in a neoplastic disorder cell and/or for use in treating a neoplastic disorder.

The above disclosure generally describes the present application. A more complete understanding can be obtained by reference to the following specific examples. These examples are described solely for the purpose of illustration and are not intended to limit the scope of the application. Changes in form and substitution of equivalents are contemplated as circumstances might suggest or render expedient. Although specific terms have been employed herein, such terms are intended in a descriptive sense and not for purposes of limitation.

The following non-limiting examples are illustrative of the present application:

EXAMPLES

Example 1

Results

Generation of ribonucleotide reductase vaccinia mutants. In order to investigate the genetic requirement of the genes encoding the small (F4L) and large (I4L) subunits of the VACV ribonucleotide reductase (RR) for viral replication, a series of mutant VACV strains were generated in which one (ΔI4L; ΔF4L) or both (ΔI4L/ΔF4L) of these viral RR genes were deleted from the WR genome (FIG. 1A; see materials and methods for detailed descriptions of virus construction). Given that RR complexes are involved in the de novo pathway of dNTP biogenesis and VACV encodes a thymidine kinase (J2R) involved in the alternative and complementary salvage pathway, it was decided to determine if insertional inactivation of the J2R locus would exacerbate any possible phenotypes of the RR deletion strains. Therefore, inactivation of J2R was carried out in some of the RR mutant backgrounds to generate ΔI4L/ΔF4L/ΔJ2R and ΔF4L/ΔJ2R strains. In some cases, a $His_5$-tagged F4L gene or a $His_6$-tagged F4L gene encoding the amino acid substitution Y300F was inserted into the J2R locus of ΔF4L strains. Y300 represents a highly-conserved tyrosine residue found in essentially all mammalian RR small (R2) subunits (FIG. 1B). The homologous residue in mouse R2 (Y370) is required for the transfer of radicals in between the large (R1) and small subunits which is required for catalysis (30). Substitution of Y370 for phenylalanine abolishes catalysis but does not impede physical interaction of R2 with R1 (30). Substitution of the homologous residue in human p53R2 (Y331) with phenylalanine also abolishes RR activity of p53R2/R1 complexes (43). Therefore the Y300F substitution in F4 is predicted to inactivate the radical transfer pathway between small and large RR subunits while maintaining the capacity of these subunits to interact.

PCR amplifications with primers specific to the region of the WR genome that was altered in each mutant were used to confirm the deletion or inactivation of the targeted loci. The results of these experiments for the major strains disclosed herein are shown in FIG. 1C along with model diagrams depicting the approximate binding sites of the primers for each type of PCR reaction. Primers specific for a region of the viral DNA polymerase gene (E9L) were used as a positive control for amplification off of the various viral DNA templates. The primers used for analysis of I4L and F4L loci only amplify fragments of these loci if the respective ORFs are intact. Amplification of I4L PCR products was only apparent in those strains not transfected with the I4L knockout vector (FIG. 1C). Likewise, F4L PCR reactions confirmed the presence of F4L sequence in only those strains not transfected with the F4L knockout vector (FIG. 1D). The primers for J2R locus analysis bind to sequences flanking the site of insertion of the pSC66 vector (see materials and methods). Therefore, intact J2R loci give rise to small (~0.5 kb) PCR products whereas insertion of the lacZ gene (and flanking sequences) from pSC66 produces a much larger (~4 kb) product. In those cases where the pSC66 vector contained a cloned F4L gene the PCR product increases in size to ~5 kb due to the ~1 kb of sequence of the F4L ORF. All J2R PCR amplifications produced products of the expected size within each construct confirming the integrity or insertional inactivation of the J2R gene (FIG. 1C). Western blotting confirmed the presence or absence of the viral RR subunits in each of the isolates (FIG. 1D). Although equal amounts of protein were loaded in each lane, the strain expressing a wild-type F4L gene in the J2R locus appeared to have elevated levels of F4 compared to wild-type virus whereas the strain expressing the Y300E-substituted F4L gene was observed to have slightly reduced F4 expression (FIG. 1D). The former case is likely a result of the F4L gene being under the control of a strong early/late promoter whereas the endogenous F4L promoter is activated only at early times during infection (29). The lower F4 expression of the point-mutant is likely reflective of the generally-reduced replicative capacity of this virus (see below). These and other VACV strains are summarized in Table 1. See Materials and Methods for details of virus construction.

Characterization of plaque morphology and size of ribonucleotide reductase vaccinia mutants. As an initial step to characterize the growth properties of the viruses described in FIG. 1, plaque size and morphology of these strains was analyzed on BSC-40 cells. Wild-type and ΔI4L strains had similar plaque morphologies with large clearings in the center of plaques and primary plaques were typically closely associated with smaller, secondary plaques likely arising from the release of extracellular enveloped virus from the larger primary plaque sites (FIG. 2A). Quantitative analysis of plaque areas also indicated no statistically significant differences between wild-type and ΔI4L strains (FIG. 2B). In contrast, viruses with F4L or F4L and J2R deleted presented with significantly smaller plaques (p<0.05) than wild-type virus with mean plaque areas only 55-60% that of wild-type. Furthermore, these primary plaques were typically devoid of nearby secondary plaques unlike wild-type and ΔI4L strains.

However, ΔF4L/ΔJ2R strains expressing a His$_6$-tagged F4 protein from the J2R locus (ΔF4L/ΔJ2R$^{HisF4L}$) displayed plaques characteristic of wild-type virus in terms of size and the presence of secondary plaques. Strikingly, strains encoding the Y300F substitution produced plaques that were not only significantly smaller (p<0.05) than wild-type virus (FIG. 2B) but upon further analysis, were also 35-40% the size of all other ΔF4L strains and these differences were statistically significant (p<0.05). These results suggest that deletion of F4L has a more detrimental effect on plaque size than deletion of I4L. It further suggests that re-introduction of a His$_6$-tagged F4L gene into the J2R locus can rescue this smaller plaque phenotype of the ΔF4L strains. However, expression of the Y300F F4 protein appears to more severely inhibit plaque formation even compared to strains missing both RR subunit genes and the viral thymidine kinase gene.

We also tested the ability of other, His$_6$-tagged Chordopoxvirus or host R2 proteins to rescue the small plaque phenotype of the ΔF4L strain. The R2 genes encoded by ECTV, MYXV and SFV R2 genes were all able to rescue the small plaque phenotype, but interestingly the Hp53R2 gene failed to rescue this phenotype (FIG. 2B). These results implied that Chordopoxvirus R2 proteins have conserved a specific function and/or activity level that is not recapitulated by Hp53R2.

Characterization of replication capacities of ribonucleotide reductase vaccinia mutants. To explore the growth kinetics of these RR mutants further, growth curves were conducted in HeLa cells. As previously reported (6), deletion of I4L had little effect on total virus yields after 48 h of replication with the wild-type strain replicating to titers only 2-fold higher than the ΔI4L strain (FIG. 2C). In contrast, differences between wild-type and ΔF4L strains were readily apparent by 18 h post-infection and this trend continued to the end of the experiment such that wild-type titers were ~15-50-fold higher than ΔF4L strains (FIG. 2C). Re-introduction of the F4L gene into the J2R locus appeared to rescue the replication defects observed in F4L strains as this virus replicated similarly to the ΔI4L strain. In contrast, introduction of the Y300F substituted F4L gene inhibited productive replication over the course of the experiment (FIG. 2D). These results suggest that deletion of the F4L gene impairs vaccinia replication to a higher degree than deletion of I4L and that concomitant deletion of F4L and J2R does not appear to have any synergistic effects on the replicative capacities of vaccinia in cell culture. Furthermore the observation that introduction of a wild-type F4L gene into the J2R locus can rescue the growth defect of ΔF4L strains suggests that the observed defect of the ΔF4L is due to the lack of F4 expression and not to other possible idiosyncratic effects of deleting the F4L locus. Finally, the fact that the strain expressing the Y300F F4 protein has more severely reduced replication capacity than viruses lacking both RR subunits suggests that the Y300F mutant may act as a dominant negative. If F4 protein normally binds to other cellular (and viral) R1 subunits and forms functional complexes during infection then the Y300F F4 protein would be predicted to form inactive complexes upon binding, preventing these R1 subunits from interacting with endogenous cellular R2 proteins. Introduction of the Y300F F4L gene into the J2R locus of ΔI4L/ΔF4L strains also leads to production of small plaques that are similar in size to those found in the ΔF4L/ΔJ2R$^{HisY300FF4L}$ strain (FIG. 2B) suggesting that the absence of I4L in these strains does not preclude the Y300F mutant from exerting its negative effects on replication.

The results disclosed herein suggest that the ΔF4L strains were impaired in their ability to replicate compared to wild-type virus. This is because RR plays a key role in dNTP biogenesis and our initial studies found that ΔF4L (FIG. 11A), but not ΔI4L strains (FIG. 11B), exhibited reduced late gene expression, which is common consequence of defects in DNA replication. In order to determine if this reduced viral replication may be the result of delayed or reduced genome replication, BSC-40 cells were infected with either wild-type or the ΔF4L strain to track the progression of viral progeny production and genome replication in parallel experiments. In order to determine if reduced genome replication may be a result of decreased RR activity, treatments in which wild-type or ΔF4L culture media contained the RR inhibitor HU were included because resistance to RR inhibitors is correlated with higher RR expression (33). The results of these experiments are shown in FIG. 3. As observed previously, the ΔF4L had impaired replication kinetics generating only 15% of the total virus observed for the wild-type strain at 24 h post-infection (FIG. 3A). Analysis of viral genome replication also indicated delayed DNA replication kinetics of the ΔF4L strain with genomic DNA only being detectable at 9 h post-infection compared to wild-type infections in which DNA was detected as early as 6 h. Even after 24 h of infection, the ΔF4L strain still had only replicated genomic DNA to ~18% the level of wild-type virus. Furthermore, addition of 0.5 mM HU to ΔF4L cultures prevented the detection of genomic DNA throughout the entire 24 h infection period whereas wild-type virus produced detectable genomic DNA albeit with delayed kinetics and at reduced quantities much like the ΔF4L strain in the absence of HU (FIG. 3B). Comparison of FIG. 3B & A suggest that peak replication of the ΔF4L occurred between 9 and 12 h post-infection as this is when the largest increase in viral titers as well as genome replication is observed. In contrast, the wild-type strain undergoes large increases in titers and genome replication earlier, between 6 and 9 h post-infection and then again between 18 and 24 h post-infection, with this second increase essentially absent in the ΔF4L infections. These results suggest that the impaired replication of the ΔF4L strain may be at least partially due to reduced genome synthesis and the hypersensitivity of this strain to HU suggests that these infections experience reduced total RR activity which is directly correlated to RR protein expression levels, which in turn correlates with sensitivity to RR inhibitors (9).

ΔF4L strains are uniquely hypersensitive to cidofovir and HU. The previous studies suggested that the lower replication capacity of the ΔF4L strains may be due to reduced genome replication. However, it is difficult to interpret the meaning of biochemical measurements of pool sizes because of uncertainties surrounding how dNTPs are distributed in infected cells. Instead, we tested whether VACV RR mutants exhibit an altered sensitivity to the antiviral drug cidofovir (CDV). CDV is converted by cellular kinases to the diphosphoryl derivative (CDVpp) [8] which is competitive with respect to dCTP (45) and inhibits VACV E9 DNA polymerase activity (46, 47). Thus, CDV sensitivity can be used as an indirect probe for changes in dCTP pool sizes. Table 2 summarizes how RR mutations affect CDV sensitivity as assessed by plaque reduction assays and calculated 50% effective concentration (EC$_{50}$) values. Wild-type and ΔF4L/ΔJ2R$^{HisF4L}$ strains exhibited similar mean EC$_{50}$ values of 42.0 and 41.2 µM, respectively. The ΔI4L strain was significantly more sensitive than the aforementioned strains (P<0.05) having a mean EC$_{50}$ value of 25.1 µM. However, loss of F4L (or F4L and J2R) resulted in greater hypersensitivities to CDV (P<0.05) with EC$_{50}$ values ~5-7-fold lower than wild-type values. The ΔF4L/ΔJ2R$^{HisY300FF4L}$ virus was even more sensitive to CDV (EC$_{50}$=3.5 µM) than either wild-type (P<0.05) or ΔF4L (P<0.05) strains. As noted previously (21, 48), inactivation of J2R did not further alter VACV sensitivity to CDV (Table 2). The trends in CDV sensitivity closely mirrored those found in measurements of HU sensitivity using a plaque reduction assay (Table 2). The order of resistance to HU (from measurements of $EC_{50}$) was wild-type ≥ΔF4L/ΔJ2R$^{HisF4L}$>ΔI4L>ΔF4L>ΔF4L/ΔJ2R$^{HisY300FF4L}$ and seemed unaffected by the presence or absence of the J2R gene (Table 2). In order to determine if the hypersensitivities of ΔF4L and ΔF4L/ΔJ2R$^{HisY300FF4L}$ strains to CDV and HU were specific and not simply due to the reduced replicative abilities of these viruses, we performed a plaque reduction assay using phosphonoacetic acid (PAA). PAA is a pyrophosphate analog and DNA polymerase inhibitor that is noncompetitive with dNTPs (49). Therefore, the efficacy of PAA in inhibiting virus replication would not be expected to be dependent upon RR activity or dNTP pool sizes. Consistent with this, RR mutant VACV strains were not hypersensitive to PAA when compared to wild-type virus (Table 2). These mutant strains were also not hypersensitive to isatin-β-thiosemicarbazone (IBT), which causes aberrant late viral mRNA biogenesis (50). Collectively, these data all point to a deficiency in dNTP pools as being the cause of the ΔF4L strain growth deficiency (FIG. 2) and suggest that F4, is the critical determinant of growth efficiency and drug sensitivity.

Immunoprecipitation of vaccinia and human ribonucleotide reductase subunits. The observation that ΔF4L strains were more inhibited in terms of plaque morphology and growth kinetics than ΔI4L strains is striking considering that F4 and I4 must interact with each other to form active RR complexes. The reduced DNA replication and hypersensitivity of ΔF4L strains to CDV further suggested an inherit defect at the level of genome replication. A possible explanation for these observations is that F4 may form functional RR complexes with cellular R1 proteins which normally contribute to the establishment of sufficient dNTP pools for viral replication. Previous observations using purified mouse RR proteins demonstrated both F4 and I4 could interact with large and small mouse RR subunits, respectively and form catalytically-active enzymes (7). Interestingly, an F4-mouse R1 complex was more active than F4-I4, mouse R2-mouse R1, or I4-mouse R2 complex (7). In order to investigate the possibility of complex formation between F4 and cellular ribonucleotide reductase proteins, immunoprecipitations were performed in wild-type virus-infected HeLa cells using antibodies against endogenous HR1, HR2 or Hp53R2 RR subunits. Interestingly, F4 was co-immunoprecipitated in each of these cases but not with control antibodies (FIG. 4). These results suggest that F4 physically interacts with endogenous levels of all three of the human RR subunits including HR1, HR2 and Hp53R2. Interaction of F4 with cellular R2 subunits was unexpected. It was not previously known that R2 subunits from vaccinia could interact with cellular R2 proteins and was unexpected. We thought these interactions may be in part due to enhanced cellular RR subunit expression after infection. However, we were unable to observe induction of cellular RR expression by 24 h post-infection (FIG. 12). To further confirm these results, VACV strains expressing either Flag-tagged HR1 (ΔJ2R$^{FlagHR1}$) or Flag-tagged I4 (ΔI4L/ΔJ2R$^{FlagI4L}$) were constructed and used in new immunoprecipitation experiments. Immunoprecipitation with anti-Flag antibodies confirmed the interaction of HR1 and I4 with F4 as well as with HR2 and Hp53R2 (FIG. 5A). Weaker bands were typically observed in the immunoprecipitations of Flag-tagged HR1 compared to Flag-tagged I4 despite similar amounts of these proteins being immunoprecipitated (FIG. 5A). This result is likely due to competition between the Flag-HR1 protein and endogenous HR1 whereas in Flag-I4 is expressed from a ΔI4L strain and thus does not have to compete for binding to R2 proteins with endogenous I4. We also prepared extracts from cells infected with ΔF4L/ΔJ2R$^{HisY300FF4L}$ or ΔF4L/ΔJ2R$^{HisF4L}$ viruses and observed that these $His_6$-tagged proteins could also be co-immunoprecipitated with HR1 protein (FIG. 5B). Reciprocal co-immunoprecipitation experiments confirmed an interaction between F4 and HR1 proteins (FIG. 13). These results confirm that human and viral RR subunits interact within infected cells.

Other Chordopoxvirus R2 proteins rescued the replication defect of VACV ΔF4L strains (FIG. 2B). Therefore, we determined whether these proteins could also interact with HR1. ECTV, MYXV, and SFV R2 proteins all co-immunoprecipitated with HR1 (FIG. 5B). Although there appeared to be differences in the efficiency of HR1 association, western blotting of lysates showed that this reflected differences in R2 expression levels (FIG. 5B). These results confirm that RR subunits from poxviruses that infect a diversity of mammalian hosts have conserved the capacity to interact with HR1.

Localization of viral and human ribonucleotide reductase subunits during vaccinia infection. Previous studies have demonstrated an exclusively cytoplasmic distribution of mammalian RR proteins in uninfected cells (13, 14, 27). Confocal microscopy studies with antibodies directed against endogenous (FIG. 6A) or epitope-tagged (FIG. 6B) RR subunits suggested that VACV infection did not alter host RR localization and VACV RR subunits were also found to exhibit a similar cytoplasmic distribution. These results support the immunoprecipitation data in that both viral and human RR proteins are found within the same general cellular compartment (the cytoplasm) during infection where they have the possibility of interacting.

Requirement of C-Terminal residues of F4 for interaction with HR1. The previous studies showed that F4 interacts with HR1 but did not prove whether such an interaction was essential for viral replication. Numerous structural and peptide-inhibition studies of class I RR proteins have identified a C-terminal peptide (boxed in FIG. 1B) in R2 subunits as critical for interaction with R1 proteins [11, 57, 58, 59, 60, 61]. Since this C-terminal peptide is well conserved in F4 (FIG. 1B), we speculated that HR1-F4 interactions were also dependent on this peptide. To test this hypothesis, we generated the VACV strain ΔF4 L/ΔJ2R$^{HisF4L\Delta R1BD}$, encoding a truncation mutant of F4 that lacks the C-terminal seven residues representing the putative R1-binding domain (R1BD). We also generated an R1BD mutant that also encodes the Y300F substitution, (ΔF4L/ΔJ2R$^{HisY300FF4L\Delta R1BD}$). As shown in FIG. 7A, $His_6$-tagged F4 co-immunoprecipitated with HR1 in HeLa cell extracts. However, there was a clear reduction (by ~90%) in co-immunoprecipitation of $His_6$-tagged F4 proteins lacking the R1BD, despite comparable levels of these two forms of F4 in lysates and immunoprecipitates. Thus, F4 appears to have conserved the R1-binding peptide encoded by class I RRs.

We used plaque area measurements to determine if deleting the $R^1$BD would alter VACV plating properties (FIG. 7B). The control viruses exhibited the same relative plaque sizes noted previously (i.e. wild-type=ΔF4L/ΔJ2R$^{HisF4L}$>ΔF4L>ΔF4L/ΔJ2R$^{HisY300FF4L}$) and the differences were all significant (P<0.05). However, the ΔF4L/ΔJ2R$^{HisF4L\Delta R1BD}$ and ΔF4L/ΔJ2R$^{HisY300FF4L\Delta R1BD}$ strains produced plaques no different in size from those produced by ΔF4L strains (P>0.05). This suggested that the F4 R1BD was not only required for RR activity, but that the HR1-F4 interaction was also responsible for the dominant negative effects observed with strains encoding the Y300E-substituted F4 protein with an intact R1BD. We also confirmed in these studies that inactivation of J2R alone had no significant effect on plaque size (FIG. 7B).

Replication of ribonucleotide reductase mutant vaccinia strains in pancreatic cancer cell lines. Based on the results previously described it was predicted that if the defect in replication of the ΔF4L strains was due to reduced total ribonucleotide reductase activity in infected cells (and subsequent lower dNTP pools) then the growth of these strains should be enhanced in cell lines over-expressing cellular RR subunits and impeded in cells that have low levels of cellular RR expression. PANC-1 and Capan-2 cells are pancreatic cancer cell lines that have been previously reported to have high and low levels, respectively of RR subunit expression (9, 10). In order to confirm these results and to ensure that these results were also true of infected cultures, western-blots were performed on lysates prepared from mock or wild-type-infected cultures of PANC-1 and Capan-2 cells (FIG. 8A). The results clearly show the reduced expression of HR1, HR2, and Hp53R2 in Capan-2 cells relative to PANC-1 cells, and this was true in both mock and VACV-infected cultures. Therefore, approximately equal numbers of PANC-1 and Capan-2 cells were seeded into culture dishes and were infected with wild-type and the various RR mutant strains. The total titers for each of these infections at 48 h or 72 h post-infection are plotted in FIG. 8B. All strains clearly replicated more poorly on Capan-2 cells compared to the PANC-1 cells. Division of the mean titers obtained in PANC-1 cells by those obtained in Capan-2 cultures for each virus gave an estimate of the fold difference in replication efficiencies of each strain in these cells (FIG. 8C). After 48 h of infection the wild-type, ΔI4L, and ΔF4L/ΔJ2R$^{HisF4L}$ strains had titers that were 6-8-fold higher in PANC-1 cells than in Capan-2 cells. However, virus strains lacking ΔF4L exhibited greater enhances in replication with 18-30 fold increases in viral titers in PANC-1 cells. The strain expressing the Y300F substituted F4 clearly benefited the most from replication in PANC-1 cells with a 113-fold increase in titers in PANC-1 cells compared to Capan-2 cells. Results at 72 h post-infection had similar trends (FIG. 8C). These data suggest that the replication defect of ΔF4L strains are at least partially rescued in PANC-1 cells. For example, the ΔF4L, and ΔI4L/ΔF4L, and ΔF4L/ΔJ2R strains had only ~3-6-fold lower titers than wild-type virus in PANC-1 infections while these same strains had 13-15-fold lower titers than wild-type in Capan-2 cells (FIG. 8A). The ΔI4L/ΔF4L/6,J2R replicated more poorly than other ΔF4L strains (~16-fold lower titers than wild-type in PANC-1 cells) suggesting that in the absence of F4 and J2, I4 may provide an important contribution to viral replication. Collectively, these results suggest that the replication defects of the ΔF4L and ΔF4L/ΔJ2R$^{HisY300FF4L}$ strains can at least be partially rescued in human cancer cell lines over-expressing cellular RR subunits.

VACV nucleotide metabolism genes are required for replication in human primary cells in low serum conditions. In order to further test the correlation of cellular RR expression and rescue of RR mutant virus replication, we infected human primary cells with an array of VACV mutants lacking one or more nucleotide metabolism-related genes. When cells were cultured under high serum conditions, which stimulates cell replication, most VACV strains productively replicated within 72 h with the wild-type, ΔI4L, ΔF4L/ΔJ2R$^{HisF4L}$, and ΔJ2R strains all replicating to similar titers that were ~10-fold higher than ΔF4L strains. The ΔF4L/ΔJ2R$^{HisY300FF4L}$ strain failed to replicate under these conditions (FIG. 9A). In contrast, under serum starvation conditions in which cells enter quiescence and have limited replication, the wild-type virus replicated to ~100-fold higher titers than most VACV strains and to levels similar to that observed in high serum conditions. In fact, ΔF4L and ΔF4L/ΔJ2R$^{HisY300FF4L}$ strains failed to replicate. Furthermore, I4L, ΔF4L/ΔJ2R$^{HisF4L}$, and ΔJ2R strains exhibited a delayed and reduced replication phenotype, yielding only a 10-fold increase in titers by 72 h post-infection (FIG. 9B). These data indicate that under high serum conditions ΔF4L strains still exhibit a replication defect but this phenotype is exacerbated when cells are cultured under low serum conditions. Since serum is known to stimulate cell replication and since cellular nucleotide metabolism machinery such as RR is cell cycle-regulated, we performed western blotting to determine if levels of cellular RR subunits were different between high and low serum conditions. Both HR1 and HR2, which are expressed in an S-phase-specific manner, were more abundant in high serum conditions compared to serum starvation treatments. Hp53R2, which is not cell cycle-regulated, was found at similar levels in both serum conditions (FIG. 9C). These results suggest that the rescue of RR mutant virus strains under high serum conditions correlates with increased abundance of cellular R1 and R2 subunits and in their absence, these mutant strains are unable to replicate.

VACV RR subunits are differentially required for pathogenesis in mice. We used an animal model to determine if the apparent differential requirement for VACV RR subunits for replication in culture would be recapitulated in vivo. We infected groups of five NMRI mice with equal doses of wild-type, ΔI4L, ΔF4L, or ΔI4L/ΔF4L strains and tracked changes in animal body weight over 24 days. The wild-type and ΔI4L strains exhibited a similar degree of virulence, causing the death of 5/5 and 4/5 animals, respectively, within seven days of infection. In contrast, both ΔF4L and ΔI4L/ΔF4L strains were highly attenuated, with all animals displaying little to no signs of disease and surviving the infections (FIG. 10A). There were small, transient drops in body weight for animals infected with the ΔF4L strain around days 5 and 7, otherwise these animals, and those infected with the ΔI4L/ΔF4L strain, showed no obvious signs of morbidity when compared to the mock-infected control group (FIG. 10A). To obtain a more quantitative measurement of the pathogenic nature of these infections, we isolated lung tissues from mice infected with the aforementioned strains on day 5 post-infection. Wild-type and ΔI4L strains clearly had a replication advantage over ΔF4L and ΔI4L/ΔF4L strains with lung titers approximately 4 logs higher than the latter two strains (FIG. 10B). These results indicate that VACV RR subunits are differentially required for virulence in mice.

Discussion

Contribution of F4 and I4 to vaccinia replication. The observation that deletion of F4L is more detrimental to both plaque formation and virus yields than deletion of I4L suggested that F4 is more important for the replication of vaccinia than I4 (FIG. 2). Early studies of vaccinia RR proteins found that insertional inactivation of I4L in strain WR did not cause observable defects in replication in culture and only mildly-attenuated these viruses in mouse models with an approximate 10-fold increase in lethal dose 50 values for this ΔI4L strain compared to wild-type virus (6). Another study made a partial deletion of F4L in the NYCBH vaccinia strain, as well as the Wyeth vaccine strain, in an effort to obtain alternative vaccine strains with suitable replication and virulence properties (23). This study found that their F4L mutant replicated comparable to wild-type virus in cell culture in contrast to the findings disclosed herein (23). This observation may be in part due to the high multiplicity of infection (MOI) used in their growth analyses (i.e. an MOI of 10) since high MOI values would severely limit the replication of the virus in cell culture and so differences between a wild-type and mutant strain would be minimized and may go unnoticed. Our lower MOIs (i.e. MOI of 0.03) provide growth analyses that are more sensitive to the detection of mutant strain growth defects because the virus must undergo multiple rounds of infection and replication and with each replication cycle defects become exacerbated and easier to detect. Also, as the authors did not provide RT-PCR or western blot data to show that expression of R2 (F4) is abolished or altered in the virus therefore it cannot be said with certainty that their deletion mutant actually inactivated the R2 (F4L) locus in the virus.

The detailed analysis of the ΔI4L and ΔF4L strains of this disclosure suggest that ΔF4L strains are likely more attenuated in their replication than ΔI4L strains. The observation that the Y300F F4 mutant attenuates VACV replication more severely than deletion of both F4L and I4L (FIG. 2) suggests that it inhibits dNTP production in the cell by forming inactive RR complexes with cellular RR proteins. This prediction is supported by co-immunoprecipitation of Y300F F4 with HR1 (FIG. 5). This result would be predicted to be achieved with any catalytically inactivating mutation of F4 that still allows for interaction with cellular RR subunits. For example, substitutions in conserved, catalytically-important residues such as other residues (besides Y300) involved in the radical transport pathway [FIG. 1B; (5)] between small and large subunits would be expected produce similar phenotypes in F4L-mutant viruses. The increased efficacy of these catalytically-inactive R2 subunits which interact with host R1 proteins to inhibit VACV replication is supported by the observation that the R1BD, which is required for interaction with host R1 (FIG. 7A) is also required for the smaller plaque phenotype of virus encoding the Y300F F4 protein (FIG. 7B), compared to ΔF4L.

This may explain why besides Orthopoxviruses and Suipoxviruses, most other Chordopoxvirus genera contain poxviruses that only encode an R2 subunit and not an R1. In fact, recently it was found that horsepoxvirus (an orthopoxvirus) contains a fragmented R1 gene but an intact R2 gene (37). Conservation of viral R2 genes may reflect the differential regulation of mammalian R2 and R1 protein levels during the cell cycle with R2 proteins degraded in late S-phase while R1 protein levels remain constant throughout the cytoplasm (3, 12). Although mammalian cells also encode an alternative R2 subunit, p53R2, this subunit is found only at low levels throughout the cell-cycle (38). Therefore, co-evolution of poxviruses with their host may have selected for conservation of R2 proteins in order to complex with the relatively abundant cellular R1 proteins. The immunoprecipitation (FIGS. 4, 5 & 7) data provide direct evidence that viral and cellular RR subunits interact during infection. Furthermore, previous biochemical studies have shown that mouse and vaccinia RR subunits can form functional RR complexes in vitro (7), providing further support to the prediction that poxvirus R2 subunits in general interact and form functional complexes with cellular R1 proteins. Based on our findings with VACV, ECTV, MYXV, and SFV R2 proteins, it is predicted that other poxvirus R2 proteins will exhibit similar functions. The increased hypersensitivity of ΔF4L strains to CDV compared to ΔI4L strains (Table 2) further suggests that F4 is more important in the establishment of proper dNTP pools to support viral replication.

Oncolytic potential of RR mutant poxviruses. The rescue effect of human cancers cells over-expressing cellular RR proteins on ΔF4L and Y300F F4-expressing strains (FIG. 8) predicts that any human cancer type with enhanced RR expression will be highly susceptible to treatment with ΔF4L or Y300F F4-expressing strains. We observed in FIG. 2B that Hp53R2 did not rescue the ΔF4L phenotype so overexpression of Hp53R2 alone may not be sufficient to allow for fulminant replication of the ΔF4L strain however this was only tested in one cell type. Hp53R2 does not appear to form as active a complex with host R1 proteins as host R2 therefore this may explain why Hp53R2 overexpression is not sufficient to rescue growth of ΔF4L strains. Because both an R1 and R2 subunit are required for RR activity, it is predicted that the rescue effect of host RR expression on ΔF4L strain replication will be dependent upon a subsequent increase in RR activity in the cell. Therefore if a single subunit (i.e. HR2) that is normally limiting to host RR complex formation is overexpressed in cancer tissue then this would likely support mutant virus replication since the levels of HR1 are not normally saturated with HR2 in normal tissue. Furthermore, normal human primary cells do not support productive replication of ΔF4L strains when in low serum conditions (FIG. 9). Since low serum conditions cause primary cells to arrest in the cell cycle and enter quiescence, these conditions mimic what would be found in mammalian tissue where most cells are in a highly differentiated and quiescent state. These results suggest that ΔF4L strains would be highly selective for transformed tissue and would be unable to replicate in normal tissue in vivo. The lack of replication of ΔF4L strains in mice further supports this conclusion (FIG. 10). Other poxviruses besides VACV that possess an R2 gene and are able to replicate in human cancer cells are also predicted to display this phenotype of dependence upon cellular RR levels in the absence of the viral R2 gene. Several other poxviruses that only encode an R2 subunit (Table 3) have been shown to infect human cancer cells including Avipoxviruses [e.g. canarypoxvirus; (16, 20)], Leporipoxviruses [e.g. myxoma virus; (35, 41)] and Yatapoxviruses [e.g. Yaba-like disease virus; (17)], although only the latter two groups undergo productive replication, infections of human tumors with non-replicating recombinant canarypox vectors can be used to deliver foreign genes that elicit strong anti-tumoral immune responses. Deletion and/or catalytic inactivation of the R2 gene in poxviruses that productively replicate in mammalian cells would be predicted to make these viruses even more selective for human neoplasms with enhanced RR expression. The observation that MYXV and SFV R2 proteins can rescue ΔF4L strain replication (FIG. 2B) and interact with host R1 proteins (FIG. 5B) support the conclusion that other poxyiral R2 proteins perform a similar role as VACV F4 and that deletion and/or catalytic inactivation of these genes in other poxviruses would be expected to give rise to viruses with similar properties as VACV ΔF4L strains (e.g. enhanced oncolysis). Furthermore, our growth analyses and mouse pathogencity data show that inactivation of both I4L and F4L produces a similar phenotype as a ΔF4L strain, strengthening the argument that it is poxvirus R2 genes that are the critical determinants of replication efficiencies and not poxvirus R1 genes.

Susceptibility of human cancer types to RR mutant oncolytic poxviruses. A wide variety of human cancer cell lines and clinical isolates have been shown to display either elevated RR mRNA or protein levels (see Table 4 for examples and references), suggesting that F4L mutant strains such as ΔF4L and Y300F F4-expressing strains may be useful in the treatment of a broad range of human tumor types. These tumor types include but are not limited to breast, pancreatic, colorectal, hepatic, esophageal and skin. Furthermore, HU is widely used to treat leukemia, ovarian cancers, and head and neck cancers (25, 31, 42), suggesting that these tumor types also exhibit elevated RR activity and would be amendable to treatment with the aforementioned oncolytic poxviruses. In fact, prolonged treatment of patients with RR inhibitors such as gemcitabine can lead to drug resistance often a result of HR2 gene amplification and subsequent over-expression of HR2 (28, 34, 42). Therefore, F4L mutant strains such as the ΔF4L and Y300F F4-expressing strains could form a logical component of combined therapy whereby patients are first treated with HU (or gemcitabine) followed by treatment with one of these oncolytic VACV strains to target remaining drug-resistant tumor tissue. Indeed combination therapy of RR inhibitors and other oncolytic viruses have had promising results (2, 40) supporting the efficacy of combining RR inhibitors with F4L mutant strains, such as the ΔF4L and Y300F F4-expressing strains. With the development of rapid RT-PCR and automated quantitative analysis for the detection of increased cellular RR expression in human cancers, patient biopsies could potentially be pre-screened to determine if a particular tumor tissue may respond well to oncolytic treatment (22). Therefore, poxvirus RR mutant viruses are predicted to highly effective oncolytic agents in a broad range of human cancer types.

Materials and Methods

Cell and virus culture. Cell and virus culture methods have been described elsewhere (1). Wild-type vaccinia virus (VACV) and its mutant derivatives were derived from a stock of VACV (strain WR) originally acquired from the American Type Culture Collection (ATCC). Non-transformed African Green Monkey kidney cells (BSC-40) were normally cultured in modified Eagle's medium (MEM) supplemented with 5% fetal bovine serum (FBS). HeLa human cervical adenocarcinoma cells were cultured in Dulbecos MEM (DMEM) supplemented with 10% FBS. Panc-1 and Capan-2 cells are human pancreatic epithelioid carcinoma and adenocarcinoma lines, respectively and were also cultured in DMEM supplemented with 10% FBS. All cell lines were originally obtained from ATCC. Cells were cultured in Opti-MEM media (Invitrogen) in experiments requiring transfections. All the cells disclosed herein tested negative for mycoplasma.

Materials. Cidofovir [(S)-1-(3-hydroxy-2-phosphonyl-methoxypropyl)cytosine (HPMPC)] was obtained from Gilead Sciences (Foster City, Calif.). Hydroxyurea (HU) was obtained from Alfa Aesar (Ward Hill, Mass.). X-gal and X-glu substrates were obtained from Sigma Chemical Co. (St. Louis, Mo.) and Clontech (Palo Alto, Calif.), respectively. Mycophenolic acid (MPA) and Xanthine were obtained from Sigma Chemical Co. Hypoxanthine was obtained from ICN Biomedicals, Inc. (Aurora, Ohio). Compounds were diluted to their final concentration in MEM (Cidofovir; HU) or in a 1:1 mixture of MEM and 1.7% noble agar (X-gal; X-glu) immediately prior to use. Taq and PfuUltra™ DNA polymerases were obtained from Fermentas (Burlington, ON) and Stratagene (La Jolla, Calif.), respectively.

Antibodies, western blotting, and immunoprecipitation. Normal goat serum and goat polyclonal antibodies against human R1 (HR1), human R2 (HR2), and Human p53R2 (Hp53R2) were from Santa Cruz Biotechnology, Inc. (Santa Cruz, Calif.). Mouse monoclonal antibodies against HR1 and HR2 were from Millipore (Billerica, Mass.) and Santa Cruz Biotechnology, Inc., respectively. Mouse monoclonal antibodies against Flag and $His_6$ epitopes were from Sigma and Roche (Mississauga, ON), respectively. Rabbit anti-Flag epitope polyclonal antibodies were obtained from Sigma. A mouse monoclonal antibody against recombinant ectromelia virus R2 antigen was developed and the resulting antibody also recognizes VACV F4, and was used for western-blotting (described below). A rabbit anti-I4 polyclonal antibody was obtained from Dr. C. Mathews (Oregon State University). Although this antibody recognizes VACV I4, it also cross-reacts with HR1 on western blots. The mouse monoclonal antibody against VACV I3 has been described (24) and the mouse monoclonal antibody against cellular actin was from Sigma.

Protein extracts for western blots and immunoprecipitations were prepared from cell cultures by lysing cells on ice in a buffer containing 150 mM NaCl, 20 mM Tris (pH 8.0), 1 mM EDTA, and 0.5% NP-40 along with freshly-added phenylmethylsulfonyl fluoride (100 μg/mL) and protease inhibitor tablets (Roche;). Cellular debris was removed from samples after 1 h of lysis by centrifugation (10,000 rpm, 10 min, 4° C.). For western blots, 20-40 μg of total protein was subjected to 8% SDS-PAGE and subsequently transferred to nitrocellulose membranes. These membranes were then blocked for 1 h at room temperature (RT) in Odyssey blocking buffer (Li-COR Biosciences; Lincoln, Neb.), after which they were incubated with the appropriate primary antibody for 1 h at RT diluted in blocking buffer. After the 1 h incubation, membranes were washed three times in PBS containing 0.1% Tween (PBS-T). The membranes were then incubated with appropriate secondary antibodies (Li-COR Biosciences) for 1 h at RT after which membranes were washed three times in PBS-T, once in PBS and scanned using an Odyssey scanner (Li-COR Biosciences).

Protein extracts for immunoprecipitations were routinely recovered as described above 6-8 h post-infection in HeLa cells ($10^7$) infected with indicated strains at an MOI of 10. These extracts were then pre-cleared by incubation with protein G sepharose beads (GE Healthcare Life Sciences; Piscataway, N.J.) for 30 min at 4° C. with constant inversion. The samples were subsequently centrifuged (2,500 rpm, 1 min, 4° C.) and supernatants were transferred to fresh tubes and the extracts were incubated with the appropriate primary antibody overnight at 4° C. with constant inversion. Protein G beads were then added to the extracts and incubated for 2 h at 4° C. after which the beads were spun down (2,500 rpm, 1 min, 4° C.) and washed four times with lysis buffer. The resulting bead-protein complexes were resuspended in SDS-PAGE loading buffer, boiled for 15 min and loaded onto SDS gels. Western transfer and blotting was then performed as described above with the indicated antibodies.

Plaque morphology and replication analyses. Plaque morphology analysis was conducted on 60 mm-diameter dishes of confluent BSC-40 cells infected with ~100 plaque-forming units (PFU) of the indicated strain. After 48 h of infection, triplicate plates were stained with crystal violet and the plates were scanned using an HP ScanJet 6300C scanner. Resulting image files were subjected to plaque area analysis using ImageJ v1.04 g software (National Institutes of Health, USA). Unpaired student t-tests were performed on mean plaque areas between wild-type and each of the various RR mutant strains using GraphPad Prism (San Diego, Calif.) software (version 4.0). In some cases two different RR mutant strains were also compared for differences in mean plaque areas. A p-value of <0.05 was considered to be statistically significant. Growth analyses were conducted in BSC-40, HeLa, PANC-1 and Capan-2 cell cultures using the indicated MOIs and strains. Cells were harvested by scraping monolayers into the culture media at the indicated time points with three rounds of subsequent freeze-thawing to release virus. Virus stocks were titered on confluent monolayers of BSC-40 cells infected for 48 h and then stained with crystal violet. For PANC-1 and Capan-2 experiments, the mean virus yields of each virus from PANC-1 were divided by the mean yields obtained from Capan-2 cultures to obtain a ratio representing the fold-increase in replicative capacity of each strain in PANC-1 cells compared to Capan-2 cells. For viral genome replication analyses, at the indicated times, total DNA was extracted from BSC-40 cells infected with wild-type or ΔF4L viruses at an MOI of 2. In some cases cultures contained 0.5 mM HU in the media which was added 1 h post-infection. The extracted DNA was spotted onto Zetaprobe membrane using a vacuum-based slot-blot apparatus (BioRad) and the virus DNA was detected by hybridization to a $^{32}$P-labeled E9L gene probe. The $^{32}$P label was detected using a Typhoon 8600 phosphorimager and processed using ImageQuant (24).

Plaque-reduction assays. Plaque-reduction assays using cidofovir (CDV) were performed as previously described (1). Briefly, 60 mm-diameter dishes of confluent BSC-40 cells were inoculated with ~200 PFU of the indicated virus strains, and 1 h after infection either drug-free media or media containing the indicated doses of CDV was added to the cultures and the plates were incubated at 37° C. for 48 h. Plates were then stained with crystal violet to visualize and count plaques. Mean $EC_{50}$ values and their 95% confidence intervals (CI) were calculated using GraphPad Prism software. In cases where the 95% CIs of two different $EC_{50}$ values did not overlap, these two $EC_{50}$ values were considered to be statistically significant (p<0.05).

Confocal microscopy. HeLa cells were grown on coverslips in 24-well plates and infected with the indicated virus strains at a MOI of 5 for 10 h. The cells were fixed for 30 min on ice with 4% paraformaldehyde in PBS. The fixed cells were blocked and permeabilized for 1 h at RT in PBS containing 0.1% Tween (PBS-T) as well as 10% BSA. The coverslips were then incubated with the primary antibodies diluted in PBS-T (1% BSA) for 2 h at RT, washed three times and then incubated with secondary antibodies conjugated to Alexa 488 or 594 (Invitrogen) for 1 h at RT. The cells were then counterstained with 10 ng/mL 4',6'-diamidino-2-phenylindole (DAPI) in PBS-T for 15 min. The specimens were examined using a Zeiss 710 Laser-Scanning confocal microscope equipped with DAPI, Alexa 488, and Alexa 594 filters. Images were captured and processed using ZEN 2009 software and Adobe Photoshop (version 10.0.1).

Animal studies. Female NMRI mice, 3 to 4 weeks of age, were obtained from Charles River Laboratories (Brussels, Belgium). Mice were utilized at 5 mice per infection or control group for morbidity studies. Mice were anesthetized using ketamine-xylazine and inoculated intranasally (or mock-inoculated) with 4×10$^4$ PFU of virus diluted in 30 µL of saline. Animal body weights were recorded over the next 24 days or until the animals had to be euthanized because of more than 30% loss in body weight. To determine viral titers in lungs, two (wild-type infections) or five animals (ΔI4L, ΔF4L, and ΔI4L/ΔF4L infections) were euthanized on day 5. Lung samples were removed aseptically, weighed, homogenized in MEM, and frozen at −70° C. until assayed by titrations on HEL cells.

Plasmid construction and marker-rescue. BSC-40 cells were grown to confluence and then infected for 1 h with the appropriate VACV strain (see below) at a MOI of 2 in 0.5 mL of Phosphate-buffered saline (PBS). The cells were then transfected with 2 µg of appropriate plasmid DNA using Lipofectamine 2000 (Invitrogen). The cells were returned to the incubator for another 5 h, the transfection solution was replaced with 5 mL of fresh growth medium, and the cells were cultured for 24-48 h at 37° C. Virus progeny were released by freeze-thawing, and the virus titer was determined on BSC-40 cells. These resulting "marker-rescue" stocks were then re-plated in serial dilutions onto fresh BSC-40 monolayers. These virus cultures were then subjected to either visual selection of plaques (i.e. using X-gal or X-glu) or drug selection (i.e. using MPA). X-gal and X-glu were used at final concentration of 0.4 mg/mL in solid growth media overlays. Xanthine (250 µg/mL) and hypoxanthine (15 µg/mL) were used to supplement a working stock of MPA (25 µg/mL) for selections of yfp-gpt-encoding strains. The yfp-gpt-encoding strains encode a fusion protein between YFP (a derivative of GFP) and E. coli xanthine guanine phosphoribosyl-transferase (GPT) that allows for either visual (YFP) or mycohpenolic acid-based selection. All strains were plaque-purified in BSC-40 cells a minimum of three times and amplified in the absence of drug treatment to obtain final, working stocks. Confirmation of rescue of markers and subsequent deletion/disruption of endogenous VACV genomic sequence was confirmed by PCR analysis of total DNA extracted from infected BSC-40 cells. In some cases western-blotting was used to confirm the presence or absence of gene expression in the described VACV strains. Details of how each recombinant VACV strain are provided below.

ΔF4L virus construction. The plasmid pZIPPY-NEO/GUS (11) was used to clone an ~500 bp PCR product containing sequences flanking the "F5L" side of the F4L locus (primers: 5'-ACTAGTTAGATAAATGGAAATATCTT-3' [SEQ ID NO: 2] & 5'-AAGCTTTCAGTTATCTATATGCCTGT [SEQ ID NO: 3]) as well as an ~520 bp PCR product containing sequences flanking the "F3L" side of the F4L locus as well as the last 30 bp of the F4L ORF (primers: 5'-CCGCGGAAT-CATTTTTCTTTAGATGT-3' [SEQ ID NO: 4] & 5'-AG-ATCTTATGATGTCATCTTCCAGTT-3' [SEQ ID NO: 5]). The 500 bp PCR fragment was cloned into pZIPPY-NEO/GUS using SpeI and Hind III restriction sites and the 520 bp PCR fragment was cloned into the resulting vector using SacII and BglII restriction sites. These regions of homology were sequenced to ensure fidelity of PCR and cloning reactions. Rescue of this vector (now called pZIPPY-F5L$^H$-F3L$^H$) into WR leads to the deletion of nucleotides (nts) 33948-32987 in the WR genome (Genbank accession: NC_006998, herein incorporated by reference) comprising 31 nts in the intergenic region between F5L and F4L ORFs and the first 930 nts of the 960 bp F4L ORF. The last 30 bp of the F4L ORF were maintained in order to maintain the endogenous transcription termination signal for F5 expression contained at the 3' end of the F4L ORF (29). This region is replaced by a p7.5-promoted neomycin resistance (neo) gene as well as a gusA gene under the control of a modified H5 promoter (11). To generate the ΔF4L strain, pZIPPY-F5L$^H$+F3L$^H$ DNA (~2 µg) transfected into wild-type (strain WR) VACV-infected (MOI=2) BSC-40 cells. After 24 h of replication cells were harvested for virus, freeze-thawed three times and virus stocks were re-plated at multiple dilutions onto fresh BSC-40 cells overlaid with solid growth media. After 48-72 h of replication dishes were overlaid with a second layer of solid growth media containing 0.4 mg/mL X-glu. Blue plaques were isolated are re-plated in a similar manner such that ΔF4L virus had gone through four rounds of plaque-purification. Final isolates were amplified in BSC-40 cells and the absence of F4L coding sequence was confirmed by PCR (FIG. 1C). Absence of expression of F4 was also confirmed using western blotting with a mouse monoclonal antibody recognizing F4 (FIG. 1D).

ΔI4L & ΔI4L/ΔF4L virus construction. The plasmid pZIPPY-NEO/GUS (11) was used to clone an ~430 bp PCR product containing sequences flanking the "I5L" side of the I4L locus (primers: 5'-ACTAGTGGAAGGGTATCTATACT-TATAGAATAATC-3' [SEQ ID NO: 6] & 5'-GTC-GACTTTTGTTGGTGTAATAAAAAAATTATTTAAC-3'

[SEQ ID NO: 7]) as well as an ~340 bp PCR product containing sequences flanking the "I3L" side of the I4L locus (primers: 5'-CCGCGGGGTTAAACAAAAACATTTTTAT-TCTC-3' [SEQ ID NO: 8] & 5'-AGATCTGTT-TAGTCTCTCCTTCCAAC-3' [SEQ ID NO: 9]). The 430 bp PCR fragment was cloned into pZIPPY-NEO/GUS using SpeI and SalI restriction sites and the 340 bp PCR fragment was cloned into the resulting vector using SacII and BglII restriction sites. These regions of homology were also cloned into a separate vector, pDGIoxPKO using the same restriction sites as with cloning into pZIPPY-NEO/GUS. These regions of homology were sequenced to ensure fidelity of PCR and cloning reactions. Rescue of the first vector (now called pZIPPY-I5L$^H$+I3L$^H$) or the second (now called pDGIox-PKO-I5L$^H$+I3L$^H$) into WR leads to the deletion of nts 61929-64240 in the WR genome. The first vector (pZIPPY-I5L$^H$+I3L$^H$) replaces the deleted region with a p7.5-promoted neo gene as well as a gusA gene under the control of a modified H5 promoter (11). This vector was used to generate the ΔI4L strain. The second vector (pDGIoxPKO-I5L$^H$+I3L$^H$) replaces the deleted region with a yfp-gpt fusion gene promoted by a synthetic early/late pox promoter. This vector was used to generate the ΔI4LΔF4L strain by rescue of this vector into a ΔF4L background. Viruses were isolated after transfection of appropriate vectors and selection using either X-glu (for ΔI4L strain) or 25 µg/mL mycophenolic acid (for ΔI4LΔF4L strain) in BSC-40 cell culture. All isolates were plaque-purified a minimum of three times. Deletion of the I4L locus and loss of I4 expression was confirmed by PCR (FIG. 10) and western-blotting (FIG. 1D), respectively.

ΔI4L/ΔF4L/ΔJ2R, ΔF4L/ΔJ2R, ΔJ2R, ΔF4L/ΔJ2R$^{HisF4L}$, ΔF4L/ΔJ2R$^{HisY300FF4L}$, ΔI4L/ΔJ2R$^{FlagI4L}$, ΔJ2R$^{FlagHR1}$, & ΔJ2R$^{HisHp53R2}$ virus construction. The plasmid pSC66 (39), a derivative of the vaccinia transfer vector pSC65 (4) was used to generate inactivating mutations into the J2R (thymidine kinase; TK) locus as well as to introduce foreign genes into the J2R locus for expression under the control of a synthetic early/late poxvirus promoter (see below). This vector contains regions of homology flanking both left and right sides of the J2R ORF and creates a disruption in the J2R ORF such that an insertion is made in between nucleotides 81001 and 81002 in the WR genome. This ~4 kb insertion encodes a lacZ gene under the control of a p7.5 poxvirus promoter as well as introduces a second, early/late synthetic poxvirus promoter that initiates transcription in the opposite direction of the p7.5-lacZ cassette (4). A multiple cloning site downstream of the synthetic promoter allows for the insertion of foreign ORFs to be expressed (4). Transfection of pSC66 DNA into ΔI4L/ΔF4L, ΔF4L, or wild-type VACV-infected BSC-40 cells and subsequent selection of blue plaques (in the presence of X-gal in solid growth media) allowed for the creation of VACV strains ΔI4L/ΔF4L/ΔJ2R, ΔF4L/ΔJ2R, and ΔJ2R, respectively. Disruption of the J2R locus was confirmed by PCR analysis (FIG. 1C and data not shown). Primers 5'-AAGCTTATGCATCACCATCACCATCA-CATGGAACCCATCCTTGCACC-3' [SEQ ID NO: 10]& 5'-GCGGCCGCTTAAAAGTCAACATCTAAAG-3' [SEQ ID NO: 11] were used to PCR amplify and clone a His$_6$(His)-tagged F4L ORF into pCR2.1 (Invitrogen). A KpnI/NotI restriction fragment was then isolated from this plasmid and cloned into the KpnI/NotI restriction sites of pSC66 (generating pSC66$^{HisF4L}$) for expression under the synthetic early/late promoter. Rescue of pSC66$^{HisF4L}$ into the ΔF4L background generated strain ΔF4L/ΔJ2R$^{HisF4L}$. Site-directed mutagenesis using primers 5'-CGAAAAACGTGTGGGT-GAATTCCAAAAAATGGGAGTTATGTC-3' [SEQ ID NO: 12] & 5'-GACATAACTCCCATTTTTTGGAATTCAC-CCACACGTTTTTCG-3' [SEQ ID NO: 13] was performed with a QuickChange® II XL-kit (Stratagene) to generate a His$_6$-tagged F4L ORF encoding the Y300F substitution (creating pSC66$^{HisY300FF4L}$). Rescue of pSC66$^{HisY300FF4L}$ into the ΔF4L background generated strain ΔF4L/ΔJ2R$^{HisY300FF4L}$. Primers 5'-GTCGACATGGACTACAAG-GACGACGATGACAAG-3' [SEQ ID NO: 14] & 5'-GCG-GCCGCTTAACCACTGCATGATGTACAGATTTCGG-3' [SEQ ID NO: 15] were used to PCR amplify a Flag-tagged I4L ORF from a pCR2.1 vector containing a Flag-tagged I4L ORF insert previously generated using primers 5'-AAGCT-TATGGACTACAAGGACGACGATGACAAGATGTTTG-TCATTAAACGAAATG-3' [SEQ ID NO: 16] & 5'-GCGGC-CGCTTAACCACTGCATGATGTACAGATTTCGG-3' [SEQ ID NO: 17]. The resulting PCR fragment was sub-cloned into pCR2.1 and a SalI/NotI restriction fragment was cloned into the SalI/NotI sites of pSC66 (generating pSC66$^{FlagI4L}$). Rescue of pSC66$^{FlagI4L}$ into the ΔI4L background generated strain ΔI4L/ΔJ2R$^{FlagI4L}$. Primers 5'-GTC-GACATGGACTACAAGGACGACGATGACAAG-3' [SEQ ID NO: 18] & 5'-GCGGCCGCTCAGGATCCACACATCA-GACATTC-3' [SEQ ID NO: 19] were used to PCR amplify a Flag-tagged HR1 ORF from a pCR2.1 vector containing a Flag-tagged HR1ORF insert previously generated using primers 5'-CCAGTGTGGTGGATGGACTACAAGGAC-GACGATGACAAGATGCATGTGA TCAAGCGAGATG-3' [SEQ ID NO: 20] & 5'-GCGGCCGCTCAGGATCCACA-CATCAGACATTC-3' [SEQ ID NO: 21] and HR1 cDNA (Invitrogen). The resulting PCR fragment was sub-cloned into pCR2.1 and a SalI/NotI restriction fragment was cloned into the SalI/NotI sites of pSC66 (generating pSC66$^{FlagHR1}$). Rescue of pSC66$^{FlagHR1}$ into the wild-type background generated strain ΔJ2R$^{FlagHR1}$. Primers 5'-GGATCCATGCAT-CACCATCACCATCACATGGGGGACCCGGAAAGG-CCG-3' [SEQ ID NO: 22] & 5'-GCGGCCGCT-TAAAAATCTGCATCCAAGG-3' [SEQ ID NO: 23] were used to PCR amplify a His$_6$-tagged Hp53R2 ORF from Hp53R2 cDNA (Genecopeia Inc.; Germantown, Md.). The resulting PCR fragment was sub-cloned into pCR2.1 and a KpnI/NotI restriction fragment was cloned into the KpnI/NotI restriction sites of pSC66 (generating pSC66$^{HisHp53R2}$) Rescue of pSC66$^{HisHp53R2}$ into the wild-type background generated strain ΔJ2R$^{HisHp53R2}$.

TABLE 1

Major VACV strains used in this study.

| Strain[1] | I4L locus[2] | F4L locus[2] | J2R locus[2] |
|---|---|---|---|
| Wild-type (WR) | + | + | + |
| ΔI4L | −(neo; gusA) | + | + |
| ΔF4L | + | −(neo; gusA) | + |
| ΔJ2R | + | + | −(lacZ) |
| ΔI4L/ΔF4L | −(yfp-gpt) | −(neo; gusA) | + |

TABLE 1-continued

Major VACV strains used in this study.

| Strain[1] | I4L locus[2] | F4L locus[2] | J2R locus[2] |
|---|---|---|---|
| ΔI4L/ΔF4L/ΔJ2R | −(yfp-gpt) | −(neo; gusA) | −(lacZ) |
| ΔF4L/ΔJ2R | + | −(neo; gusA) | −(lacZ) |
| ΔF4L/ΔJ2R$^{HisF4L}$ | + | −(neo; gusA) | −(lacZ; HisF4L) |
| ΔF4L/ΔJ2R$^{HisY300FF4L}$ | + | −(neo; gusA) | −(lacZ; HisY300FF4L) |
| ΔI4L/ΔF4L/ΔJ2R$^{HisF4L}$ | −(yfp-gpt) | −(neo; gusA) | −(lacZ; HisF4L) |
| ΔI4L/ΔF4L/ΔJ2R$^{HisY300FF4L}$ | −(yfp-gpt) | −(neo; gusA) | −(lacZ; HisY300FF4L) |
| ΔF4L/ΔJ2R$^{HisF4LΔR1BD}$ | + | −(neo; gusA) | −(lacZ; HisF4LΔR1BD) |
| ΔF4L/ΔJ2R$^{HisY300FF4LΔR1BD}$ | + | −(neo; gusA) | −(lacZ; HisY300FF4LΔR1BD) |
| ΔF4L/ΔJ2R$^{HisECTVR2}$ | + | −(neo; gusA) | −(lacZ; HisECTVR2) |
| ΔF4L/ΔJ2R$^{HisMYXR2}$ | + | −(neo; gusA) | −(lacZ; HisMYXR2) |
| ΔF4L/ΔJ2R$^{HisSFVR2}$ | + | −(neo; gusA) | −(lacZ; HisSFVR2) |
| ΔI4L/ΔJ2R$^{FlagI4L}$ | −(neo; gusA) | + | −(lacZ; HisSFVR2) |
| ΔJ2R$^{FlagHR1}$ | + | + | −(lacZ; FlagHR1) |
| ΔJ2R$^{HisHp53R2}$ | + | + | −(lacZ; HisHp53R2) |
| ΔF4L/ΔJ2R$^{HisHp53R2}$ | + | −(neo; gusA) | −(lacZ; HisHp53R2) |

[1]All strains were generated in the Western Reserve (WR) strain of VACV.
[2]"+" indicates locus is intact and "−" indicates locus is disrupted. Marker genes and inserted viral or human genes present at disrupted loci are in parentheses. Abbreviations: His, His$_6$ epitope tag; Flag, Flag epitope tag; R1BD, R1-binding domain; VACV, vaccinia virus; ECTV, ectromelia virus; MYX, myxoma virus; SFV, Shope fibroma virus; HR1, human R1; Hp53R2, human p53R2. See Materials and Methods for further details.

TABLE 2

Susceptibility of VACV RR mutant strains to cidofovir (CDV), hydroxyurea (HU) and phosphonoacetic acid (PAA).

| | Mean EC$_{50}$ of Compound | | | | | |
|---|---|---|---|---|---|---|
| Virus | CDV (μM)[1] | Fold Change[2] | HU (mM)[1] | Fold Change[2] | PAA (μg/mL)[1] | Fold Change[2] |
| Wild-type | 42.0 (36.2-48.7) | 1.0 | 0.87 (0.72-1.06) | 1.0 | 50.5 (41.9-61.0) | 1.0 |
| ΔI4L | 25.1 (22.0-28.7) | 1.7 | 0.19 (0.15-0.24) | 4.6 | 55.6 (44.9-68.9) | 1.1 |
| ΔF4L | 6.2 (5.5-7.0) | 6.8 | 0.05 (0.04-0.06) | 17.4 | 56.6 (49.4-64.9) | 1.1 |
| ΔI4L/ΔF4L | 6.8 (5.4-8.5) | 6.2 | 0.05 (0.04-0.06) | 17.4 | 54.7 (48.3-62.1) | 1.1 |
| ΔI4L/ΔF4L/ΔJ2R | 7.6 (6.7-8.5) | 5.5 | 0.05 (0.05-0.06) | 17.4 | 47.4 (39.7-56.6) | 1.1 |
| ΔF4L/ΔJ2R | 8.1 (6.6-9.9) | 5.2 | 0.07 (0.06-0.08) | 12.4 | 49.0 (40.9-58.6) | 1.0 |
| ΔF4L/ΔJ2R$^{HisF4L}$ | 41.2 (35.9-47.1) | 1.0 | 0.68 (0.50-0.91) | 1.3 | 46.8 (38.3-57.1) | 1.1 |
| ΔF4L/ΔJ2R$^{HisY300FF4L}$ | 3.5 (3.0-4.2) | 12 | 0.03 (0.03-0.03) | 29 | 44.9 (39.0-51.8) | 1.1 |

[1]Values in parentheses represent 95% confidence intervals.
[2]Compared to mean EC$_{50}$ of wild-type virus. Bold values indicate statistically significant (P < 0.05) differences from wild-type values.

TABLE 3

Differential conservation of Chordopoxirinae RR genes.

| Genus | R1 | R2 | TK | Example Species[3] |
|---|---|---|---|---|
| Orthopoxvirus | +[1] | + | + | VACV |
| | | | | HSPV |
| | | | | TATV |
| | | | | VARV |
| Suipoxvirus | + | + | + | SPXV |
| Yatapoxvirus | − | + | + | TANV |
| | | | | YLDV |
| Leporipoxvirus | − | + | + | MYXV |
| | | | | SFV |
| Capripoxvirus | − | + | + | GTPV |
| | | | | SPPV |
| | | | | LSDV |
| Cervidpoxvirus | − | + | + | DPV |
| Avipoxvirus | − | +[2] | + | FPV |
| | | | | CNPV |
| Molluscipoxvirus | − | − | − | MCV |
| Parapoxvirus | − | − | − | ORFV |
| Unclassified | − | − | − | CRV |

[1]SPV contains a fragmented R1 gene.
[2]FPV contains a fragmented R2 gene.

"+" Indicates presence and "−" indicates absence of indicated ribonucleotide reductase (RR) or thymidine kinase (TK) genes in viral genomes.
[3]Example species of indicated genera are given.

Abbreviations: VACV, vaccinia virus; HSPV, horsepox virus; TATV, taterapox virus; VARV, variola virus; SPXV, swinepox virus; tanapox virus; yaba-like disease virus; MYXV, myxoma virus; SFV, Shope fibroma virus; GTPV, goatpox virus; SPPV, sheeppox virus; LSDV, lumpy skin disease virus; DPV, deerpox virus; FPV, fowlpox virus; CNPV, canarypox virus; MCV, molluscum contagiosum; ORFV, orf virus; CRV, crocodilepox virus.

TABLE 4

List of cancer types that over-express RR proteins.

| Cancer Type | Over-expressed Subunit | Cell Line (or Clinical Isolate) | Reference |
|---|---|---|---|
| Breast Cancer | RR2 | MCF7, T47D, MDA-231 | (44) |
| Hepatocellular carcinoma | RR1, RR2 | Clinical Isolate | (36) |
| Pancreatic cancer | RR2 | PANC-1, CAPAN-2 | (9, 10) |
| Melanoma | RR2 | Clinical Isolate | (22) |
| Esophageal and gastric | RR2 | Clinical Isolate | (22) |

TABLE 5

List of sequences.

| SEQ ID NO: | Gene | Sequence |
|---|---|---|
| 1 | Ribonucleotide reductase small subunit (Vaccinia virus WR) Genbank accession number AAO89322 | MEPILAPNPNRFVIFPIQYYDIWNMYKKAEASFWTVEKV DISKDINDWNKLTPDEKYFIKHVLAFFAASD GIVNENLAERFCTEVQITEARCFYGFQMAIENIHSEMYS LLIDTYVKDSNEKNYLFNAIETMPCVKKKAD WAQKWIHIDSAGYGERLIAFAAVEGIFFSGSFASIFWLKK RGLMPGLTFSNELISRDEGLHCDFACLMFKH LLHPPSEETVRSIITDAVSIEQEFLTAALPVKLIGMNCE MMKTYIEFVADRLISELGFKKIYNVTNPFDF MENISLEGKTNFFEKRVGEYQKMGVMSQEDNHFSLDVDF |
| 2 | Forward primer for sequences flanking the "F5L" side of the F4L locus | 5'-ACTAGTTAGATAAATGGAAATATCTT-3' |
| 3 | Reverse primer for sequences flanking the "F5L" side of the F4L locus | 5'-AAGCTTTCAGTTATCTATATGCCTGT-3' |
| 4 | Forward primer for sequences flanking the "F3L" side of the F4L locus as well as the last 30 bp of the F4L ORF | 5'-CCGCGGAATCATTTTTCTTTAGATGT-3' |
| 5 | Reverse primer for sequences flanking the "F3L" side of the F4L locus as well as the last 30 bp of the F4L ORF | 5'-AGATCTTATGATGTCATCTTCCAGTT-3' |
| 6 | Forward primer for sequences flanking the "I5L" side of the I4L locus | 5'-ACTAGTGGAAGGGTATCTATACTTATAGAA TAATC-3' |
| 7 | Reverse primer for sequences flanking the "I5L" side of the I4L locus | 5'-GTCGACTTTTGTTGGTOTAATAAAAAAATTA TTTAAC-3' |
| 8 | Forward primer for sequences flanking the "I3L" side of the I4L locus | 5'-CCGCGGGGTTAAACAAAAACATTTTTATTCTC-3' |
| 9 | Reverse primer for sequences flanking the "I3L" side of the I4L locus | 5'-AGATCTGTTTAGTCTCTCCTTCCAAC-3' |
| 10 | Forward primer for His$_6$-tagged F4L ORF | 5'-AAGCTTATGCATCACCATCACCATCACATO GAACCCATCCTTGCACC-3' |
| 11 | Reverse primer for His$_6$-tagged F4L ORF | 5'-GCGGCCGCTTAAAAGTCAACATCTAAAG-3' |
| 12 | Forward primer for generating His$_6$-tagged F4L ORF encoding the Y300F substitution | 5'-CGAAAAACGTGTGGGTGAATTCCAAAAAAT GGGAGTTATGTC-3' |
| 13 | Reverse primer for generating His,-tagged F4L | 5'-GACATAACTCCCATTTTTTGGAATTCACCC ACACGTTTTTCG-3' |

TABLE 5-continued

| List of sequences. | | |
|---|---|---|
| SEQ ID NO: | Gene | Sequence |
| | ORF encoding the Y300F substitution | |
| 14 | Forward primer for PCR amplification of a Flag-tagged I4L ORF from a pCR2.1 vector containing a Flag-tagged I4L ORF insert | 5'-GTCGACATOGACTACAAGGACOACGATO ACAAG-3' |
| 15 | Reverse primer for PCR amplification of a Flag-tagged I4L ORF from a pCR2.1 vector containing a Flag-tagged I4L ORF insert | 5'-GCGGCCGCTTAACCACTGCATGATGTACA GATTTCGG-3' |
| 16 | Forward primer for generating a Flag-tagged I4L ORF insert for pCR2.1 vector | 5'-AAGCTTATGGACTACAAGGACGACGA TGACAAGATGTTTGTCATTAAACGAAATG-3' |
| 17 | Reverse primer for generating a Flag-tagged I4L ORF insert for pCR2.1 vector | 5'-GCGGCCGCTTAACCACTGCATGATGTA CAGATTTCGG-3' |
| 18 | Forward primer for PCR amplification of a Flag-tagged HR1 ORF from a pCR2.1 vector containing a Flag-tagged HR1 ORF insert | 5'-GTCGACATGGACTACAAGGACGACGAT GACAAG-3' |
| 19 | Reverse primer for PCR amplification of a Flag-tagged HR1 ORF from a pCR2.1 vector containing a Flag-tagged HR1 ORF insert | 5'-GCGGCCGCTCAGGATCCACACATCAGA CATTC-3' |
| 20 | Forward primer for generating a Flag-tagged HR1 ORF insert for pCR2.1 vector | 5'-CCAGTGTGGTGGATGGACTACAAGGACG ACGATGACAAGATGCATGTGATCAAGCGAGATG-3' |
| 21 | Reverse primer for generating a Flag-tagged HR1 ORF insert for pCR2.1 vector | 5'-GCGGCCGCTCAGGATCCACACATCAGA CATTC-3' |
| 22 | Forward primer for $His_6$-tagged Hp53R2 ORF from Hp53R2 cDNA | 5'-GGATCCATGCATCACCATCACCATCACATGG GGGACCCGGAAAGGCCG-3' |
| 23 | Reverse primer for $His_6$-tagged Hp53R2 ORF from Hp53R2 cDNA | 5'-GCGGCCGCTTAAAAATCTGCATCCAAGG-3' |

Example 2

Mouse monoclonal anti-VACV F4 antibody. Mouse monoclonal antibodies were generated by using full-length ectromelia virus R2 protein with a C-terminal $His_6$ tag as the antigen.

To produce monoclonal antibodies, antibody producing cells (lymphocytes) can be harvested from an immunized animal and fused with myeloma cells by standard somatic cell fusion procedures thus immortalizing these cells and yielding hybridoma cells. Such techniques are well known in the art, (e.g. the hybridoma technique originally developed by Kohler and Milstein (Nature 256:495-497 (1975)) as well as other techniques such as the human B-cell hybridoma technique (Kozbor et al., Immunol. Today 4:72 (1983)), the EBV-hybridoma technique to produce human monoclonal antibodies (Cole et al., Methods Enzymol, 121:140-67 (1986)), and screening of combinatorial antibody libraries (Huse et al., Science 246:1275 (1989)). Hybridoma cells can be screened immunochemically for production of antibodies specifically reactive with the peptide and the monoclonal antibodies can be isolated. Since ectromelia R2 protein is >98% identical to VACV F4 protein, the resulting antibody also recognizes VACV F4. This antibody is suitable for western blotting, immunoprecipitation and immunofluorescence.

Example 3

In vitro studies. In vitro (i.e. in cell culture) replication of RR mutant strains is being assessed in various human cancer cell lines that are used as models for the study of a variety of tumor types including, but not limited to, gliomas (eg. U118 and U87 cell lines), breast cancers (eg. MCF7 and T47D cell lines), and heptaocellular carcionmas (eg. Hep3B). Many of these cell lines are known to over-express cellular RR components (see Table 4) and the expression levels of cellular RR components are being assessed by Western-blotting and compared to non-transformed cell lines of a similar tissue type when possible.

Example 4

In vivo human tumor model studies. To correlate observations made from in vitro studies, human tumor models are being established in nude mice. PANC-1 (18, 26) and MDA-231 (32) cell lines have previously been used to establish human tumors in nude mice and these studies assess the ability of various RR mutant strains to infect and destroy tumor tissue in these animals. The selectivity of these mutant strains for tumor tissue over normal mouse tissue is also being assessed.

Example 5

Derivation of RR deletions/mutations in other vaccinia strains. The mutant RR strains described in this disclosure thus far have been generated in the WR strain of vaccinia. This strain is neurovirulent and highly pathogenic in mice and would likely be an unsuitable background for the development of mutant RR strains for use in human oncolytic virotherapy. Therefore, the various I4L, F4L and J2R deletions/mutations are being developed in the genome of the Chinese vaccination strain of vaccinia, Tian Tian [(19); Genbank accession: AF095689, herein incorporated by reference] which is likely to be a more suitable background for clinical treatments. The Tian Tian strain is attenuated in virulence compared to strain WR and was routinely used to vaccinate individuals in China before the cessation of smallpox vaccination in 1980 (15). Therefore, it is predicted that the Tian Tian strain will be a more suitable background in terms of clinical safety for the development of the aforementioned strains for oncolytic virotherapy in humans.

Example 6

Susceptibility of human cancer types to RR mutant oncolytic poxviruses and use in oncolytic viral therapy. The ΔF4L and/or Y300F F4-expressing strains are used as a component of combined therapy, where patients are first treated with HU (or gemcitabine), followed by treatment with one of these oncolytic VACV strains to target remaining drug-resistant tumor tissue. First, breast tumor tissue, for example, from a patient biopsy is pre-screened to determine if the tumor tissue will respond well to oncolytic treatment using the ΔF4L and/or Y300F F4-expressing vaccinia strains. Cellular RR expression in the breast tumor tissue sample is then detected and compared to the cellular RR expression levels in normal breast tissue using rapid RT-PCR and automated quantitative analysis. Alternatively, cellular RR expression in tissue samples can be determined by detecting RR protein levels using, for example, western blots, and/or detecting RR subunit transcripts using for example RT-PCR. If the cellular RR expression of the tumor tissue sample is found to be elevated compared to the normal tissue, the patient is a good candidate for the combined therapy described above that includes oncolytic virotherapy using the ΔF4L and/or Y300F F4-expressing vaccinia strains.

A person skilled in the art will understand that this combined therapy is effective on a broad range of human cancer types, including, cancers with increased RR cellular levels expression.

REFERENCES

1. Andrei, G., D. B. Gammon, P. Fiten, E. De Clercq, G. Opdenakker, R. Snoeck, and D. H. Evans. 2006. Cidofovir resistance in vaccinia virus is linked to diminished virulence in mice. J Virol 80:9391-401.
2. Angelova, A. L., M. Aprahamian, S. P. Grekova, A. Hajri, B. Leuchs, N. A. Giese, C. Dinsart, A. Herrmann, G. Balboni, J. Rommelaere, and Z. Raykov. 2009. Improvement of gemcitabine-based therapy of pancreatic carcinoma by means of oncolytic parvovirus H-1PV. Clin Cancer Res 15:511-9.
3. Chabes, A. L., C. M. Pfleger, M. W. Kirschner, and L. Thelander. 2003. Mouse ribonucleotide reductase R2 protein: a new target for anaphase-promoting complex-Cdh1-mediated proteolysis. Proc Natl Acad Sci USA 100:3925-9.
4. Chakrabarti, S., J. R. Sisler, and B. Moss. 1997. Compact, synthetic, vaccinia virus early/late promoter for protein expression. Biotechniques 23:1094-7.
5. Chen, Y., D. Donald, K. Savin, P. J. Presidente, and D. Hartman. 2005. *Haemonchus contortus*: molecular cloning, sequencing, and expression analysis of the gene coding for the small subunit of ribonucleotide reductase. Exp Parasitol 111:250-4.
6. Child, S. J., G. J. Palumbo, R. M. Buller, and D. E. Hruby. 1990. Insertional inactivation of the large subunit of ribonucleotide reductase encoded by vaccinia virus is associated with reduced virulence in vivo. Virology 174:625-9.
7 Chimploy, K., and C. K. Mathews. 2001. Mouse ribonucleotide reductase control: influence of substrate binding upon interactions with allosteric effectors. J Biol Chem 276:7093-100.
8. Cihlar, T., and M. S. Chen. 1996. Identification of enzymes catalyzing two-step phosphorylation of cidofovir and the effect of cytomegalovirus infection on their activities in host cells. Mol Pharmacol 50:1502-10.
9. Duxbury, M. S., H. Ito, E. Benoit, M. J. Zinner, S. W. Ashley, and E. E. Whang. 2004. Retrovirally mediated RNA interference targeting the M2 subunit of ribonucleotide reductase: A novel therapeutic strategy in pancreatic cancer. Surgery 136:261-9.
10. Duxbury, M. S., H. Ito, M. J. Zinner, S. W. Ashley, and E. E. Whang. 2004. RNA interference targeting the M2 subunit of ribonucleotide reductase enhances pancreatic adenocarcinoma chemosensitivity to gemcitabine. Oncogene 23:1539-48.
11. Dvoracek, B., and T. Shors. 2003. Construction of a novel set of transfer vectors to study vaccinia virus replication and foreign gene expression. Plasmid 49:9-17.
12. Engstrom, Y., S. Eriksson, I. Jildevik, S. Skog, L. Thelander, and B. Tribukait. 1985. Cell cycle-dependent expression of mammalian ribonucleotide reductase. Differential regulation of the two subunits. J Biol Chem 260:9114-6.
13. Engstrom, Y., and B. Rozell. 1988. Immunocytochemical evidence for the cytoplasmic localization and differential expression during the cell cycle of the M1 and M2 subunits of mammalian ribonucleotide reductase. EMBO J. 7:1615-20.

14. Engstrom, Y., B. Rozell, H. A. Hansson, S. Stemme, and L. Thelander. 1984. Localization of ribonucleotide reductase in mammalian cells. EMBO J. 3:863-7.
15. Fang, Q., L. Yang, W. Zhu, L. Liu, H. Wang, W. Yu, G. Xiao, P. Tien, L. Zhang, and Z. Chen. 2005. Host range, growth property, and virulence of the smallpox vaccine: vaccinia virus Tian Tian strain. Virology 335:242-51.
16. Honig, H., D. S. Lee, W. Conkright, J. Divito, H. Hasson, M. LaMare, A. Rivera, D. Park, J. Tine, K. Guito, K. W. Tsang, J. Schlom, and H. L. Kaufman. 2000. Phase I clinical trial of a recombinant canarypoxvirus (ALVAC) vaccine expressing human carcinoembryonic antigen and the B7.1 co-stimulatory molecule. Cancer Immunol Immunother 49:504-14.
17. Hu, Y., J. Lee, J. A. McCart, H. Xu, B. Moss, H. R. Alexander, and D. L. Bartlett. 2001. Yaba-like disease virus: an alternative replicating poxvirus vector for cancer gene therapy. J Virol 75:10300-8.
18. Iwaki, K., K. Shibata, M. Ohta, Y. Endo, H. Uchida, M. Tominaga, R. Okunaga, S. Kai, and S. Kitano O. 2008. A small interfering RNA targeting proteinase-activated receptor-2 is effective in suppression of tumor growth in a Panc1 xenograft model. Int J Cancer 122:658-63.
19. Jin, Q., Chen, N. H., Chen, S. X., Huang, J., Feng, Z. H., Yuan, J. S., Jin, D. Y., Bai, H. D., Hou, Y. D. 1997. Characterization of the complete genomic sequence of the vaccinia virus Tian Tian strain. Sci. China 27:562-567.
20. Kaufman, H. L., H. J. Lenz, J. Marshall, D. Singh, C. Garett, C. Cripps, M. Moore, M. von Mehren, R. Dalfen, W. J. Heim, R. M. Conry, W. J. Urba, A. B. Benson, 3rd, M. Yu, J. Caterini, S. Kim-Schulze, M. Debenedette, D. Salha, T. Vogel, I. Elias, and N. L. Berinstein. 2008. Combination chemotherapy and ALVAC-CEA/B7.1 vaccine in patients with metastatic colorectal cancer. Clin Cancer Res 14:4843-9.
21. Kern, E. R., M. N. Prichard, D. C. Quenelle, K. A. Keith, K. N. Tiwari, J. A. Maddry, and J. A. Secrist, 3rd. 2009. Activities of certain 5-substituted 4'-thiopyrimidine nucleosides against orthopoxvirus infections. Antimicrob Agents Chemother 53:572-9.
22. Kolesar, J., W. Huang, J. Eickhoff, K. Hahn, D. Alberti, S. Attia, W. Schelman, K. Holen, A. Traynor, P. Ivy, and G. Wilding. 2009. Evaluation of mRNA by Q-RTPCR and protein expression by AQUA of the M2 subunit of ribonucleotide reductase (RRM2) in human tumors. Cancer Chemother Pharmacol 64:79-86.
23. Lee, M. S., J. M. Roos, L. C. McGuigan, K. A. Smith, N. Cormier, L. K. Cohen, B. E. Roberts, and L. G. Payne. 1992. Molecular attenuation of vaccinia virus: mutant generation and animal characterization. J Virol 66:2617-30.
24. Lin, Y. C., J. Li, C. R. Irwin, H. Jenkins, L. DeLange, and D. H. Evans. 2008. Vaccinia virus DNA ligase recruits cellular topoisomerase II to sites of viral replication and assembly. J Virol 82:5922-32.
25. Manual, B. C. A. C. D. 2006. Hydroxyurea Information Sheet, (http://www.bccancer.bc.ca/NR/rdonlyres/D83AB234-30D8-4489-B4DE-41FAA5B81743/19225/Hydroxyureamonograph_1Dec06.pdf).
26. McLeod, E. J., A. D. Beischer, J. S. Hill, and A. H. Kaye. 1997. Multicellular tumor spheroids grown from pancreatic carcinoma cell lines: use as an orthotopic xenograft in athymic nude mice. Pancreas 14:237-48.
27. Pontarin, G., A. Fijolek, P. Pizzo, P. Ferraro, C. Rampazzo, T. Pozzan, L. Thelander, P. A. Reichard, and V. Bianchi. 2008. Ribonucleotide reduction is a cytosolic process in mammalian cells independently of DNA damage. Proc Natl Acad Sci USA 105:17801-6.
28. Rosell, R., E. Felip, M. Taron, J. Majo, P. Mendez, M. Sanchez-Ronco, C. Queralt, J. J. Sanchez, and J. Maestre. 2004. Gene expression as a predictive marker of outcome in stage IIB-IIIA-IIIB non-small cell lung cancer after induction gemcitabine-based chemotherapy followed by resectional surgery. Clin Cancer Res 10:4215s-4219s.
29. Roseman, N. A., and M. B. Slabaugh. 1990. The vaccinia virus HindIII F fragment: nucleotide sequence of the left 6.2 kb. Virology 178:410-8.
30. Rova, U., A. Adrait, S. Potsch, A. Graslund, and L. Thelander. 1999. Evidence by mutagenesis that Tyr(370) of the mouse ribonucleotide reductase R2 protein is the connecting link in the intersubunit radical transfer pathway. J Biol Chem 274:23746-51.
31. Saban, N., and M. Bujak. 2009. Hydroxyurea and hydroxamic acid derivatives as antitumor drugs. Cancer Chemother Pharmacol 64:213-21.
32. Seymour, L. W., M. Bazan-Peregrino, R. Carlisle, R. Hernandez-Alcoceba, R. Iggo, K. Homicsko, G. Hallden, V. Mautner, J. Shen, and K. Fisher. 2008. Comparison of Molecular Strategies for Breast Cancer Virotherapy using Oncolytic Adenovirus. Hum Gene Ther.
33. Slabaugh, M. B., and C. K. Mathews. 1986. Hydroxyurea-resistant vaccinia virus: overproduction of ribonucleotide reductase. J Virol 60:506-14.
34. Souglakos, J., I. Boukovinas, M. Taron, P. Mendez, D. Mavroudis, M. Tripaki, D. Hatzidaki, A. Koutsopoulos, E. Stathopoulos, V. Georgoulias, and R. Rosell. 2008. Ribonucleotide reductase subunits M1 and M2 mRNA expression levels and clinical outcome of lung adenocarcinoma patients treated with docetaxel/gemcitabine. Br J Cancer 98:1710-5.
35. Stanford, M. M., and G. McFadden. 2007. Myxoma virus and oncolytic virotherapy: a new biologic weapon in the war against cancer. Expert Opin Biol Ther 7:1415-25.
36. Sunaga, M., T. Tomonaga, M. Yoshikawa, M. Ebara, H. Shimada, H. Saisho, and F. Nomura. 2007. Gene expression of 5-fluorouracil metabolic enzymes in hepatocellular carcinoma and non-tumor tissue. Chemother 19:709-15.
37. Tulman, E. R., G. Delhon, C. L. Afonso, Z. Lu, L. Zsak, N. T. Sandybaev, U. Z. Kerembekova, V. L. Zaitsev, G. F. Kutish, and D. L. Rock. 2006. Genome of horsepoxvirus. J Virol 80:9244-58.
38. Wang, X., A. Zhenchuk, K. G. Wiman, and F. Albertioni. 2009. Regulation of p53R2 and its role as potential target for cancer therapy. Cancer Lett 276:1-7.
39. Wasilenko, S. T., T. L. Stewart, A. F. Meyers, and M. Barry. 2003. Vaccinia virus encodes a previously uncharacterized mitochondrial-associated inhibitor of apoptosis. Proc Natl Acad Sci USA 100:14345-50.
40. Watanabe, I., H. Kasuya, N. Nomura, T. Shikano, T. Shirota, N. Kanazumi, S. Takeda, S, Nomoto, H. Sugimoto, and A. Nakao. 2008. Effects of tumor selective replication-competent herpes viruses in combination with gemcitabine on pancreatic cancer. Cancer Chemother Pharmacol 61:875-82.
41. Woo, Y., K. J. Kelly, M. M. Stanford, C. Galanis, Y. S. Chun, Y. Fong, and G. McFadden. 2008. Myxoma virus is oncolytic for human pancreatic adenocarcinoma cells. Ann Surg Oncol 15:2329-35.
42. Wright, J. A., T. G. Alam, G. A. McClarty, A. Y. Tagger, and L. Thelander. 1987. Altered expression of ribonucleotide reductase and role of M2 gene amplification in hydroxyurea-resistant hamster, mouse, rat, and human cell lines. Somat Cell Mol Genet. 13:155-65.

43. Xue, L., B. Zhou, X. Liu, T. Wang, J. Shih, C. Qi, Y. Heung, and Y. Yen. 2006. Structurally dependent redox property of ribonucleotide reductase subunit p53R2. Cancer Res 66:1900-5.
44. Yun, H. J., Y. H. Cho, Y. Moon, Y. W. Park, H. K. Yoon, Y. J. Kim, S. H. Cho, Y. I. Lee, B. S. Kang, W. J. Kim, K. Park, and W. Seo. 2008. Transcriptional targeting of gene expression in breast cancer by the promoters of protein regulator of cytokinesis 1 and ribonuclease reductase 2. Exp Mol Med 40:345-53.
45. Xiong X, Smith J L, Kim C, Huang E S, Chen M S (1996) Kinetic analysis of the interaction of cidofovir diphosphate with human cytomegalovirus DNA polymerase. Biochem Pharmacol 51: 1563-1567.
46. Magee W C, Hostetler K Y, Evans D H (2005) Mechanism of inhibition of vaccinia virus DNA polymerase by cidofovir diphosphate. Antimicrob Agents Chemother 49: 3153-3162.,
47. Magee W C, Aldern K A, Hostetler K Y, Evans D H (2008) Cidofovir and (S)-9-[3-hydroxy-(2-phosphonomethoxy) propyl]adenine are highly effective inhibitors of vaccinia virus DNA polymerase when incorporated into the template strand. Antimicrob Agents Chemother 52: 586-597.
48. Prichard M N, Keith K A, Johnson M P, Harden E A, McBrayer A, et al. (2007) Selective phosphorylation of antiviral drugs by vaccinia virus thymidine kinase. Antimicrob Agents Chemother 51: 1795-1803.
49. Taddie J A, Traktman P (1993) Genetic characterization of the vaccinia virus DNA polymerase: cytosine arabinoside resistance requires a variable lesion conferring phosphonoacetate resistance in conjunction with an invariant mutation localized to the 3'-5' exonuclease domain. J Virol 67: 4323-4336.
50. Cresawn S G, Prins C, Latner D R, Condit R C (2007) Mapping and phenotypic analysis of spontaneous isatin-beta-thiosemicarbazone resistant mutants of vaccinia virus. Virology 363: 319-332.

The invention claimed is:

1. A method for inducing cell death in a neoplastic disorder cell, the method comprising:
   contacting said cell with an effective amount of a vaccinia virus comprising a gene encoding a modified R2 protein comprising an amino acid sequence at least 90% identical to the amino acid sequence of SEQ ID NO: 1, wherein vaccinia virus does not express a wild type R2 protein; and
   wherein the modified R2 protein expressed by the vaccinia virus comprises a substitution of a tyrosine residue, wherein the substituted tyrosine residue corresponds to position 300 of SEQ ID NO: 1, or
   wherein the modified R2 protein expressed by the vaccinia virus comprises a deletion of 7 amino acids of R1 binding domain (R1BD); and
   wherein said contacting is effective to induce cell death in the neoplastic disorder cell,
   wherein the neoplastic disorder cell expresses ribonucleotide reductase.

2. The method of claim 1, wherein the neoplastic disorder cell is cancer cell selected from breast cancer cell, colorectal cancer cell, hepatic cancer cell, pancreatic cancer cell, skin cancer cell, lung cancer cell, esophageal cancer cell, leukemia cell, ovarian cancer cell, head and neck cancer cell, glioma cell, and gastric cancer cell.

3. The method of claim 1, wherein the modified R2 protein expressed by the vaccinia virus comprises a substitution of a tyrosine residue, wherein the substituted tyrosine residue corresponds to position 300 of SEQ ID NO: 1.

4. The method of claim 3, wherein the modified R2 protein comprises an amino acid sequence at least 95% identical to the amino acid sequence of SEQ ID NO: 1.

5. The method of claim 3, wherein the tyrosine residue is substituted with phenylalanine.

6. The method of claim 1, wherein the modified R2 protein comprises the deletion of 7 amino acids of the R1BD.

7. The method of claim 6, wherein the modified R2 protein comprises an amino acid sequence at least 95% identical to the amino acid sequence of SEQ ID NO: 1.

8. The method of claim 1, wherein the vaccinia virus further comprises a functionally inactivated thymidine kinase gene.

9. The method of claim 1, wherein the vaccinia virus further comprises a functionally inactivated R1 gene.

10. The method of claim 1, wherein the vaccinia virus further comprises a functionally inactivated vaccinia virus growth factor gene or a functionally inactivated nucleotide metabolism-related gene.

11. A method for treating a neoplastic disorder in a subject, the method comprising: administering an effective amount of a vaccinia virus to the subject, the vaccinia virus comprising a gene encoding a modified R2 protein comprising an amino acid sequence at least 90% identical to the amino acid sequence of SEQ ID NO: 1, wherein the vaccinia virus does not express a wild type R2 protein; and
   wherein the modified R2 protein expressed by the vaccinia virus comprises a substitution of a tyrosine residue, wherein the substituted tyrosine residue corresponds to position 300 of SEQ ID NO: 1, or
   wherein the modified R2 protein expressed by the vaccinia virus comprises a deletion of 7 amino acids of R1 binding domain (R1BD),
   wherein the neoplastic disorder comprises neoplastic disorder cells expressing ribonucleotide reductase and wherein the administering is effective to induce cell death in the neoplastic disorder cells.

12. The method of claim 11, wherein the neoplastic disorder is a cancer selected from breast cancer, colorectal cancer, hepatic cancer, pancreatic cancer, skin cancer, lung cancer, esophageal cancer, leukemia, ovarian cancer, head and neck cancer, gliomas, and gastric cancer.

13. The method of claim 11, wherein the modified R2 protein expressed by the vaccinia virus comprises a substitution of a tyrosine residue, wherein the substituted tyrosine residue corresponds to position 300 of SEQ ID NO: 1.

14. The method of claim 13, wherein the modified R2 protein comprises an amino acid sequence at least 95% identical to the amino acid sequence of SEQ ID NO: 1.

15. The method of claim 13, wherein the tyrosine residue is substituted with phenylalanine.

16. The method of claim 11, wherein the modified R2 protein comprises the deletion of 7 amino acids of the R1BD.

17. The method of claim 16, wherein the modified R2 protein comprises an amino acid sequence at least 95% identical to the amino acid sequence of SEQ ID NO: 1.

18. The method of claim 11, wherein the vaccinia virus further comprises a functionally inactivated thymidine kinase gene.

19. The method of claim 11, wherein the vaccinia virus further comprises a functionally inactivated R1 gene.

20. The method of claim 11, wherein the vaccinia virus further comprises a functionally inactivated vaccinia virus growth factor gene or a functionally inactivated nucleotide metabolism-related gene.

* * * * *